US012692283B2

(12) United States Patent
Shen et al.

(10) Patent No.: US 12,692,283 B2
(45) Date of Patent: Jul. 28, 2026

(54) LIGNAN DERIVATIVE, PREPARATION METHOD THEREFOR AND USE THEREOF

(71) Applicants: SHANGHAI INSTITUTE OF MATERIA MEDICA, CHINESE ACADEMY OF SCIENCES, Shanghai (CN); SUZHOU QINGYA QIRUI BIOTECHNOLOGY CO., LTD., Jiangsu (CN)

(72) Inventors: Jianhua Shen, Shanghai (CN); Zhiyuan Zhu, Jiangsu (CN); Xiaomei Li, Shanghai (CN); Kai Wang, Shanghai (CN); Jia Liu, Shanghai (CN)

(73) Assignees: SHANGHAI INSTITUTE OF MATERIA MEDICA, CHINESE ACADEMY OF SCIENCE, Shanghai (CN); SUZHOU QINGYA QIRUI BIOTECHNOLOGY CO., LTD., Jiangsu (CN)

( * ) Notice: Subject to any disclaimer, the term of this patent is extended or adjusted under 35 U.S.C. 154(b) by 340 days.

(21) Appl. No.: 18/556,165

(22) PCT Filed: Mar. 25, 2022

(86) PCT No.: PCT/CN2022/083003
§ 371 (c)(1),
(2) Date: Oct. 19, 2023

(87) PCT Pub. No.: WO2022/222686
PCT Pub. Date: Oct. 27, 2022

(65) Prior Publication Data

US 2025/0059219 A1 Feb. 20, 2025

(30) Foreign Application Priority Data

Apr. 19, 2021 (CN) ........................ 202110419576.1

(51) Int. Cl.
*A61P 25/28* (2006.01)
*A61K 31/365* (2006.01)
(Continued)

(52) U.S. Cl.
CPC ........ *C07F 9/65515* (2013.01); *A61K 31/365* (2013.01); *A61K 31/665* (2013.01);
(Continued)

(58) Field of Classification Search
CPC .... C07F 9/65515; C07F 9/655; A61K 31/365; A61K 31/665; A61K 31/4025;
(Continued)

(56) References Cited

FOREIGN PATENT DOCUMENTS

| | | |
|---|---|---|
| CN | 102342929 A | 2/2012 |
| CN | 102451178 A | 5/2012 |

(Continued)

OTHER PUBLICATIONS

International Search Report and Written Opinion in International Application No. PCT/CN2022/083003,11 pages, with partial translation Apr. 27, 2022.

(Continued)

*Primary Examiner* — Taylor V Oh
(74) *Attorney, Agent, or Firm* — Heslin Rothenberg Farley & Mesiti P.C.

(57) ABSTRACT

Disclosed in the present invention are a lignan derivative, a preparation method therefor and the use thereof. The structure of the lignan derivative is as shown in a formula I, wherein in the formula, the definition of each substituent is as described in the description and claims. The lignan derivative of the present invention can be used as an inhibitor of mitochondrial respiratory chain complex I to inhibit mitochondrial oxidative phosphorylation and ATP
(Continued)

generation, and can also be used for preventing and/or treating diseases associated with the elevated activity or expression of the mitochondrial respiratory chain complex I or enhanced mitochondrial oxidative phosphorylation.

(I)

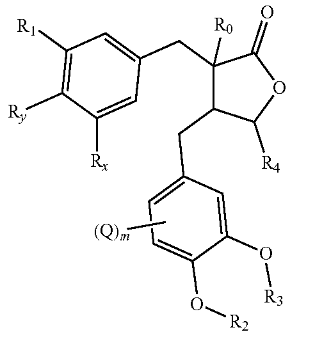

20 Claims, 6 Drawing Sheets

(51) Int. Cl.

| | |
|---|---|
| ***A61K 31/665*** | (2006.01) |
| ***A61P 1/00*** | (2006.01) |
| ***A61P 1/16*** | (2006.01) |
| ***A61P 11/00*** | (2006.01) |
| ***A61P 19/02*** | (2006.01) |
| ***A61P 35/00*** | (2006.01) |
| ***A61P 35/02*** | (2006.01) |
| ***C07D 307/33*** | (2006.01) |
| ***C07F 9/655*** | (2006.01) |

(52) U.S. Cl.
CPC .................. *A61P 1/00* (2018.01); *A61P 1/16* (2018.01); *A61P 11/00* (2018.01); *A61P 19/02* (2018.01); *A61P 25/28* (2018.01); *A61P 35/00* (2018.01); *A61P 35/02* (2018.01); *C07D 307/33* (2013.01)

(58) Field of Classification Search
CPC .... A61P 1/00; A61P 1/16; A61P 11/00; A61P 19/02; A61P 25/28; A61P 35/00; A61P 35/02; A61P 3/10; A61P 9/10; A61P 13/12; A61P 21/00; A61P 25/00; A61P 27/06; A61P 27/12; A61P 39/06; C07D 307/33; C07D 405/12
USPC .......................................................... 514/99
See application file for complete search history.

(56) References Cited

FOREIGN PATENT DOCUMENTS

| | | |
|---|---|---|
| CN | 103417554 A | 12/2013 |
| CN | 104220041 A | 12/2014 |

OTHER PUBLICATIONS

Ragamustari et al., “A Novel O-Methyltransferase Involved in the First Methylation Step of Yatein Biosynthesis from Matairesinol in Anthriscus Sylvestris”, Plant Biotechnology, vol. 30, pp. 375-384. 2013.
Kudou et al. “Synthesis and Antitumor Evaluation of Arctigenin Derivatives Based on Antiausterity Strategy”, European Journal of Medicinal Chemistry, vol. 60, pp. 76-88. 2013.
Duan et al., “Design and Synthesis of Novel Arctigenin Analogues for the Amelioration of Metabolic Disorders”, ACS Medicinal Chemistry Letters, vol. 6, pp. 386-391. 2015.
Denise et al. “5-Fluorouracil resistant colon cancer cells are addicted to OXPHOS to survive and enhance stem-like traits”, Oncotarget, vol. 6, No. 39, pp. 41706-41721. Oct. 21, 2015.
Molina et al., “An inhibitor of oxidative phosphorylation exploits cancer vulnerability”, Nature Medicine, vol. 24, pp. 1036-1046. Jul. 2018.
Crespo-Garcia et al., “Pathological angiogenesis in retinopathy engages cellular senescence and is amenable to therapeutic elimination via BCL-xL inhibition”, Cell Metabolism, vol. 33, pp. 818-832. Apr. 6, 2021.
Hubackova et al., “Selective elimination of senescent cells by mitochondrial targeting is regulated by ANT2”, Cell Death & Differentiation, vol. 26, pp. 276-290. 2019, published online 2018.
Prasnikar et al., “Senescent cells as promising targets to tackle age-related diseases”, Ageing Research Reviews, vol. 66, 33 pages. 2021; online Dec. 29, 2020.
Gao et al., “Overview of the anti-inflammatory effects, pharmacokinetic properties and clinical efficacies of arctigenin and arctiin from Arctium lappa L”, Acta Pharmacologica Sinica, vol. 39, pp. 787-801. 2018.
Lai et al., “Integrated Compound Profiling Screens Identify the Mitochondrial Electron Transport Chain as the Molecular Target of the Natural Products Manassantin, Sesquicillin, and Arctigenin”, ACS Chemical Biology, vol. 8, pp. 257-267. Nov. 8, 2012.
Medarde et al., “Synthesis, Antitumoral and Antiviral Evaluation of Halo- and Demethyl-Yatein Derivatives”, Arch. Pharm., vol. 328, pp. 640-644. 1995.
Sakakibara et al., “Biosynthesis of Yatein in Anthriscus Sylvestris”, Org. Biomol. Chem, vol. 1, pp. 2474-2485. Jun. 20, 2003.
Yang et al., “Progress on Burdock: A Review”, Journal of Changchun University of Traditional Chinese Medicine, vol. 30, No. 10, p. 827-828, with abstract. 2014.

LIGNAN DERIVATIVE, PREPARATION METHOD THEREFOR AND USE THEREOF

CROSS REFERENCE TO RELATED APPLICATIONS

This application is a U.S. National Phase filing under 35 U.S.C. § 371 of International Application PCT/CN2022/083003, filed Mar. 25, 2022, and published as WO 2022/222686 A1 on Oct. 27, 2022. PCT/CN2022/083003 claims priority from China application number 202110419576.1, filed Apr. 19, 2021. The entire contents of each of these prior applications are hereby incorporated herein by reference.

TECHNICAL FIELD

The present invention relates to the field of medicinal chemistry. Specifically, the present invention relates to lignan derivative and use thereof as mitochondrial respiratory chain complex I inhibitor.

BACKGROUND ART

Mitochondrial respiratory chain complex I (NADH: ubiquinone oxidoreductase) is located in the inner membrane of mitochondria and is one of the most important protein complexes in the oxidative phosphorylation (OXPHOS) respiratory chain. It can transfer electrons from Nicotinamide Adenine Dinucleotide (NADH) to coenzyme Q (CoQ), and at the same time, four protons are coupled and pumped out from the mitochondrial matrix to the intermembrane space, forming a transmembrane proton gradient, driving the synthesis of adenine nucleoside triphosphate (ATP). The protons pumped out by Complex I account for about 40% of the entire respiratory chain. Electron transfer through complex I and coupled proton pumping are the major pathways for energy production in normal cells.

Unlike normal cells, tumor cells usually rely more on the glycolytic pathway for energy supply than the mitochondrial respiration OXPHOS pathway. However, recent researches and developments have found that the energy metabolism mode is constantly changing during the occurrence of tumors and the transformation of tumor cells. Some tumors shift their energy supply mode to OXPHOS due to mutations in glycolysis-related genes. Changes in the energy metabolism of tumor cells provide new ideas for tumor treatment, and inhibiting the OXPHOS process in such tumors has become a unique therapeutic approach. Researchers at the Anderson Cancer Center, University of Texas, USA have developed a series of highly efficient inhibitors of mitochondrial respiratory chain complex I, which can effectively inhibit the growth of acute leukemia cell lines in in vitro models. Among them, IACS-10759 having good pharmacokinetic properties and oral bioavailability is currently in Phase I clinical trials for acute myeloid leukemia as well as solid tumors and lymphomas (Nature Medicine, 2018, 24, 1036-1046). In addition, new research shows that the therapeutic resistance of tumor cells that rely on the glycolytic metabolic pathway after some "targeted therapies" can be achieved through metabolic reorganization to an oxphos-dependent shift, and oxphos inhibitors can effectively target drug-resistant tumor cells undergoing metabolic reorganization. For example, the mitochondrial respiratory chain complex I inhibitor metformin effectively kills 5-fluorouracil-resistant colon cancer cells. (Oncotarget. 2015; 6 (39): 41706-21).

In addition to inhibiting the energy supply of the OXPHOS metabolic pathway, mitochondrial respiratory chain complex I inhibitors also exert anti-tumor effects through a broader mechanism, such as increasing the accumulation of intracellular reactive oxygen species (ROS) leading to cytotoxicity, inhibiting anaerobic inducible factor 1 alpha (HIF-1α) signal, interfering with mitochondrial membrane potential, activating AMP-activated protein kinase (AMPK) and the like. It can be seen that mitochondrial respiratory chain complex I inhibitors may also be used as broad-spectrum anti-tumor drugs or in combination with anti-tumor drugs of other mechanisms.

On the other hand, studies have shown that many age-related diseases are related to cell senescence, including progeria syndrome, cardiovascular disease, osteoarthritis, cancer, neurodegenerative disease, chronic kidney disease, chronic obstructive pulmonary disease, idiopathic pulmonary fibrosis, type II diabetes, skin aging, stain deposition and other diseases. Senescent cells are a class of cells that are permanently arrested in the cell cycle, yet maintain high metabolic activity and continue to release senescence-associated secretory phenotypes (SASP). Senescent cells are passively accumulated in organs during the aging process, causing tissue dysfunction. The primary senescent cells produced by the "wear and tear" process of normal tissues will induce senescence in adjacent cells and cause more senescent cells to be generated at the lesion site, resulting in the loss of cells with the ability to proliferate in the tissue, thus leading to the occurrence of disease. For example, the loss of pancreatic beta cells can lead to diabetes, and the loss of lung epithelial cells can lead to pulmonary fibrosis. At the same time, inflammation caused by SASP secreted by senescent cells can also cause diseases, such as cardiovascular diseases such as atherosclerosis, myocardial infarction, cardiomyocyte hypertrophy, and lung diseases such as chronic obstructive pulmonary disease. In addition, SASP-mediated extracellular matrix remodeling can also play a role in promoting tissue fibrosis, such as pulmonary fibrosis, liver fibrosis, and renal fibrosis. Senescent cells are commonly found in numerous types of liver disease, including viral hepatitis, alcoholic liver disease, non-alcoholic fatty liver disease, liver fibrosis, cirrhosis, and hepatocellular carcinoma. Aged hepatocytes, astrocytes and immune cells can promote the progression of liver disease through SASP, metabolic function, immune response and other pathways. Similarly, senescent cells also exist in other digestive organs such as the esophagus, stomach, bile duct, pancreas, intestine, etc., and play an important role in the occurrence and development of cholangitis, inflammatory bowel disease, digestive tract tumors and other diseases. Aging is a major risk factor for neurodegenerative diseases, and the formation of many neurodegenerative diseases, including Alzheimer's disease and Parkinson's disease, is related to cell senescence. Senescent cells promote the formation and development of neurodegenerative diseases by causing neuroinflammation, increasing oxidative stress, destroying neuron function, and hindering nervous system regeneration. Senescent cell scavengers are a class of compounds that can selectively eliminate senescent cells. They can extend healthy lifespan and help individuals reduce chronic disease problems in the aging process, including reducing tumor occurrence, extending median survival, and alleviating aging changes such as atherosclerosis, osteoarthritis, cataracts, macular degeneration, cardiac hypertrophy, chronic kidney disease, chronic liver disease, pulmonary fibrosis, neurodegenerative disease, lipid metabolism disorder and sarcopenia. Several senescent cell scavengers have entered clinical studies for the treatment of aging-related diseases. For example, the combination of dasatinib and quercetin has entered phase I clinical studies for the treatment of idiopathic pulmonary fibrosis, and UBX0101 has entered phase II clinical studies for the treatment of osteoarthritis (Ageing Research Reviews, 2020, 66:101251). Senescent cells are accumulated in the microvessels of the diseased retina. Local removal of senescent cells with drugs can effectively prevent pathological angiogenesis in the retina and promote normal blood vessel repair (Cell Metab, 2021, 33:818). The senescent cell scavenger UBX1325 is currently in clinical trials for the treatment of diabetic retinopathy and age-related macular degeneration.

In addition to enhanced OXPHOS in some subsets of tumor cells, studies have shown that the OXPHOS process is also enhanced in senescent cells. To maintain a high-level secretory phenotype, senescent cells must make significant metabolic changes, such as increased oxygen consumption and energy production, more active lipid breakdown, and simultaneous production of high levels of ROS. Compared with glycolysis, senescent cells rely more on the OXPHOS function of mitochondria to provide energy. The enhancement of mitochondrial function is an important determinant of the secretion of SASP by senescent cells. Therefore, in theory, targeting mitochondrial respiratory chain complex I and blocking OXPHOS is a reasonable method to eliminate senescent cells. Studies have shown that mitochondria-targeted tamoxifen can selectively eliminate senescent cells by inhibiting mitochondrial respiratory chain complex I and reducing mitochondrial membrane potential (Cell Death & Differentiation, 2018, 26 (2), 276-290). Therefore, it may be an effective method to apply mitochondrial respiratory chain complex I inhibitors to prevent or treat cell aging-related diseases.

The literature (ACS Chemical Biology, 2013, 8 (1), 257-267) has reported that Arctigenin, a natural product, is a moderately potent and selective inhibitor of mitochondrial respiratory chain complex I. Arctigenin has pharmacological effects such as anti-inflammation, anti-infection, anti-metabolic disorder, and anti-nerve damage, and is very effective in the treatment of cancer, atherosclerosis, diabetes, Alzheimer's disease and other aging-related diseases. However, it is easily metabolized after oral administration, has poor pharmacokinetic properties, and has low bioavailability, which limits its application as an oral drug (Acta Pharmacologica *Sinica,* 2018, 39, 787-801).

SUMMARY OF THE INVENTION

The object of the present invention is to provide a lignan derivative obtained by structurally modifying arctigenin, which can effectively inhibit the mitochondrial respiratory chain complex I.

The first aspect of the present invention provides a compound represented by formula I, an enantiomer, diastereoisomer, racemic mixture, deuterated compound or pharmaceutically acceptable salt thereof, (I)

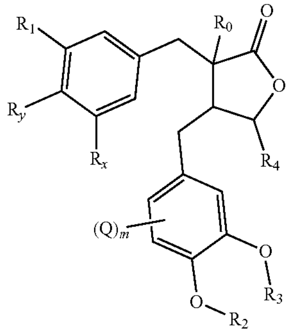

wherein $R_x$ is a hydrogen, hydroxyl, or halogen;

$R_0$ is a hydrogen, halogen, $C_1$-$C_6$ alkyl, hydroxyl-substituted $C_1$-$C_6$ alkyl, or $C_1$-$C_6$ haloalkyl;

$R_1$ is a halogen, $C_1$-$C_6$ haloalkyl, —$N(R_5)_2$, $C_1$-$C_6$ alkoxy, $C_1$-$C_6$ deuterated alkoxy or —O-L-G; wherein L is a $C_{1-6}$ alkylene, a hydrogen atom of the alkylene is optionally substituted by a halogen, hydroxyl, —O in the manner and number allowed by the chemical bond; G is a halogen, $C_1$-$C_6$ haloalkyl, —CN, —$N(R_9)_2$, —$COOR_{10}$, —$P^+(R_{11})_3Y^-$, —$N^+(R_{11})_3Y^-$, $C_{6-10}$ aryl, $C_{6-10}$ aryloxy, 4-8 membered heterocyclyl or 5-10 membered heteroaryl; the aryl, aryloxy, heterocyclyl and heteroaryl are unsubstituted or substituted by 1, 2, 3 or 4 groups selected from the following group consisting of a halogen, hydroxyl, —$N(R_{12})_2$, nitro, cyano, $C_1$-$C_6$ alkyl, $C_1$-$C_6$ haloalkyl, $C_1$-$C_6$ alkoxy, 4-8 membered heterocyclyl;

$R_2$ and $R_3$ are each independently a $C_1$-$C_6$ alkyl, or $C_1$-$C_6$ haloalkyl, or $R_2$ and $R_3$ are connected together with the connected C to form an unsubstituted or substituted 5-8 membered heterocyclyl, and the "substitution" refers to substitution with one or more substituents selected from the group consisting of a halogen and $C_1$-$C_6$ alkyl;

$R_4$ is a hydrogen or $C_1$-$C_6$ alkyl;

each $R_5$ is independently a hydrogen, $C_1$-$C_6$ alkyl, —$SO_2R_{13}$, or —$COR_{13}$;

Ry is a hydroxyl or

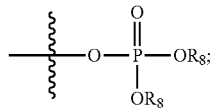

each $R_9$ is independently a hydrogen, $C_1$-$C_6$ alkyl, $C_{6-10}$ aryl, 5-10 membered heteroaryl, and the aryl and heteroaryl are optionally substituted by 1-4 groups selected from the group consisting of a halogen, hydroxyl, —$N(R_{12})_2$, nitro, cyano, $C_1$-$C_6$ alkyl, $C_1$-$C_6$ haloalkyl, $C_1$-$C_6$ alkoxy, and 4-8 membered heterocyclyl;

each $R_{11}$ is independently a $C_1$-$C_6$ alkyl or $C_{6-10}$ aryl, the aryl is optionally substituted by 1-4 groups selected from the group consisting of a halogen, $C_{1-6}$ alkyl and $C_{1-6}$ alkoxy;

$R_8$, $R_{10}$, and $R_{12}$ are each independently a hydrogen or $C_1$-$C_6$ alkyl;

$R_{13}$ is a $C_1$-$C_6$ alkyl;

$Y^-$ is a halide ion, formate ion, acetate ion, trifluoroacetate ion or hydroxide ion;

m is 0, 1, 2 or 3; each Q is independently a halogen or $C_1$-$C_6$ alkyl;

provided that $R_1$ is not a $C_1$-$C_6$ alkoxy group when $R_0$, $R_4$, and $R_x$ are all hydrogen and Ry is a hydroxyl.

In the present invention, halogen includes four atoms, fluorine, chlorine, bromine and iodine, and the halide ion is a monovalent negative ion of fluorine, chlorine, bromine or iodine.

In another preferred example, $R_1$ is a halogen, $C_1$-$C_4$ haloalkyl, —$N(R_5)_2$, $C_1$-$C_4$ alkoxy, $C_1$-$C_4$ deuterated alkoxy or —O-L-G; wherein, L is a $C_{1-4}$ alkylene, 1, 2 or 3 hydrogen atoms on the alkylene are optionally substituted by a halogen, hydroxyl, —O in a manner allowed by chemical bonding; G is a halogen, $C_1$-$C_4$ haloalkyl, —CN, —$N(R_9)_2$, —$COOR_{10}$, —$P^+(R_{11})_3Y^-$, —$N^+(R_{11})_3Y^-$, phenyl, phenyloxy, 4-6-membered heterocyclyl or 6-8-membered heteroaryl; the phenyl, phenyloxy, heterocyclyl and heteroaryl are unsubstituted or substituted by 1, 2 or 3 groups selected from the group consisting of a halogen, hydroxyl, —$N(R_{12})_2$, nitro, cyano, $C_1$-$C_6$ alkyl, $C_1$-$C_6$ haloalkyl, $C_1$-$C_6$ alkoxy, and 4-8 membered heterocyclyl.

In another preferred example, each $R_5$ is independently a hydrogen or $C_1$-$C_4$ alkyl. In another preferred example, each $R_9$ is independently a hydrogen or $C_1$-$C_4$ alkyl. In another preferred example, $R_{10}$ is a hydrogen or $C_1$-$C_4$ alkyl. In another preferred example, each $R_{11}$ is independently a $C_1$-$C_4$ alkyl or phenyl. In another preferred example, each $R_{12}$ is independently a hydrogen or $C_1$-$C_4$ alkyl.

In another preferred example, Ry is a hydroxyl or

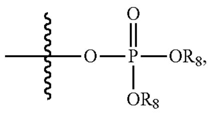

wherein each $R_8$ is independently a hydrogen or $C_1$-$C_4$ alkyl.

In another preferred example, $R_x$ is a hydrogen, fluorine, chlorine or bromine.

In another preferred example, $R_0$ is a hydrogen, fluorine, chlorine, bromine, $C_1$-$C_4$ alkyl, hydroxyl-substituted $C_1$-$C_4$ alkyl, $C_1$-$C_4$ haloalkyl.

In another preferred example, $R_4$ is a hydrogen or $C_1$-$C_4$ alkyl.

In another preferred example, $R_2$ and $R_3$ are each independently a $C_1$-$C_4$ alkyl, or $R_2$ and $R_3$ are connected together with the connected C to form

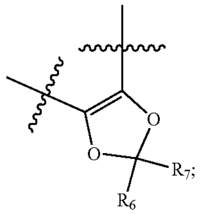

$R_6$ and $R_7$ are each independently a hydrogen, $C_1$-$C_4$ alkyl or halogen.

In another preferred example, the compound has the following formula (IIa):

(IIa)

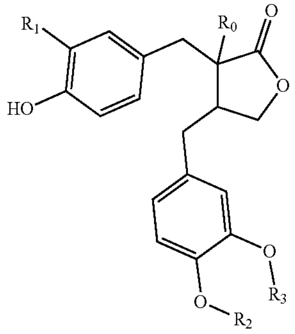

wherein each substituent is defined as above; and when $R_0$ is hydrogen, $R_1$ is not $C_1$-$C_6$ alkoxy.

In another preferred example, the compound has the following formula (IIb):

(IIb)

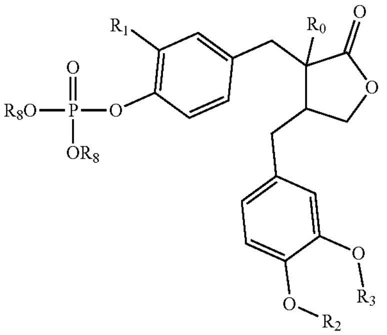

wherein, each substituent is defined as in claim 1.

In another preferred example, each $R_8$ is H.

In another preferred example, $R_1$ is a $C_1$-$C_4$ alkoxy or —O-L-G; wherein Lis a $C_{1-4}$ alkylene, and 1 or 2 hydrogen atoms on the alkylene are optionally substituted with fluorine, chlorine, bromine, hydroxyl, —O in a manner allowed by chemical bonding; G is a fluorine, chlorine, bromine, $C_1$-$C_4$ haloalkyl, —CN, —$N(R_9)_2$, —$COOR_{10}$, —$P^+(R_{11})_3Y^-$, —$N^+(R_{11})_3Y^-$, phenyl, phenyloxy, 4-6-membered heterocyclyl or 6-8-membered heteroaryl; the phenyl, phenyloxy, heterocyclyl and heteroaryl are not substituted or substituted by 1, 2 or 3 groups selected from the group consisting of a halogen, hydroxyl, —$N(R_{12})_2$, nitro, cyano, $C_1$-$C_4$ alkyl, $C_1$-$C_4$ haloalkyl, $C_1$-$C_4$ alkoxy, and 4-8 membered heterocyclyl;

wherein each $R_5$ is independently a hydrogen or $C_1$-$C_4$ alkyl; each $R_9$ is independently a hydrogen or $C_1$-$C_4$ alkyl; $R_{10}$ is a hydrogen or $C_1$-$C_4$ alkyl; each $R_{11}$ is independently a $C_1$-$C_4$ alkyl or phenyl; and each $R_{12}$ is independently a hydrogen or $C_1$-$C_4$ alkyl.

In another preferred example, $R_1$ is a $C_1$-$C_4$ alkoxy or —O-L-G; wherein Lis a $C_{1-4}$ alkylene; G is a phenyl or $C_1$-$C_4$ haloalkyl; Ry is a hydroxyl or —$OP(O)(OH)_2$; $R_0$ is a hydrogen or $C_1$-$C_6$ alkyl; $R_2$ and $R_3$ are each independently a $C_1$-$C_4$ alkyl.

In another preferred example, the compound is selected from the group consisting of

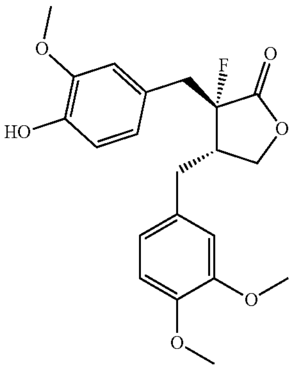
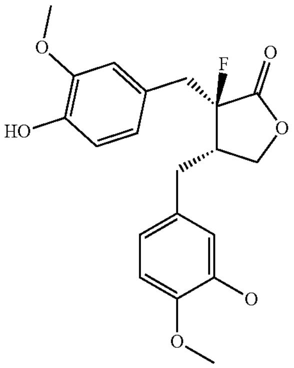
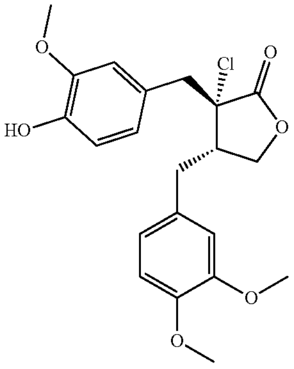
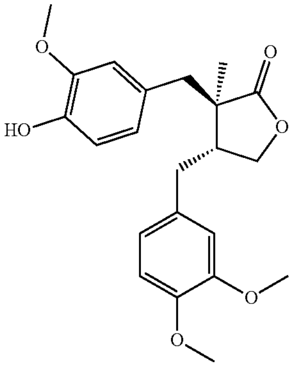
-continued
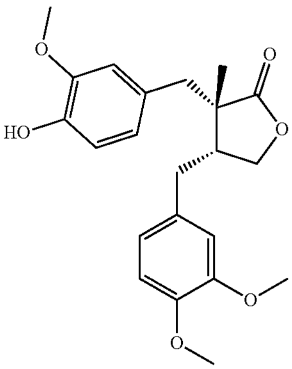
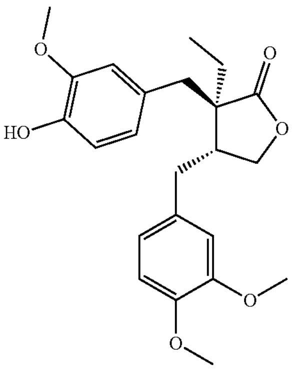
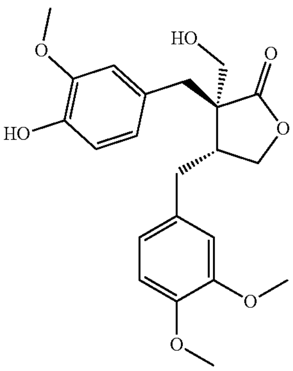
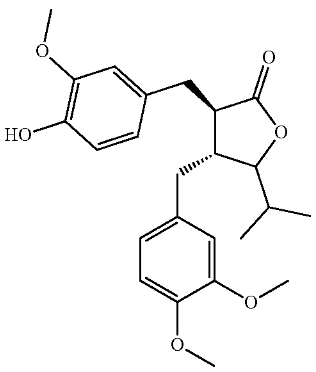

-continued
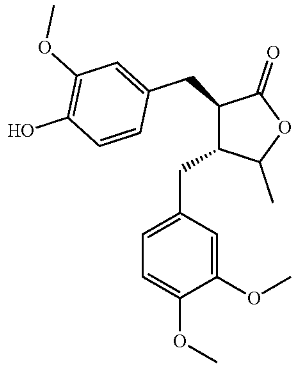
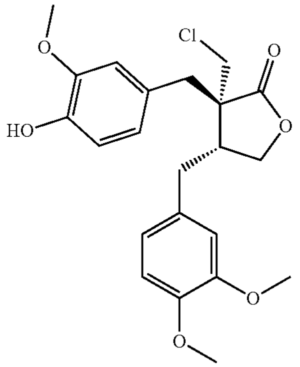
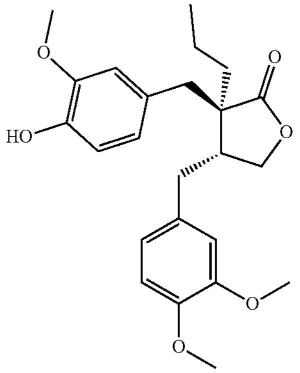
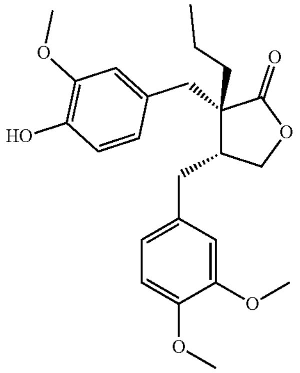
-continued
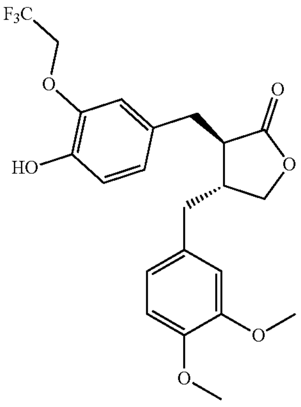
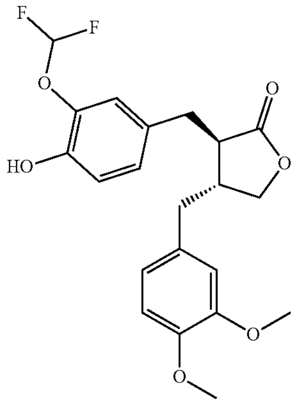
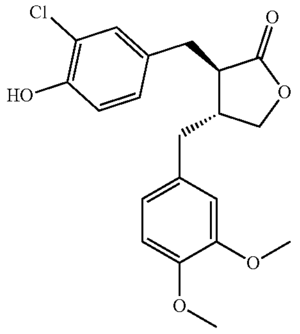
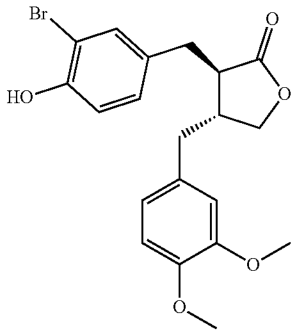

-continued
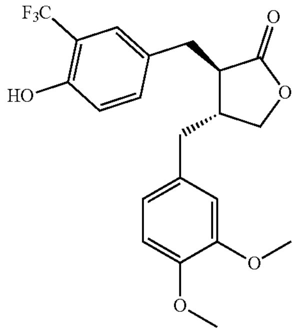
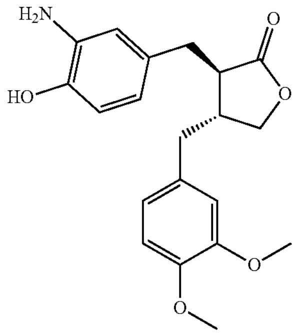
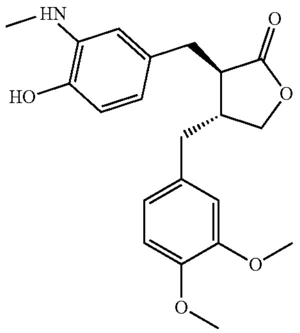
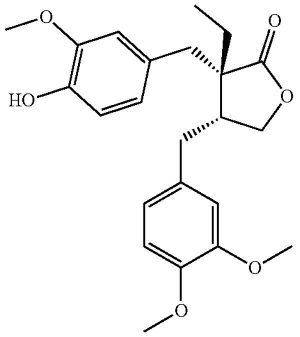
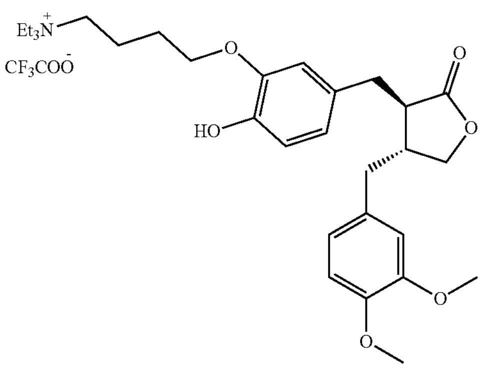
-continued
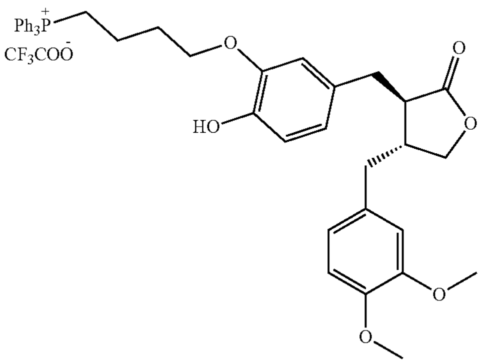
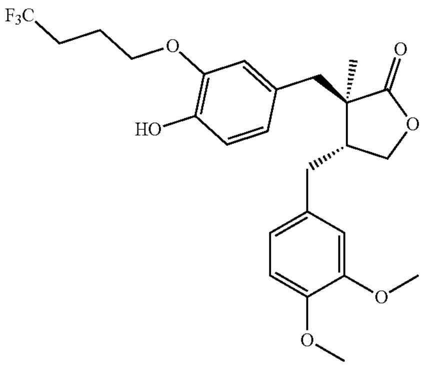
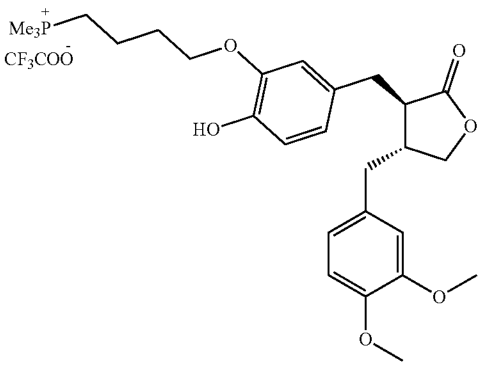
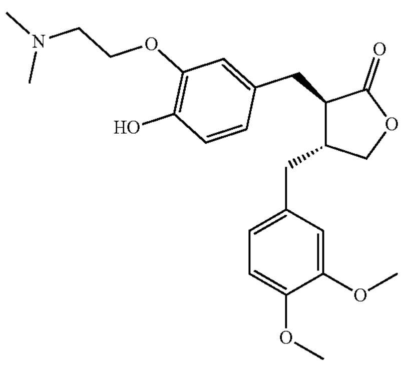

-continued
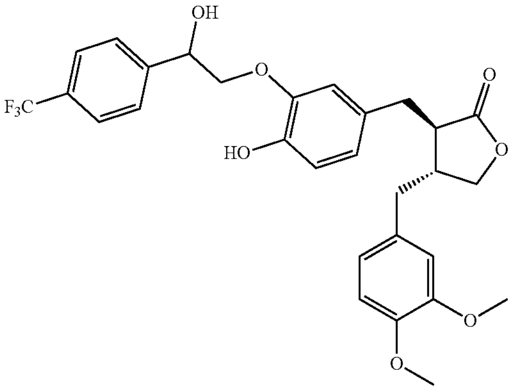
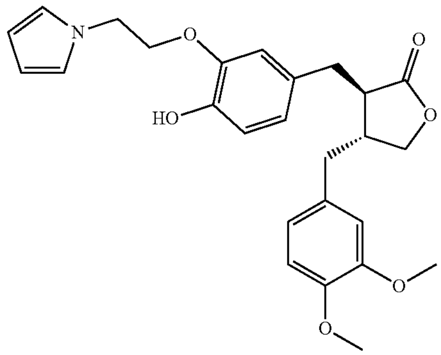
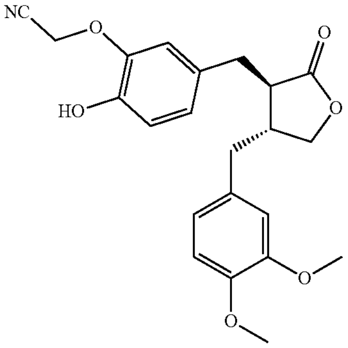
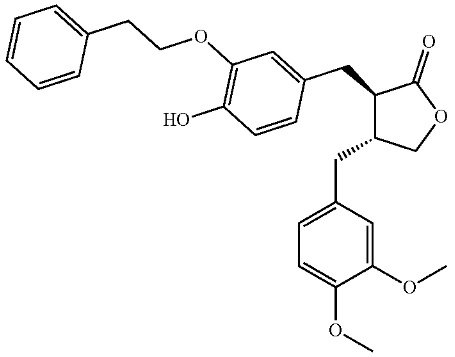
-continued
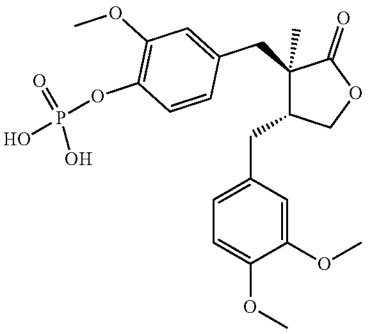
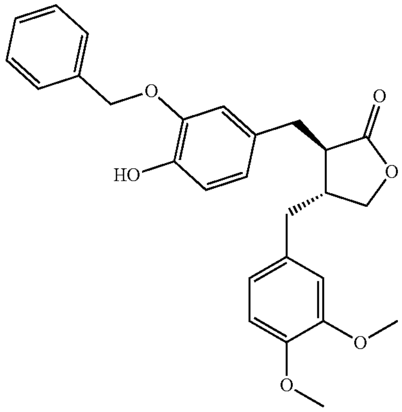
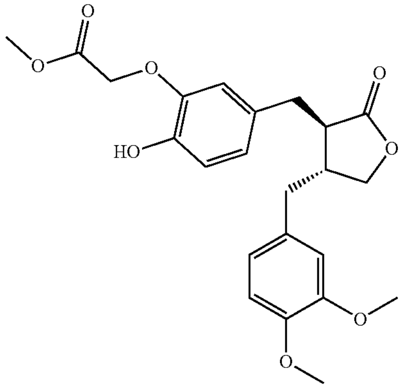
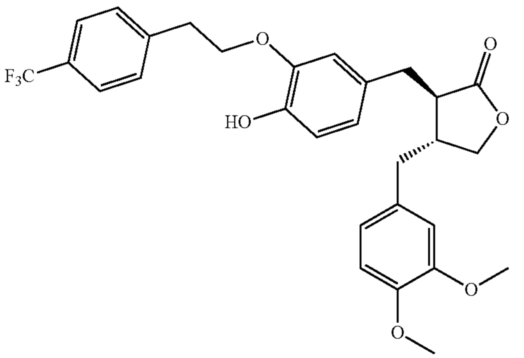

-continued
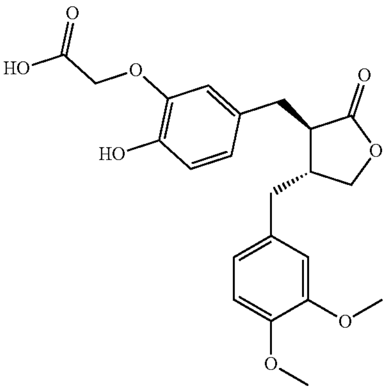
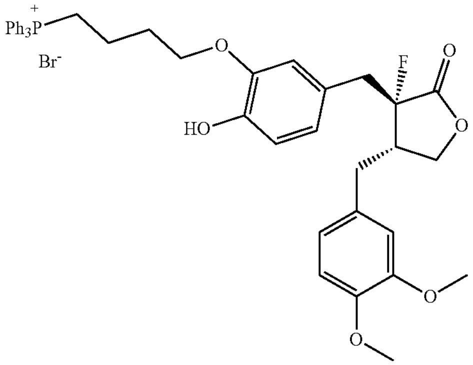
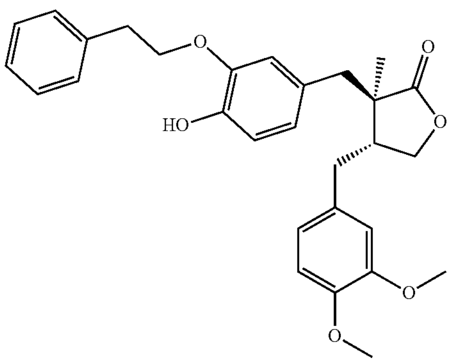
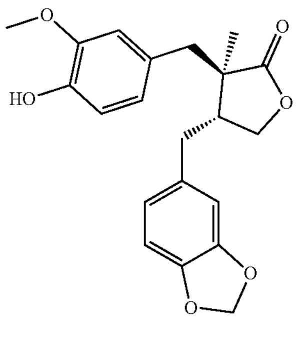
-continued
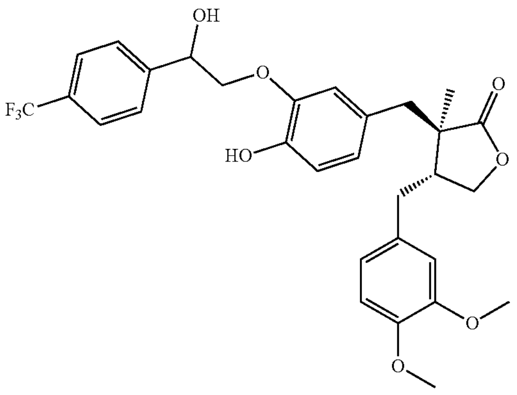
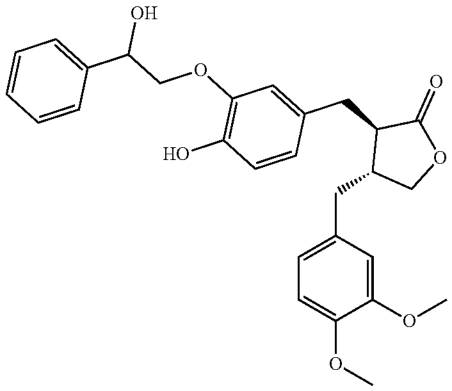
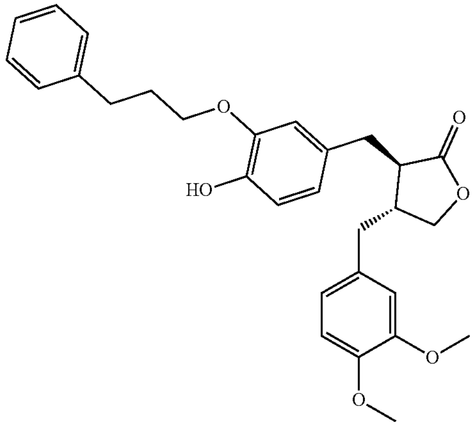
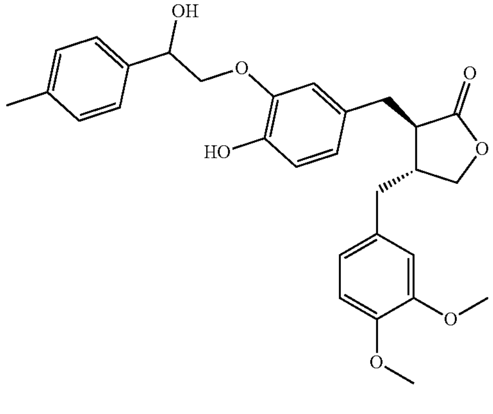

-continued

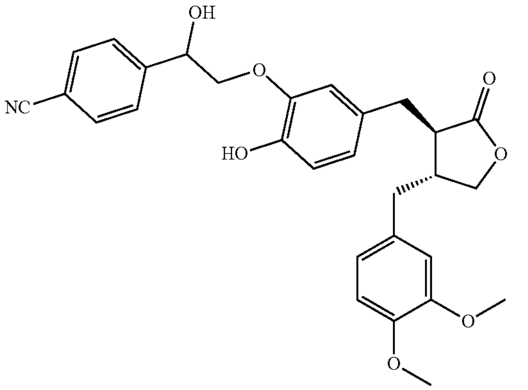

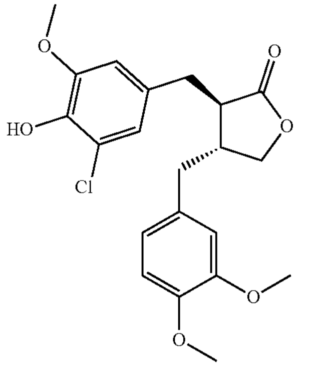

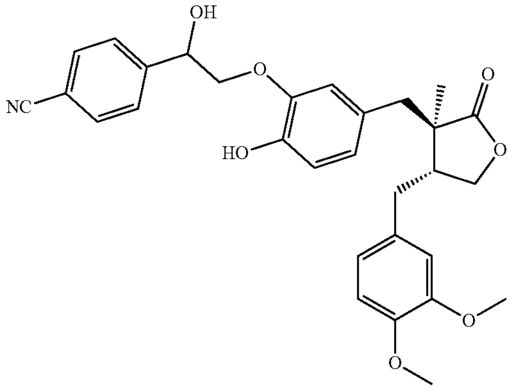

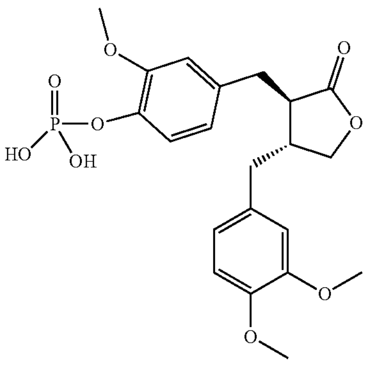

-continued

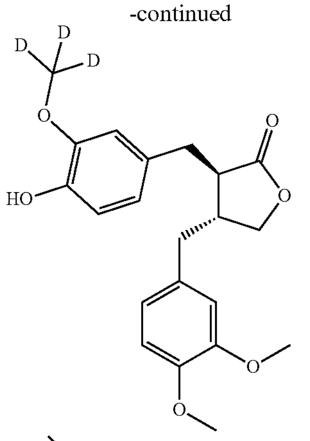

and

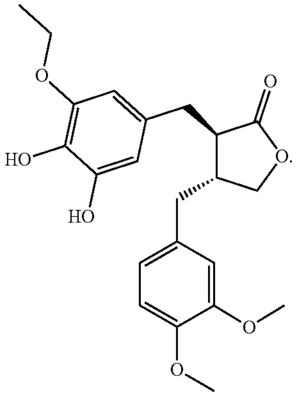

The second aspect of the present invention provides a pharmaceutical composition comprising the compound according to the first aspect, an enantiomer, diastereoisomer, racemic mixture, deuterated compound and pharmaceutically acceptable salt thereof; and a pharmaceutically acceptable carrier.

The third aspect of the present invention provides use of the compound according to the first aspect, the enantiomer, diastereoisomer, racemic mixture, deuterated compound and a pharmaceutically acceptable salt thereof or the pharmaceutical composition according to the second aspect for the preparation of mitochondrial respiratory chain complex I inhibitors; for the preparation of a medicament for preventing and/or treating a disease associated with increased activity or expression of mitochondrial respiratory chain complex I; for the preparation of a medicament for preventing and/or treating a disease related to enhanced mitochondrial oxidative phosphorylation; for the preparation of a medicament for preventing and/or treating a disease related to cell senescence; for the preparation of senescent cell scavenger; or for the preparation of a medicament for preventing and/or treating a tumor.

In another preferred example, the disease related to enhanced mitochondrial oxidative phosphorylation is a tumor that partially or completely relies on the oxidative phosphorylation metabolic pathway to supply energy.

In another preferred example, the disease related to enhanced mitochondrial oxidative phosphorylation is a disease related to cell senescence.

In another preferred example, the tumor is acute myeloid leukemia, neuroglioma, lymphoma, pancreatic cancer, uterine cancer, breast cancer, non-small cell lung cancer or hepatocellular carcinoma.

In another preferred example, the tumor is acute myeloid leukemia or neuroglioma.

In another preferred example, the disease related to cell senescence is selected from the group consisting of organ fibrosis disease, chronic lung disease, chronic kidney disease, chronic liver disease, osteoarthritis, neurodegenerative disease, inflammatory bowel disease, atherosclerosis, glaucoma, cataracts, macular degeneration, diabetes, diabetic retinopathy, pigmentation, and sarcopenia.

In another preferred example, the disease related to cell senescence is an organ fibrosis disease, selected from the group consisting of pulmonary fibrosis, liver fibrosis, and renal fibrosis. In another preferred example, the disease related to cell senescence is idiopathic pulmonary fibrosis. In another preferred example, the disease related to cell senescence is liver fibrosis. In another preferred example, the disease related to cell senescence is osteoarthritis.

In another preferred example, the disease related to cell senescence is a neurodegenerative disease, selected from the group consisting of Alzheimer's disease, Parkinson's disease, Huntington's disease, amyotrophic lateral sclerosis, and multiple sclerosis. In another preferred example, the disease related to cell senescence is Alzheimer's disease.

In another preferred example, the disease related to cell senescence is inflammatory bowel disease, selected from the group consisting of ulcerative colitis and Crohn's disease.

The present invention also provides a method for preparing the compound represented by the general formula (I), said method is selected from the following route 1 or route 2, specifically, depending on the type of the five-membered lactone ring.

Hereinafter, a protecting group Pg is a group that makes it possible, on the one hand, to protect reactive functional groups, such as a hydroxyl or amine, during the synthesis and, on the other hand, to allow the reactive functional groups to be restored to integrity at the end of the synthesis. Methods for protecting and deprotecting functional groups will be given in specific examples.

Route 1 is applicable to compounds wherein $R_0$ is a hydrogen, halogen, $C_1$-$C_6$ alkyl, hydroxyl-substituted $C_1$-$C_6$ alkyl, or $C_1$-$C_6$ haloalkyl; $R_4$ is a hydrogen; and other substituents are defined as above.

Route 1

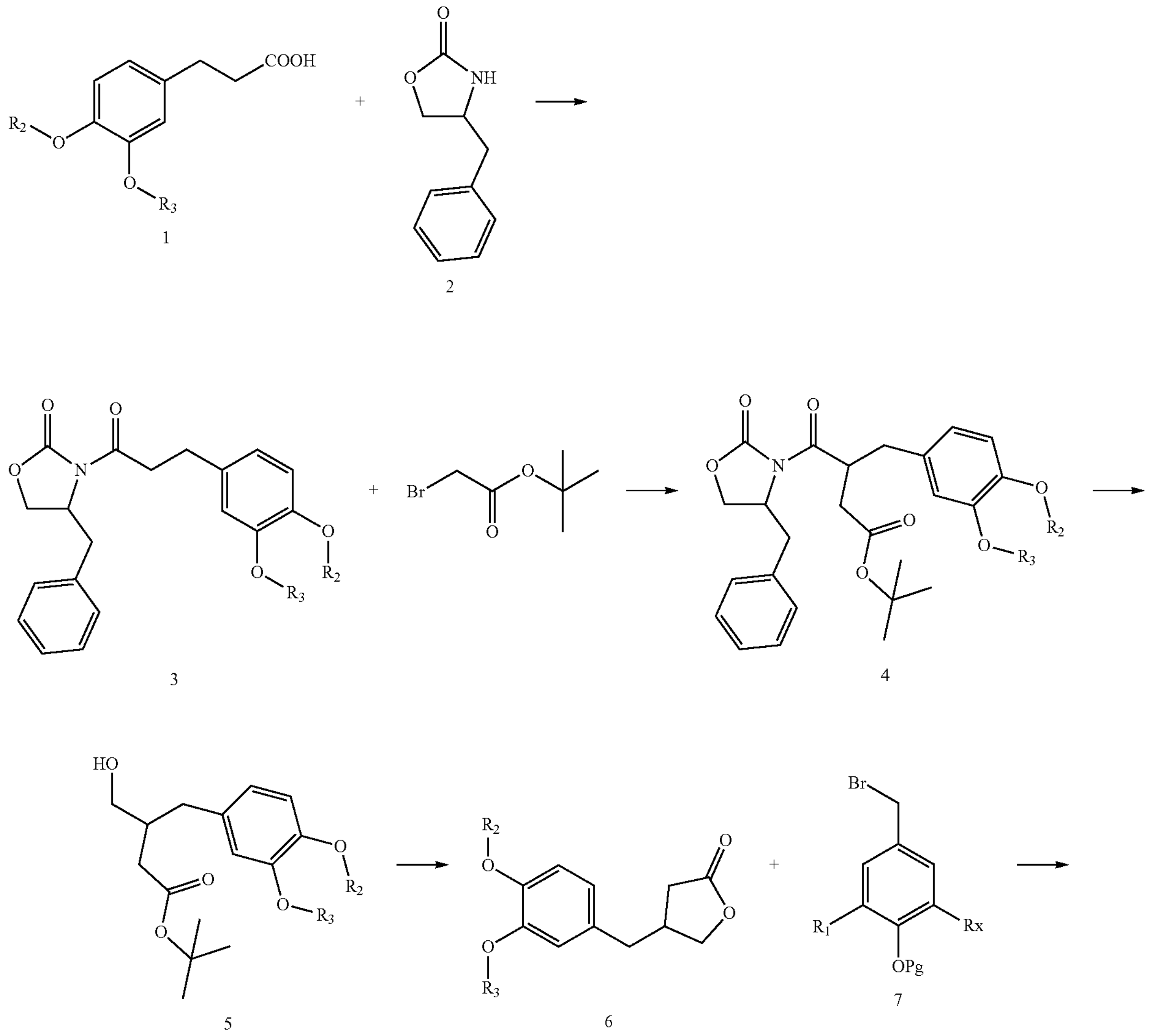

1 2 3 4 5 6 7

-continued

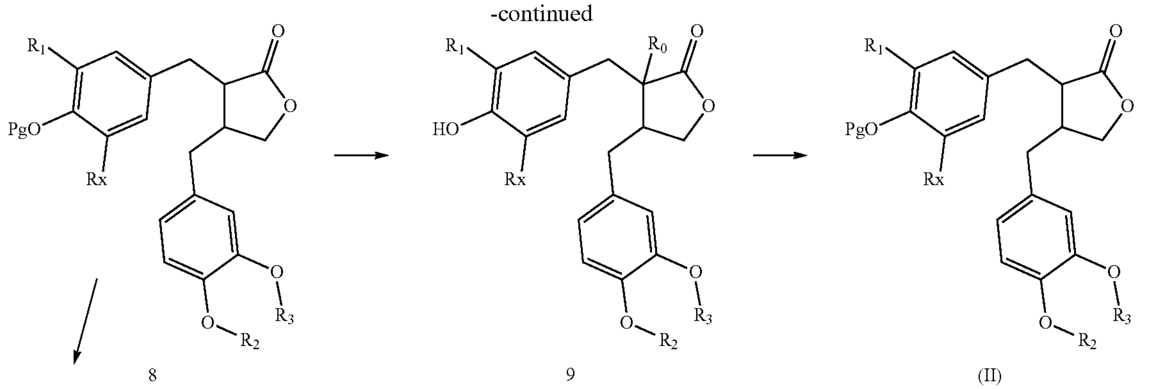

8 9 (II)

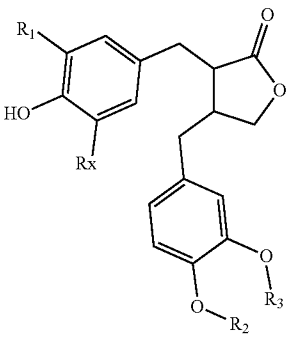

(I)

The purchased or synthesized phenylpropionic acid derivative 1 is condensed with the chiral prosthetic group 4-benzyloxazolidinone 2 to obtain compound 3. Subsequently, compound 3 undergoes an alkylation reaction at the α-position of the carbonyl under the action of a strong organic base with a large site resistance to obtain compound 4. Compound 4 is reduced with a reducing agent to eliminate the chiral prosthetic group to obtain compound 5 with a single configuration. Compound 5 undergoes a transesterification reaction under acid catalysis to obtain the key intermediate butyrolactone compound 6 with a single configuration. Subsequently, a strong organic base is used to remove hydrogen and a substituted benzyl is introduced to α position of the ester carbonyl of compound 6 to obtain compound 8. The phenolic hydroxyl of compound 8 is deprotected to obtain a compound of general formula (I). Compound 8 then undergoes hydrogen removal under the action of a strong organic base and attacks the electrophile to obtain α-substituted compound 9. The phenolic hydroxyl of compound 9 is deprotected to obtain a compound of general formula (II).

Route 2 is applicable to compounds wherein $R_0$ is a hydrogen, $R_4$ is a $C_1$-$C_6$ alkyl, and the other substituents are defined as above.

Route 2

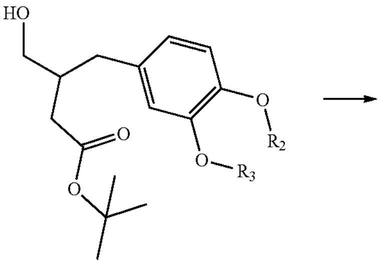

5

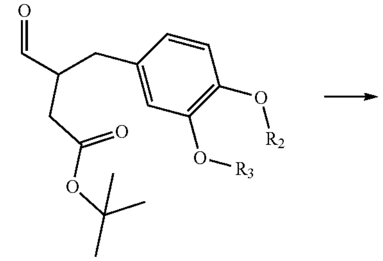

10

-continued

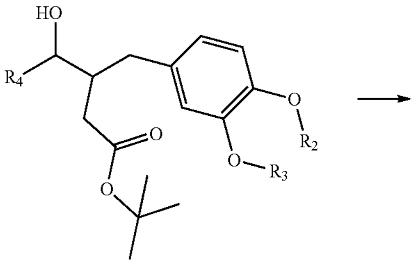

11

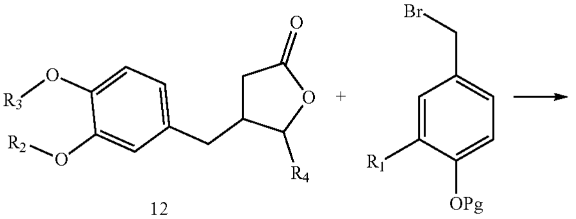

12 7

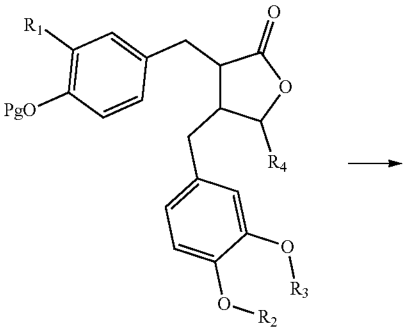

13

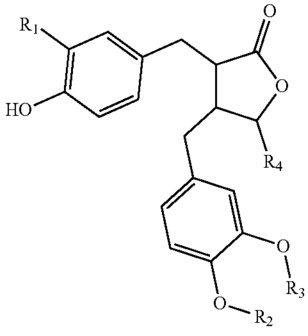

(III)

The second synthetic route starts from intermediate compound 5. The hydroxyl group of compound 5 is oxidized by an oxidant to obtain the corresponding aldehyde. Subsequently, the Grignard reagent is reacted with the aldehyde group to free the hydroxyl to obtain the corresponding compound 11. Compound 11 undergoes transesterification reaction under acid catalysis to the key intermediate butyrolactone compound 12. Subsequently, a strong organic base is used to remove hydrogen and a substituted benzyl compound is introduced to α position of the ester carbonyl of compound 12 to obtain compound 13. The phenolic hydroxyl of compound 13 is deprotected to obtain a compound of general formula (III).

DETAILED DESCRIPTION OF THE INVENTION

Figure 1:
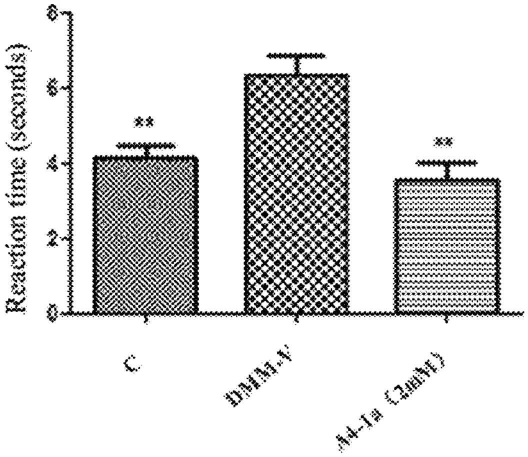
FIG. 1 shows the reaction time of mouse in the hot plate experiment.

After conducting extensive and intensive research, the inventors of the present application the inventors have discovered a series of compounds based on structural modification of arctigenin with improved inhibitory activity of mitochondrial respiratory chain complex I, improved oral pharmacokinetic properties, and significant oral effects in animal models, which have better drug-forming properties and application potential when used in the preparation of a medicament. On this basis, the present invention has been accomplished.

Terms

In the present invention, unless otherwise specified, the used terms have meanings routinely known to those skilled in the art.

In the present invention, the term "$C_1$-$C_6$" means one group having 1, 2, 3, 4, 5 or 6 carbon atoms, and "$C_1$-$C_8$" means one group having 1, 2, 3, 4, 5, 6, 7 or 8 carbon atoms, and so on. "3-8 membered" means one group having 3, 4, 5, 6, 7 or 8 ring atoms, and "5-7 membered" means one group having 5, 6 or 7 ring atoms, and so on.

In the present invention, "aromatic ring" and "aryl" are defined as a monocyclic and bicyclic system composed of a specific number of carbon atoms and complying with Hückel's rules, including but not limited to a benzene ring and naphthalene ring.

In the present invention, "heteroaryl ring" and "heteroaryl" are defined as a monocyclic and bicyclic ring system having a specific number of ring atoms and containing 1, 2, 3 or 4 heteroatoms (selected from N, O, S), while complying with Hückel Regular, including but not limited to pyridine, pyrrole, and imidazole.

In the present invention, "aryloxy" is defined as a group formed by connecting oxygen to an aromatic group, including but not limited to Ph-O—.

In the present invention, "heterocyclyl" is defined as a saturated or unsaturated non-aromatic cyclic group composed of a specific number of carbon atoms and containing 1, 2, 3 or 4 heteroatoms (selected from N, O, S), including but not limited to morpholine and piperazine.

In the present invention, the "alkyl" and similar "alkoxy" are branched and straight-chain hydrocarbyl and hydrocarbonoxy groups with a specific number of carbon atoms. Representative examples include but are not limited to methyl, methoxy, ethyl, ethoxy, n-propyl, n-propoxy, isopropyl, isopropoxy.

In the present invention, the term "haloalkyl" refers to a group formed by partial or complete substitution of hydrogen atoms by "halogen atoms" in an "alkyl" having a specific number of carbon atoms.

In the present invention, the "halogen atom" includes fluorine, chlorine, bromine, and iodine.

In the present invention, the substitution is mono-substitution or poly-substitution, and the poly-substitution is disubstitution, tri-substitution, tetra-substitution or penta-substitution. The disubstituted means having two substituents, and so on.

The pharmaceutically acceptable salt of the present invention may be a salt formed by an anion and a positively charged group on the compound of formula I. Suitable anion is chloride, bromide, iodide, sulfate, nitrate, phosphate, citrate, methanesulfonate, trifluoroacetate, acetate, malate, tosylate, tartrate, fumarate, glutamate, glucuronate, lactate, glutarate or maleate ion. Similarly, salt can be formed from cation with negatively charged group on compounds of formula I. Suitable cation includes sodium, potassium, magnesium, calcium and ammonium ion, such as tetramethylammonium ion. In another preferred example, "pharmaceutically acceptable salt" refers to a salt formed by the compound of formula I with an acid selected from the group consisting of hydrofluoric acid, hydrochloric acid, hydrobromic acid, phosphoric acid, acetic acid, oxalic acid, sulfuric acid, nitric acid, methanesulfonic acid, sulfamic acid, salicylic acid, trifluoromethanesulfonic acid, naphthalenesulfonic acid, maleic acid, citric acid, acetic acid, lactic acid, tartaric acid, succinic acid, oxalic acid, pyruvic acid, malic acid, glutamic acid, p-toluenesulfonic acid, naphthalenesulfonic acid, ethanesulfonic acid, naphthalenedisulfonic acid, malonic acid, fumaric acid, propionic acid, oxalic acid, trifluoroacetic acid, stearic acid, parapeptic acid, hydroxylmaleic acid, phenylacetic acid, benzoic acid, glutamic acid, ascorbic acid, p-aminobenzene sulfonic acid, 2-acetoxybenzoic acid and isethionic acid, etc.; or a sodium salt, potassium salt, calcium salt, aluminum salt or ammonium salt formed by the compound of formula I and an inorganic base; or a methylamine salt, ethylamine salt or ethanolamine salt formed from the compound of formula I and an organic base.

The compound of formula I of the present invention or the pharmaceutically acceptable salt thereof is distilled, crystallized or recrystallized from water or an organic solvent, and the compound may contain the solvent molecules used. In addition, different crystallization conditions may result in different crystal forms of the compounds. Therefore, the compounds of formula I or pharmaceutically acceptable salts thereof containing different chemical amounts of crystallization solvents and all crystalline forms are within the scope of the present invention. In the present invention, when the compound of formula (I) is used to prepare a medicament, it is usually in the form of a pharmaceutical composition, which contains the compound of formula (I) and one or more pharmaceutically acceptable excipients. The pharmaceutically acceptable excipient is pharmaceutically acceptable carrier, excipient, sustained-release agent, odorant, flavor and the like. In the pharmaceutical composition, the compound of formula (I) serves as an active component, its weight accounts for 0.1 to 99.9% of the total weight of the pharmaceutical composition, and the rest is pharmaceutically acceptable excipient. The pharmaceutical composition can be prepared into a variety of dosage forms based on conventional techniques in the field of pharmaceutical preparations, such as tablets, capsules, solutions, suspensions, aerosols, dry powders, etc., and can be stored in suitable sterile utensils and delivery devices.

In the present invention, the "therapeutically effective amount" means that compared with subjects who do not receive treatment at this dose, subjects who receive treatment at this dose are cured, improved, effectively prevented in terms of lesions or side effects, or have significantly reduced incidence. In addition, it also includes doses effective to enhance normal physiological functions.

In the present invention, the compound of formula (I), the salt and pharmaceutical composition thereof can be used for humans and animals, and the administration routes include oral administration, inhalation, transdermal absorption, injection and the like. In the present invention, the preferred route is oral administration. When the compound of formula (I), the salt and pharmaceutical composition thereof are used to prepare medicament; and the dosage and frequency of administration should be determined according to medical advice.

In the present invention, the compound of formula (I), the salt and pharmaceutical composition thereof can be used in combination with other drugs when used to prevent or treat cancer and aging-related diseases, and the drugs include but are not limited to anti-tumor drugs, drugs for treating tissue fibrosis, drugs for treating osteoarthritis.

In the present invention, the "acid", "base", "oxidizing agent" and "reducing agent" have the same meanings as those familiar to those skilled in the art. The person skilled in the art may make appropriate variations and adjustments depending on the specific reaction substrates and reaction conditions.

The present invention will be further described below with examples. It should be noted that these examples are only used to illustrate the present invention and do not limit the present invention in any way. All parameters and other descriptions in the examples are based on quality unless otherwise stated. The packing used for column chromatography separation is silica gel unless otherwise specified. Experimental methods without specifying specific conditions in the following examples usually follow conventional conditions or conditions recommended by the manufacturer.

Unless otherwise defined, all technical and scientific terms used herein have the same meanings as familiar to one skilled in the art. In addition, any methods and materials similar or equivalent to those described herein can be used in the present invention. The preferred embodiments and materials described herein are for demonstrative purposes only.

Abbreviation

Bn: benzyl; DCM: dichloromethane; DIPEA: N,N-diisopropylethylamine; DMAP: 4-dimethylaminopyridine; DMF: N,N-dimethylformamide; THF: tetrahydrofuran; LDA: Lithium diisopropylamide; NaHMDS: sodium bis(trimethylsilyl)amide.

Example 1: (3R,4R)-4-(3,4-dimethoxybenzyl)-3-(4-hydroxy-3-methoxybenzyl)-3-methyldihydrofuran-2(3H)-one (A4-1a)

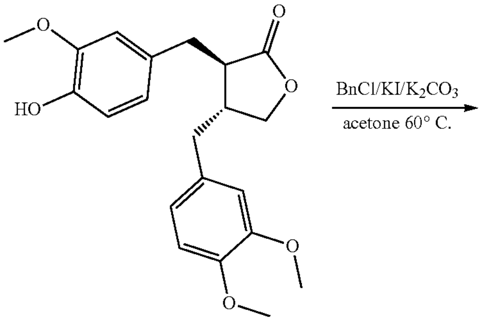

A1-1(Arctigenin)

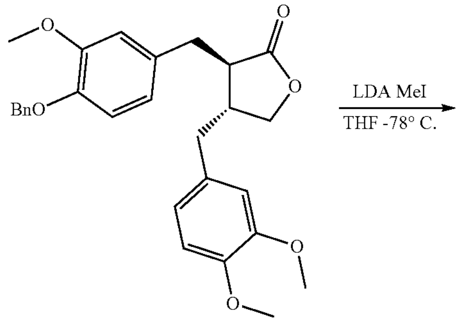

A2-1

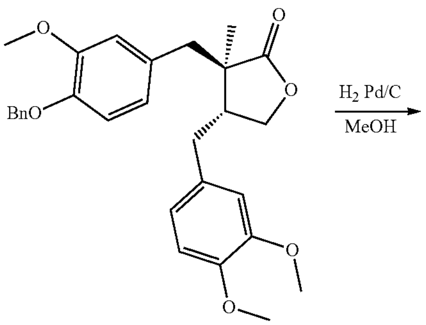

A3-1

-continued

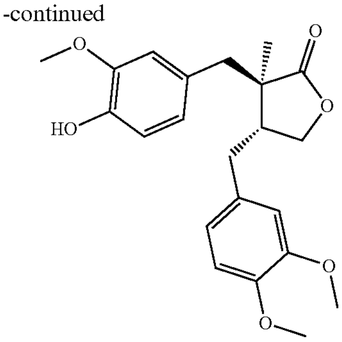

A4-1a

Synthesis of (3R,4R)-3-(4-(benzyloxy)-3-methoxybenzyl)-4-(3,4-dimethoxybenzyl)dihydrofuran-2(3H)-one (A2-1)

The commercially available raw material arctigenin A1-1 (3.72 g, 10.0 mmol) was dissolved in 60 ml of acetone, then benzyl chloride (2.3 mL, 20 mmol), potassium carbonate (2.76 g, 20 mmol) and potassium iodide (63 mg, 0.5 mmol) were added to the reaction system, heated in an oil bath at 60° C. and stirred for 6 hours. After the reaction was completed, the mixture was subjected to suction filtration, and the filtrate was concentrated under reduced pressure and subjected to silica gel column chromatography (PE:EA=1:1) to obtain 4.32 g of A2-1 as transparent oil, with a yield of 93.3%. MS m/z: 463.2 $[M+H]^+$.

Synthesis of (3R,4R)-3-(4-(benzyloxy)-3-methoxybenzyl)-4-(3,4-dimethoxybenzyl)-3-methyldihydrofuran-2 (3H)-one (A3-1)

The product A2-1 (463 mg, 1 mmol) of the previous step was dissolved in 20 ml anhydrous THF, and LDA (1 mL, 2 mmol, 2 mol/L in THF) was added dropwise at −78° C. and then stirred for 40 min. Methyl iodide (186 μL, 3 mmol in 5 ml THF) was added dropwise, stirred at −78° C. for 30 minutes and then the mixture was slowly warmed to room temperature. After the reaction was completed, the reaction was quenched with saturated ammonium chloride solution. The mixture was concentrated under reduced pressure to remove most of the tetrahydrofuran, and the residue was dissolved in 20 mL of ethyl acetate, washed with sodium chloride solution, and dried with anhydrous sodium sulfate. After suction filtration, the filtrate was concentrated under reduced pressure and subjected to silica gel column chromatography (PE:EA=1:1) to obtain 278 mg of A3-1 as transparent oil, with a yield of 58.4%. 1H NMR (500 MHZ, Chloroform-d) δ 7.46-7.41 (m, 2H), 7.38-7.33 (m, 2H), 7.31-7.27 (m, 1H), 6.81 (d, J=2.0 Hz, 2H), 6.77 (d, J=2.1 Hz, 1H), 6.71 (dd, J=8.2, 2.1 Hz, 1H), 6.67 (dd, J=8.1, 2.0 Hz, 1H), 6.63 (d, J=2.0 Hz, 1H), 5.13 (s, 2H), 4.02 (dd, J=9.0, 7.5 Hz, 1H), 3.88 (s, 3H), 3.87 (s, 3H), 3.86 (s, 3H), 3.62 (dd, J=10.2, 9.0 Hz, 1H), 2.96 (dd, J=13.6, 4.8 Hz, 1H), 2.87 (d, J=14.0 Hz, 1H), 2.79 (d, J=14.1 Hz, 1H), 2.57 (m, 1H), 1.23 (s, 3H). ESI-MS m/z: 477.2 [M+H]+.

Synthesis of (3R,4R)-4-(3,4-dimethoxybenzyl)-3-(4-hydroxy-3-methoxybenzyl)-3-methyldihydrofuran-2 (3H)-one (A4-1a)

The product A3-1 (278 mg, 0.58 mmol) of the previous step was dissolved in 10 ml of anhydrous methanol, 10% palladium on carbon (30 mg) was added, and the hydrogenation reaction was completed at 1 atmosphere for 2 hours. The catalyst was removed by filtration, and the filtrate was concentrated under reduced pressure and separated by silica gel column chromatography (PE:EA=1:1) to obtain 189 mg of A4-1a as white solid, with a yield of 84%. $^1$H NMR (500 MHZ, Chloroform-d) δ 6.84 (d, J=8.0 Hz, 1H), 6.76 (d, J=8.2 Hz, 1H), 6.74 (d, J=2.1 Hz, 1H), 6.64 (dd, J=8.0, 2.0 Hz, 1H), 6.60 (dd, J=8.1, 2.0 Hz, 1H), 6.52 (d, J=1.9 Hz, 1H), 3.94 (dd, J=9.0, 7.8 Hz, 1H), 3.84 (s, 3H), 3.84 (s, 4H), 3.83 (s, 4H), 3.82 (d, J=1.3 Hz, 1H), 3.19 (d, J=14.0 Hz, 1H), 2.73 (dd, J=13.5, 4.0 Hz, 1H), 2.62 (d, J=14.0 Hz, 1H), 2.58-2.45 (m, 1H), 2.36 (dd, J=13.6, 11.1 Hz, 1H), 1.28 (s, 3H). ESI-MS m/z: 387.2 $[M+H]^+$.

The compounds shown in Table 1 were prepared by using a synthesis method similar to that of Example 1 of the present invention and using appropriate optional starting materials.

TABLE 1

Compounds and characterization data

| Compound | Structure | $[M + H]^+$ | $^1$H NMR |
|---|---|---|---|
| A4-1b | 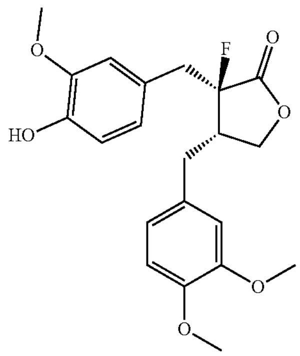 [SMILES: COc1cc(C[C@]2(F)C(=O)OC[C@@H]2Cc2ccc(OC)c(OC)c2)ccc1O] | 391.1 | $^1$H NMR (500 MHz, Chloroform-d) δ 6.90 (d, J = 8.6 Hz, 1H), 6.85 (m, 2H), 6.78 (d, J = 8.1 Hz, 1H), 6.61 (dd, J = 8.1, 2.0 Hz, 1H), 6.53 (d, J = 2.0 Hz, 1H), 4.20 (dd, J = 9.1, 6.8 Hz, 1H), 3.89(s, 3H), 3.85 (s, 3H), 3.84 (s, 3H), 3.75 (dd, J = 9.1, 6.8 Hz, 1H), 3.32 (dd, J = 19.2, 15.2 Hz, 1H), 3.20-3.04 (m, 2H), 2.91 (m, 1H), 2.54 (dd, J = 13.7, 11.7 Hz, 1H). |
| A4-1c | 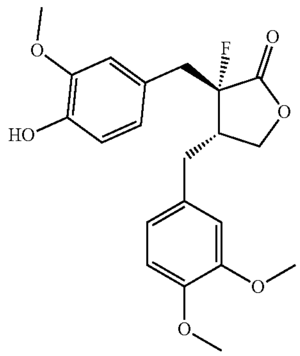 [SMILES: COc1cc(C[C@@]2(F)C(=O)OC[C@@H]2Cc2ccc(OC)c(OC)c2)ccc1O] | 391.1 | $^1$H NMR (500 MHz, Chloroform-d) δ 6.85 (d, J = 8.0 Hz, 1H), 6.79 (d, J = 8.1 Hz, 1H), 6.70 (d, J = 1.9 Hz, 1H), 6.65 (dd, J = 8.1, 2.1 Hz, 1H), 6.61 (dd, J = 8.0, 2.0 Hz, 1H), 6.57 (d, J = 2.0 Hz, 1H), 4.03 (d, J = 7.6 Hz, 2H), 3.89 (s, 3H), 3.85 (s, 3H), 3.84 (s, 3H), 3.30 (dd, J = 15.6, 13.9 Hz, 1H), 3.11 (t, J = 13.7 Hz, 1H), 2.91-2.78 (m, 1H), 2.66-2.49 (m, 2H). |
| A4-1d | 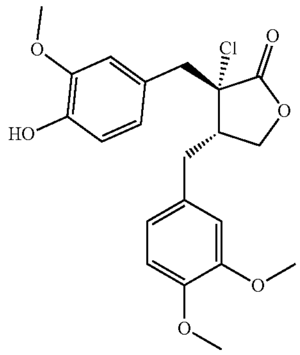 [SMILES: COc1cc(C[C@@]2(Cl)C(=O)OC[C@@H]2Cc2ccc(OC)c(OC)c2)ccc1O] | 406.1 | $^1$H NMR (500 MHz, Chloroform-d) δ 6.84 (d, J = 8.0 Hz, 1H), 6.79 (d, J = 8.1 Hz, 1H), 6.73 (d, J = 2.0 Hz, 1H), 6.67 (dd, J = 8.1, 2.1 Hz, 1H), 6.58 (m, 2H), 5.62 (s, 1H), 4.08-3.96 (m, 2H), 3.86(s, 3H), 3.85 (s, 3H), 3.83 (s, 3H), 3.65 (d, J = 14.1 Hz, 1H), 3.15 (d, J = 14.2 Hz, 1H), 2.97 (dd, J = 13.7, 4.6 Hz, 1H), 2.76-2.52 (m, 2H). |

TABLE 1-continued

Compounds and characterization data

| Compound | Structure | [M + H]+ | $^1$H NMR |
|---|---|---|---|
| A4-1e | 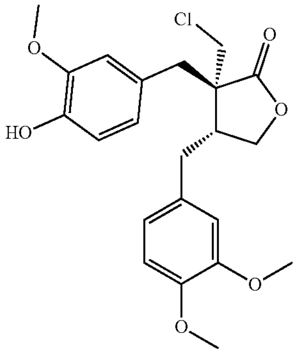 [SMILES: COc1cc(C[C@@]2(CCl)C(=O)OC[C@@H]2Cc2ccc(OC)c(OC)c2)ccc1O] | 421.1 | $^1$H NMR (400 MHz, Chloroform-d) δ 6.86 (d, J = 8.0 Hz, 1H), 6.78 (d, J = 8.1 Hz, 1H), 6.71 (d, J = 2 Hz, 1H), 6.66 m, 2H), 6.56 (d, J = 2.0 Hz, 1H), 5.59 (s, 1H), 4.06 (dd, J = 9.0, 7.6 Hz, 1H), 3.93 (dd, J = 9.0, 7.6 Hz, 1H), 3.86 (m, 9H), 3.77 (d, J = 5.7 Hz, 2H), 3.14 (d, J = 13.9 Hz, 1H), 2.89 (dd, J = 12.5, 3.4 Hz, 1H), 2.75 (d, J = 13.9 Hz, 1H), 2.69 (m, 1H), 2.65 (d, J = 12.1 Hz, 1H). |
| A4-1f | 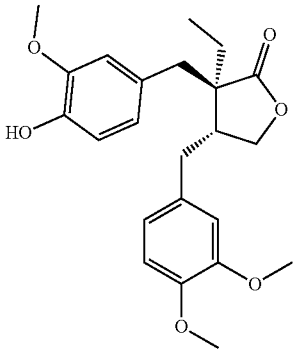 [SMILES: CC[C@]1(Cc2ccc(O)c(OC)c2)C(=O)OC[C@@H]1Cc1ccc(OC)c(OC)c1] | 401.2 | $^1$H NMR (400 MHz, Chloroform-d) δ 6.85 (d, J = 8.0 Hz, 1H), 6.75 (dd, J = 5.1, 3.1 Hz, 2H), 6.67 (dd, J = 8.0, 2.0 Hz, 1H), 6.58 (dd, J = 8.1, 2.1 Hz, 1H), 6.48 (d, J = 2.0 Hz, 1H), 5.58 (s, 1H), 3.92-3.86 (m, 2H), 3.84 (s, 6H), 3.83 (s, 3H), 3.32 (d, J = 14.0 Hz, 1H), 2.74 (dd, J = 13.2, 3.6 Hz, 1H), 2.61-2.49 (m, 2H), 2.42 (dd, J = 13.3, 11.5 Hz, 1H), 1.81 (dq, J = 14.8, 7.5 Hz, 1H), 1.70 (dq, J = 14.8, 7.5 Hz, 1H), 1.13 (t, J = 7.5 Hz, 3H). |
| A4-1g | 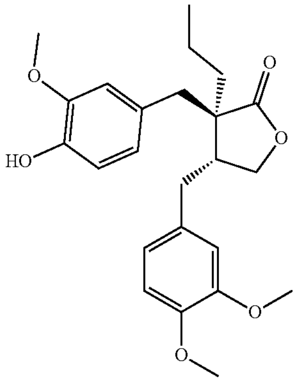 [SMILES: CCC[C@]1(Cc2ccc(O)c(OC)c2)C(=O)OC[C@@H]1Cc1ccc(OC)c(OC)c1] | 415.2 | $^1$H NMR (500 MHz, Chloroform-d) δ 6.85 (d, J = 8.0 Hz, 1H), 6.79-6.72 (m, 2H), 6.67 (dd, J = 8.0, 2.0 Hz, 1H), 6.58 (dd, J = 8.2, 2.1 Hz, 1H), 6.49 (d, J = 2.0 Hz, 1H), 5.65 (s, 1H), 3.89-3.86 (m, 1H), 3.83 (s, 4H), 3.83 (s, 3H), 3.82 (s, 3H), 3.31 (d, J = 14.0 Hz, 1H), 2.74 (dd, J = 13.4, 3.6 Hz, 1H), 2.60 (d, J = 14.0 Hz, 1H), 2.57-2.49 (m, 1H), 2.42 (dd, J = 13.4, 11.5 Hz, 1H), 1.73-1.50 (m, 4H), 1.05-0.98 (m, 3H). |
| A4-1i | 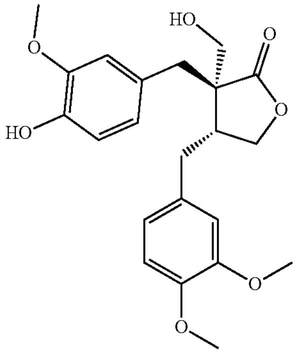 [SMILES: COc1cc(C[C@@]2(CO)C(=O)OC[C@@H]2Cc2ccc(OC)c(OC)c2)ccc1O] | 403.1 | $^1$H NMR (400 MHz, Chloroform-d) δ 6.86 (d, J = 7.9 Hz, 1H), 6.77 (d, J = 8.2 Hz, 1H), 6.72 (d, J = 2.0 Hz, 1H), 6.64 (td, J = 7.9, 2.0 Hz, 2H), 6.55 (d, J = 2.1 Hz, 1H), 5.65 (s, 1H), 4.05 (dd, J = 8Hz, 1H), 3.98-3.90 (m, 3H), 3.85 (s, 6H), 3.84 (s, 3H), 3.04 (d, J = 13.9 Hz, 1H), 2.76 (t, J = 9.6 Hz, 1H), 2.70-2.63 (m, 2H), 2.59 (d, J = 14.0 Hz, 1H). |

TABLE 1-continued

| Compounds and characterization data | | | |
|---|---|---|---|
| Compound | Structure | [M + H]+ | 1H NMR |
| A4-1j | 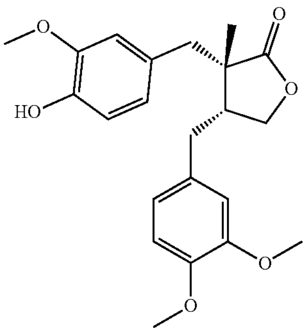 | 387.2 | $^1$H NMR (500 MHz, Chloroform-d) δ 6.88 (d, J = 7.9 Hz, 1H), 6.83 (d, J = 8.2 Hz, 1H), 6.77 (dd, J = 8.0, 2.1 Hz, 1H), 6.74 (d, J = 2.0 Hz, 1H), 6.71 (dd, J = 8.1, 2.0 Hz, 1H), 6.66 (d, J = 2.1 Hz, 1H), 5.63 (s, 1H), 4.05 (dd, J = 9.0, 7.6 Hz, 1H), 3.90 (s, 6H), 3.90 (s, 3H), 3.66 (dd, J = 10.3, 8.9 Hz, 1H), 2.99 (dd, J = 13.6, 4.9 Hz, 1H), 2.91 (d, J = 14.0 Hz, 1H), 2.82 (d, J = 6.0 Hz, 1H), 2.81-2.76 (m, 1H), 2.61 (tdd, J = 10.6, 7.6, 4.9 Hz, 1H), 1.26 (s, 3H). |
| A4-1k | 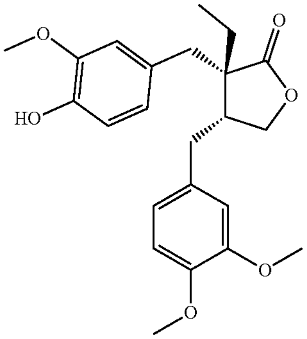 | 401.2 | $^1$H NMR (500 MHz, Chloroform-d) δ 6.88 (d, J = 7.9 Hz, 1H), 6.83 (d, J = 8.1 Hz, 1H), 6.80-6.75 (m, 2H), 6.70 (dd, J = 8.1, 2.1 Hz, 1H), 6.65 (d, J = 2.0 Hz, 1H), 5.61 (s, 1H), 4.07-4.02 (m, 1H), 3.90 (s, 3H), 3.90 (s, 3H), 3.89 (s, 3H), 3.58 (dd, J = 10.2, 8.8 Hz, 1H), 2.99-2.91 (m, 2H), 2.87-2.77 (m, 3H), 1.82 (dq, J = 14.8, 7.4 Hz, 1H), 1.55 (dq, J = 14.7, 7.4 Hz, 1H), 0.96 (t, J = 7.4 Hz, 3H). |
| A4-1l | 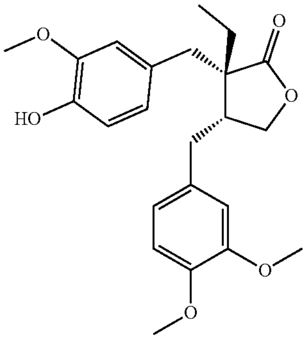 | 415.2 | $^1$H NMR (500 MHz, Chloroform-d) δ 6.85 (d, J = 8.0 Hz, 1H), 6.80 (d, J = 8.1 Hz, 1H), 6.77-6.72 (m, 2H), 6.67 (dd, J = 8.1, 2.1 Hz, 1H), 6.62 (d, J = 2.0 Hz, 1H), 5.59 (s, 1H), 4.03-3.97 (m, 1H), 3.87 (s, 6H), 3.87 (s, 3H), 3.58-3.52 (m, 1H), 2.97-2.82 (m, 3H), 2.81-2.75 (m, 2H), 1.52-1.38 (m, 2H), 1.34-1.22 (m, 2H), 0.92 (t, J = 7.1 Hz, 3H). |

Example 2: (3R,4R)-4-(3,4-dimethoxybenzyl)-3-(4-hydroxy-3-phenylethoxybenzyl)dihydrofuran-2(3H)-one (B9-1a)

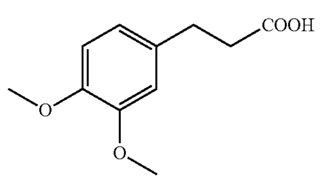

B1-1

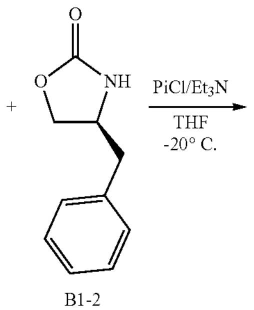

B1-2

-continued

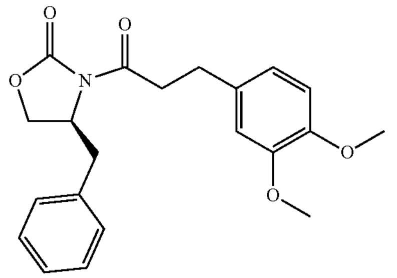

B2-1

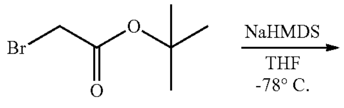

B2-2

-continued
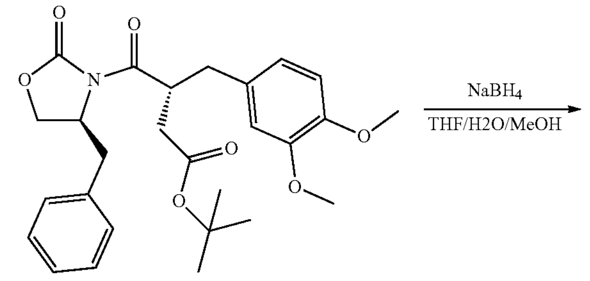
B3-1
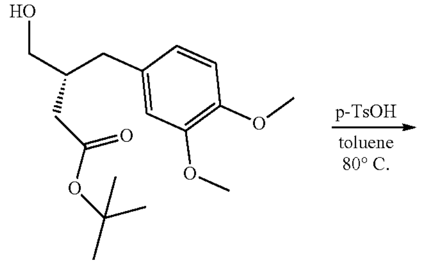
B4-1
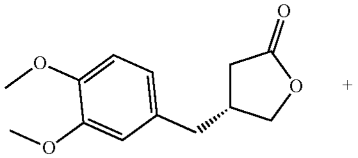
B5-1
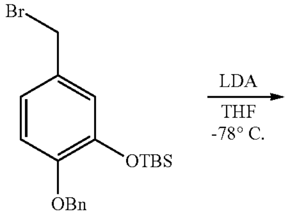
B5-2e
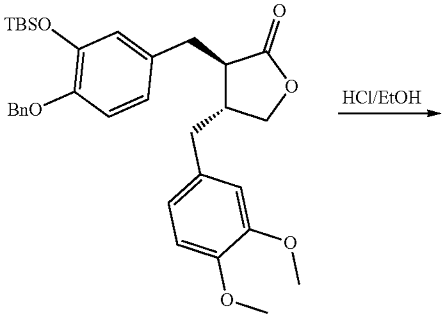
B6-1
-continued
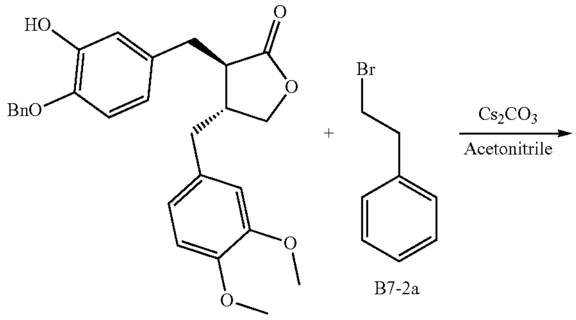
B7-1 B7-2a
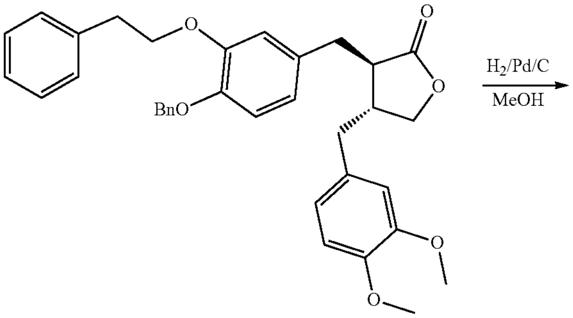
B8-1a
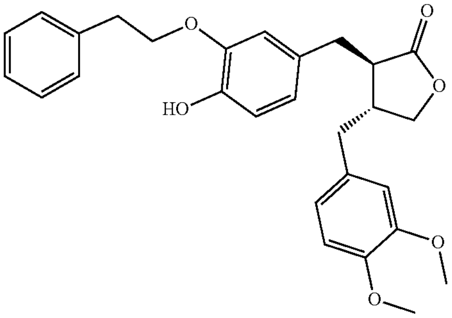
B9-1a
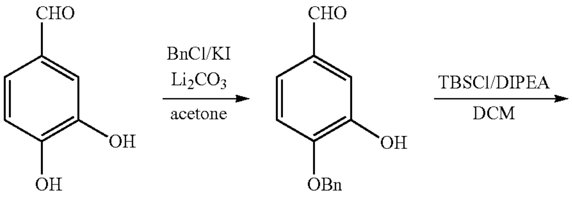
B5-2a B5-2b
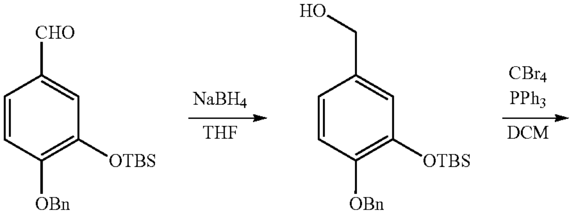
B5-2c B5-2d -continued

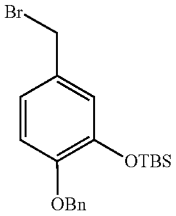

B5-2e (S)-4-benzyl-3-(3-(3,4-dimethoxyphenyl) propionyl)-2-oxazolidinone (B2-1)

3,4-dimethoxyphenylpropionic acid (B1-1) (10.50 g, 50.0 mmol) was dissolved in 300 mL anhydrous THF, and pivaloyl chloride (6.0 mL, 50.0 mmol) and triethylamine (21.0 mL, 150.0 mmol) were added dropwise at −20° C. and then stirred at −20° C. for 1 h. A solution of(S)-4-benzyl-2-oxazolidinone (B1-2) (8.0 g, 45.0 mmol) in THF (100 mL) was added dropwise, and anhydrous LiCl (2.10 g, 50.0 mmol) was added in one batch and then stirred for 1 hour. Then the mixture was warmed to room temperature, and then stirred for 4 hours. The reaction solution was concentrated under reduced pressure to about 50 mL, diluted with 100 mL of ethyl acetate, washed with 10% sodium bicarbonate, 5% potassium bisulfate, and saturated sodium chloride solution, and dried over anhydrous sodium sulfate. After suction filtration, the filtrate was concentrated under reduced pressure to obtain 15.8 g of B2-1 as white solid, which was directly used in the next reaction without purification. 1H NMR (400 MHZ, Chloroform-d) δ 7.35-7.27 (m, 3H), 7.20-7.13 (m, 2H), 6.81 (dd, J=3.4, 1.7 Hz, 3H), 4.66 (ddt, J=9.4, 6.9, 3.5 Hz, 1H), 4.22-4.03 (m, 2H), 3.88 (s, 3H), 3.85 (s, 3H), 3.36-3.17 (m, 3H), 3.05-2.89 (m, 2H), 2.75 (dd, J=13.4, 9.5 Hz, 1H). ESI-MS m/z: 370.2 $[M+H]^+$.

(S)-4-benzyl-3-[(R)-2-tert-butyl acetate-3-(3,4-dimethoxyphenyl) propionyl]-2-oxazolidinone (B3-1)

The product B2-1 (15.8 g, 43 mmol) in the previous step was dissolved in 500 mL anhydrous THF, and NaHMDS (32 mL, 64 mmol, 2 mol/L in THF) was added dropwise at −78° C. and then stirred for 1 hour. Tert-butyl bromoacetate (12.6 mL, 85 mmol) was added dropwise, and stirred at this temperature for 5 hours. The reaction was quenched with saturated ammonium chloride solution, and most of the tetrahydrofuran was removed by concentration under reduced pressure. The residue was dissolved in 100 mL of ethyl acetate, washed with 5% potassium hydrogen sulfate and saturated sodium chloride solution in sequence, and dried over anhydrous sodium sulfate. After suction filtration, the filtrate was concentrated under reduced pressure and subjected to silica gel column chromatography (PE:EA=4:1) to obtain 28.6 g of B3-1 as white solid. The two-step yield was 59.2%. 1H NMR (400 MHZ, Chloroform-d) δ 7.35-7.31 (m, 2H), 7.27 (s, 3H), 6.87 (s, 1H), 6.76 (d, J=1.5 Hz, 2H), 4.60-4.50 (m, 1H), 4.45 (ddd, J=10.1, 8.4, 5.0 Hz, 1H), 4.12 (d, J=7.1 Hz, 1H), 4.10-4.06 (m, 1H), 3.97 (t, J=8.4 Hz, 1H), 3.89 (s, 3H), 3.85 (s, 3H), 3.35-3.26 (m, 1H), 2.96 (dd, J=13.1, 6.0 Hz, 1H), 2.85-2.75 (m, 1H), 2.78-2.70 (m, 1H), 2.56 (dd, J=13.2, 9.3 Hz, 1H), 2.38 (dd, J=16.9, 4.0 Hz, 1H), 1.46 (d, J=1.8 Hz, 1H), 1.40 (s, 9H). ESI-MS m/z: 484.2 $[M+H]^+$.

Tert-butyl (R)-3-hydroxymethyl-4-(3,4-dimethoxyphenyl)-butyrate (B4-1)

The product B3-1 (2.50 g, 5.2 mmol) from the previous step was dissolved in 80 mL of tetrahydrofuran, 20 mL of water was added, and sodium borohydride (0.29 g, 5.8 mmol) was added in batches, and stirred at room temperature for 2 hours. The mixture was concentrated under reduced pressure to remove most of the tetrahydrofuran, diluted with ethyl acetate, and 1 mol/L hydrochloric acid was slowly added dropwise until no bubbles were generated. The mixture was washed with 5% potassium hydrogen sulfate and saturated sodium chloride in sequence, and dried with anhydrous sodium sulfate. After suction filtration, the filtrate was concentrated under reduced pressure to obtain 1.52 g of colorless and transparent liquid B4-1. It can be used directly in the next reaction without purification. 1H NMR (400 MHZ, Chloroform-d) δ 6.83-6.69 (m, 3H), 3.87 (s, 3H), 3.85 (s, 3H), 2.65 (dd, J=13.6, 6.1 Hz, 1H), 2.55 (dd, J=14.0, 5.9 Hz, 1H), 2.35-2.19 (m, 3H), 2.01 (dd, J=14.3, 8.7 Hz, 1H), 1.45 (s, 9H). ESI-MS m/z: 311.2 $[M+H]^+$.

(R)-4-(3,4-dimethoxybenzyl)-butyrolactone (B5-1)

The product B4-1 (1.50 g, 4.8 mmol) from the previous step was dissolved in 20 ml of toluene, and p-toluenesulfonic acid (41.6 mg, 0.24 mmol) was added and stirred at 80° C. for 1 hour. The mixture was concentrated under reduced pressure to remove toluene. The residue was dissolved in ethyl acetate, washed with 10% sodium bicarbonate and saturated sodium chloride solution in sequence, dried over anhydrous sodium sulfate, and subjected to silica gel column chromatography (V (petroleum ether):V (ethyl acetate)=3:1), and 1.14 g of colorless and transparent oil B5-1 was obtained. 1H NMR (400 MHZ, Chloroform-d) δ 6.81 (d, J=8.1 Hz, 1H), 6.70 (dd, J=8.1, 2.0 Hz, 1H), 6.66 (d, J=2.0 Hz, 1H), 4.34 (dd, J=9.1, 6.9 Hz, 1H), 4.04 (dd, J=9.1, 6.0 Hz, 1H), 3.88 (s, 3H), 3.87 (s, 3H), 2.89-2.78 (m, 1H), 2.72 (dd, J=7.7, 4.1 Hz, 2H), 2.61 (dd, J=17.5, 8.1 Hz, 1H), 2.29 (dd, J=17.5, 6.9 Hz, 1H). ESI-MS m/z: 237.1 $[M+H]^+$.

Synthesis of 4-(benzyloxy)-3-hydroxybenzaldehyde (B5-2b)

The commercially available raw material B5-2a (1.38 g, 10 mmol) was dissolved in 20 ml of acetone, lithium carbonate (888 mg, 12 mmol), benzyl chloride (1.37 ml, 12 mmol), and potassium iodide (83 mg, 0.5 mmol) were added, heated and stirred in a 60° C. oil bath for 6 hours. After the reaction was completed, lithium carbonate was removed by suction filtration. The filtrate was distilled under reduced pressure and separated by silica gel column chromatography (PE:EA=3:1) to obtain 1.82 g of white solid B5-2b with a yield of 79.8%. 1H NMR (500 MHz, Chloroform-d) δ 9.84 (s, 1H), 7.46 (d, J=2.0 Hz, 1H), 7.43 (m, 4H), 7.41-7.38 (m, 2H), 7.04 (d, J=8.2 Hz, 1H), 5.21 (s, 2H). MS m/z: 229.1 $[M+H]^+$.

Synthesis of 4-(benzyloxy)-3-((tert-butyldimethylsilyl)oxy)benzaldehyde (B5-2c)

The product B5-2b (1.14 g, 5 mmol) from the previous step was dissolved in 20 ml of dichloromethane, and N,N-diisopropylethylamine (2.6 ml, 15 mmol) and tert-butyl dimethylchlorosilane (1.5 g, 10 mmol) were added under ice bath and stirred in ice bath for 30 minutes, then warmed to room temperature and stirred. After the reaction was completed, the reaction solution was concentrated under reduced pressure and separated by silica gel column chromatography (PE:EA=5:1) to obtain 1.56 g of white solid B5-2c, with a yield of 91.2%. 1H NMR (500 MHZ, Chloroform-d) δ 9.70 (s, 1H), 7.30-7.34 (m, 3H), 7.29-7.20 (m, 4H), 6.90 (d, J=8.3 Hz, 1H), 5.01 (s, 2H), 0.84 (s, 9H). MS m/z: 343.2 $[M+H]^+$.

Synthesis of (4-(benzyloxy)-3-((tert-butyldimethylsilyl)oxy)phenyl) methanol (B5-2d)

The product B5-2c (1.03 g, 3 mmol) of the previous step was dissolved in 10 ml of tetrahydrofuran, sodium borohydride (228 mg, 6 mmol) was added in batches in the greenhouse, and stirred for 3 hours in the greenhouse. After the reaction was completed, the mixture was separated by silica gel column chromatography (PE:EA=3:1) to obtain 986 mg of white solid B5-2d with a yield of 95.5%, 1H NMR (600 MHZ, Chloroform-d) δ 7.35-7.29 (m, 2H), 7.28-7.23 (m, 2H), 7.22-7.19 (m, 1H), 6.78 (d, J=1.5 Hz, 1H), 6.76 (d, J=1.9 Hz, 2H), 4.93 (s, 2H), 4.44 (s, 2H), 0.85 (s, 9H). MS m/z: 345.2 $[M+H]^+$.

Synthesis of (2-(benzyloxy)-5-(bromomethyl) phenoxy) (tert-butyl)dimethylsilane (B5-2e)

Triphenylphosphine (688 mg, 3 mmol) and carbon tetrabromide (996 mg, 3 mmol) were dissolved in 5 ml of dichloromethane. After stirring at room temperature for 5 minutes, a solution of B5-2d (688 mg, 2 mmol) in dichloromethane (5 ml) was added dropwise to the reaction system, stirred in the greenhouse for 4 hours. After the reaction was completed, the reaction solution was concentrated under reduced pressure and separated by silica gel column chromatography (PE:EA=5:1) to obtain 952 mg of oil B5-2e, with a yield of 78.1%. 1H NMR (500 MHz, Chloroform-d) δ 7.47-7.44 (m, 2H), 7.43-7.38 (m, 2H), 7.38-7.34 (m, 1H), 6.94 (d, J=1.4 Hz, 1H), 6.92 (d, J=2.2 Hz, 1H), 6.90-6.87 (m, 1H), 5.08 (s, 2H), 4.54 (s, 2H), 1.00 (s, 9H). MS m/z: 407.1 $[M+H]^+$.

Synthesis of (3R,4R)-3-(4-(benzyloxy)-3-((tert-butyldimethylsilyl)oxy)benzyl)-4-(3,4-dimethoxybenzyl)dihydrofuran-2 (3H)-one (B6-1)

A solution of the product B5-1 (400.0 mg, 1.7 mmol) from the previous step in 10 mL of tetrahydrofuran was added dropwise with LDA (1.7 mL, 3.4 mmol, 2 mol/L in THF) at −78° C. The solution was stirred for 40 min and a solution of compound B5-2e (690.2 mg, 1.7 mmol) in 5 mL of tetrahydrofuran was added dropwise and stirred for 4 h. The reaction was quenched by saturated ammonium chloride and concentrated under reduced pressure to remove most of the tetrahydrofuran. The residue was dissolved in ethyl acetate, washed with 5% potassium bisulfate and saturated sodium chloride, dried over anhydrous sodium sulfate, and separated by a silica gel column (V (petroleum ether):V (ethyl acetate) =3:1). 614 mg of colorless viscous liquid B6-1 was obtained, and the yield was 64.3%. MS m/z: 563.3 $[M+H]^+$.

Synthesis of (3R,4R)-3-(4-(benzyloxy)-3-hydroxybenzyl)-4-(3,4-dimethoxybenzyl)dihydrofuran-2 (3H)-one (B7-1)

The product B6-1 (300.0 mg, 0.53 mmol) was dissolved in 5 ml of hydrochloric acid/ethanol (2 mol/L) solution, stirred at room temperature for 2 h. After the reaction was completed, most of the solvent was removed by distillation under reduced pressure, and the residue was separated by a silica gel column (V (petroleum ether):V (ethyl acetate)=3:1) to obtain 165 mg of a colorless viscous liquid B7-1, with a yield of 73.6%. MS m/z: 449.2 $[M+H]^+$.

Synthesis of (3R,4R)-3-(4-(benzyloxy)-3-phenylethoxybenzyl)-4-(3,4-dimethoxybenzyl)dihydrofuran-2 (3H)-one (B8-1a)

The product B7-1 (165 mg, 0.37 mmol) was dissolved in 5 mL of acetonitrile, and cesium carbonate (240 mg, 0.74 mmol) and the commercially available compound B7-2a (272 mg, 1.48 mmol) were added at room temperature and stirred in an oil bath at 80° C. for 2 h. After the reaction was completed, the mixture was subjected to suction filtration to remove cesium carbonate. The filtrate was distilled under reduced pressure, and then separated by silica gel column chromatography (V (petroleum ether):V (ethyl acetate)=3:1) to obtain 195 mg of B8-1a as oil, with a yield of 95.5%. MS m/z: 553.2 $[M+H]^+$.

(3R,4R)-4-(3,4-dimethoxybenzyl)-3-(4-hydroxy-3-phenylethoxybenzyl)dihydrofuran-2 (3H)-one (B9-1a)

The product of the previous step, B8-1a (195 mg, 0.35 mmol), was dissolved in 10 ml of anhydrous methanol, 10% palladium carbon (20 mg) was added, and the reaction was completed by hydrogenation at 1 atm for 2 h. The catalyst was removed by filtration and the filtrate was concentrated under reduced pressure and separated by silica gel column chromatography (PE:EA=2:1) to obtain 136 mg of white solid B9-1a with a yield of 84.1%. 1H NMR (500 MHZ, Chloroform-d) & 7.33 (t, J=7.6 Hz, 2H), 7.29-7.24 (m, 3H), 6.81 (dd, J=8.3, 2.8 Hz, 1H), 6.73 (dd, J=9.5, 4.0 Hz, 1H), 6.67 (d, J=1.9 Hz, 1H), 6.60 (dd, J=8.1, 2.0 Hz, 1H), 6.54 (dd, J=8.1, 2.0 Hz, 1H), 6.47 (d, J=2.0 Hz, 1H), 4.22-4.17 (m, 2H), 4.10 (dd, J=8.9, 7.0 Hz, 1H), 3.87 (dd, J=7.5, 8.4 Hz, 1H), 3.84 (s, 3H), 3.80 (s, 3H), 3.10 (q, J=7.6, 6.8 Hz, 2H), 2.90 (t, J=4.2 Hz, 2H), 2.64 (dd, J=13.1, 5.6 Hz, 1H), 2.59-2.42 (m, 2H). MS m/z: 463.2 $[M+H]^+$.

The compounds shown in Table 2 were prepared by using a synthesis method similar to that of Example 2 of the present invention and using appropriate optional starting materials.

TABLE 2

| Compounds and characterization data | | | |
|---|---|---|---|
| Compound | Structure | $[M + H]^+$ | $^1$H NMR |
| B9-1d | 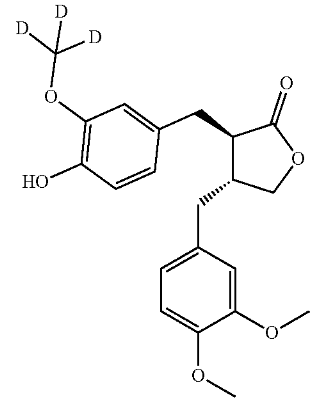 [SMILES: [2H]C([2H])([2H])Oc1cc(C[C@H]2C(=O)OC[C@@H]2Cc2ccc(OC)c(OC)c2)ccc1O] | 375.2 | $^1$H NMR (500 MHz, Chloroform-d) δ 6.82 (d, J = 8.0 Hz, 1H), 6.75 (d, J = 8.0 Hz, 1H), 6.63 (d, J = 2.0 Hz, 1H), 6.61 (dd, J = 7.9, 2.0 Hz, 1H), 6.55 (dd, J = 8.1, 2.0 Hz, 1H), 6.46 (d, J = 2.0 Hz, 1H), 4.14 (dd, J = 9.1, 7.2 Hz, 1H), 3.88 (dd, J = 9.1, 7.3 Hz, 1H), 3.85 (s, 4H), 3.81 (s, 3H), 2.93 (dd, J = 10.1, 6.0 Hz, 2H), 2.64 (dd, J = 13.3, 6.1 Hz, 1H), 2.59-2.45 (m, 3H). |
| B9-1e | 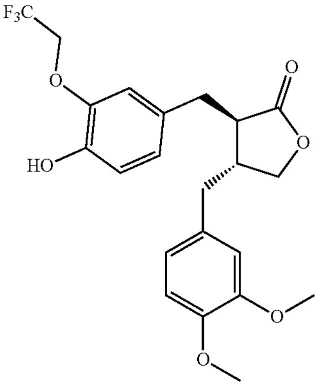 [SMILES: COc1ccc(C[C@H]2COC(=O)[C@@H]2Cc2ccc(O)c(OCC(F)(F)F)c2)cc1OC] | 441.4 | $^1$H NMR (500 MHz, Chloroform-d) δ 6.87 (d, J = 8.1 Hz, 1H), 6.79-6.75 (m, 1H), 6.69 (dd, J = 8.1, 2.0 Hz, 1H), 6.64 (d, J = 2.0 Hz, 1H), 6.60-6.56 (m, 1H), 6.50 (d, J = 2.0 Hz, 1H), 4.34 (qd, J = 8.1, 1.7 Hz, 2H), 4.18-4.12 (m, 1H), 3.92-3.86 (m, 1H), 3.86 (s, 3H), 3.82 (s, 4H), 2.94 (dd, J = 14.2, 6.5 Hz, 1H), 2.87 (dd, J = 14.2, 5.4 Hz, 1H), 2.67 (dd, J = 13.8, 6.8 Hz, 1H), 2.61-2.54 (m, 2H), 2.51-2.42 (m, 1H). |
| B9-1f | 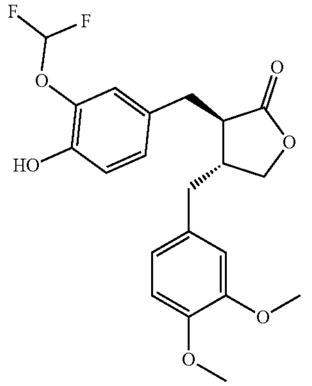 [SMILES: COc1ccc(C[C@H]2COC(=O)[C@@H]2Cc2ccc(O)c(OC(F)F)c2)cc1OC] | 408.3 | $^1$H NMR (500 MHz, Chloroform-d) δ 6.94-6.85 (m, 3H), 6.77 (d, J = 8.1 Hz, 1H), 6.58 (dd, J = 8.1, 2.1 Hz, 1H), 6.51(t, J = 56 Hz, 1H), 6.49 (d, J = 2.0 Hz, 1H), 5.82 (s, 1H), 4.16 (dd, J = 9.2, 7.4 Hz, 1H), 3.89 (dd, J = 9.2, 7.8 Hz, 1H), 3.85(s, 3H), 3.84(s, 3H), 2.96-2.83 (m, 2H), 2.68-2.39 (m, 4H). |
| B9-1i | 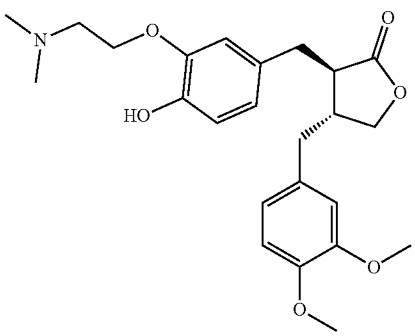 | 430.2 | $^1$H NMR (500 MHz, Chloroform-d) δ 6.77 (d, J = 7.9 Hz, 1H), 6.72 (d, J = 8.2 Hz, 1H), 6.66-6.57 (m, 2H), 6.57-6.49 (m, 1H), 6.46 (d, J = 2.1 Hz, 1H), 4.11-4.06 (m, 1H), 4.02 (t, J = 5.1 Hz, 2H), 3.96-3.82 (m, 9H), 3.82-3.75 (m, 8H), 3.01-2.90 (m, 2H), 2.84 (dd, J = 5.3 Hz, 1H), 2.57 (s, 6H), 2.53-2.39 (m, 3H). |

TABLE 2-continued

| Compounds and characterization data | | | |
|---|---|---|---|
| Compound | Structure | $[M + H]^+$ | $^1H$ NMR |
| B9-1j | 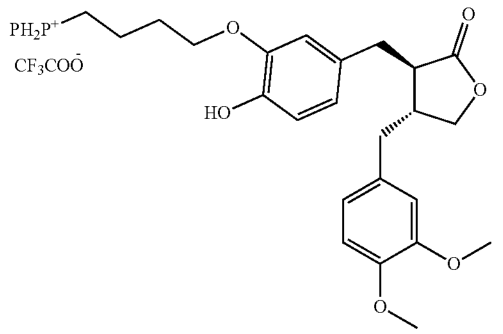 | 789.2 | $^1H$ NMR (500 MHz, Chloroform-d) δ 7.81-7.62 (m, 15H), 6.90 (d, J = 8.0 Hz, 1H), 6.75 (d, J = 8.1 Hz, 1H), 6.63-6.53 (m, 3H), 6.49 (d, J = 2.0 Hz, 1H), 4.07 (dd, J = 9.1, 6.8 Hz, 1H), 4.00 (t, J = 4Hz, 2H), 3.87-3.84 (m, 1H), 3.83 (s, 3H), 3.79 (s, 3H), 2.87 (d, J = 5.7 Hz, 2H), 2.68-2.61 (m, 1H), 2.57-2.44 (m, 3H), 1.84 (t, J = 4Hz, 2H), 1.38-1.20 (m, 4H). |
| B9-1k | 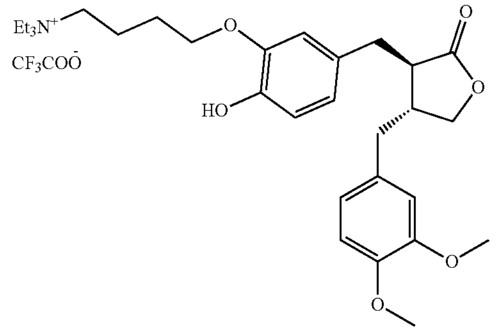 | 628.3 | $^1H$ NMR (500 MHz, Chloroform-d) δ 6.86 (d, J = 7.9 Hz, 1H), 6.76 (d, J = 8.1 Hz, 1H), 6.67-6.63 (m, 1H), 6.57 (m, 2H), 6.51 (d, J = 2.0 Hz, 1H), 4.07 (dd, J = 9.0, 6.9 Hz, 1H), 3.85 (dd, J = 9.0, 6.9 Hz, 1H), 3.83 (s, 3H), 3.82 (s, 2H), 3.32 (s, 2H), 3.28-3.12 (m, 6H), 2.86 (qd, J = 14.2, 5.9 Hz, 2H), 2.64 (dd, J = 12.9, 5.3 Hz, 1H), 2.59-2.43 (m, 3H), 1.83 (m, 4H), 1.24 (s, 9H). |
| B9-1m | 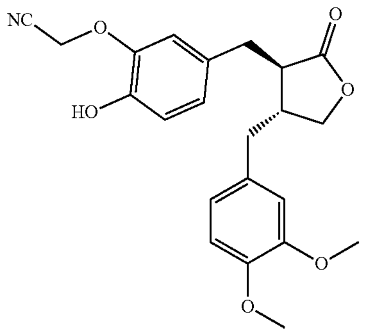 [SMILES: COc1ccc(C[C@H]2COC(=O)[C@@H]2Cc2ccc(O)c(OCC#N)c2)cc1OC] | 398.2 | $^1H$ NMR (500 MHz, Chloroform-d) δ 6.87 (dt, J = 8.1, 0.8 Hz, 1H), 6.78 (d, J = 8.1 Hz, 1H), 6.72 (m, 2H), 6.60 (dd, J = 8.1, 2.0 Hz, 1H), 6.50 (d, J = 2.0 Hz, 1H), 4.77 (d, J = 4.1 Hz, 2H), 4.16 (dd, J = 9.1, 7.5 Hz, 1H), 3.89 (dd, J = 9.2, 7.8 Hz, 1H), 3.86 (s, 3H), 3.82 (s, 3H), 2.91 (dd, J = 6.0, 1.9 Hz, 2H), 2.69-2.55 (m, 3H), 2.52-2.45 (m, 1H). |
| B9-1n | 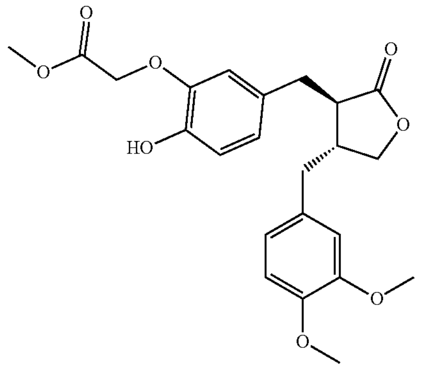 | 431.2 | $^1H$ NMR (500 MHz, Chloroform-d) δ 6.89 (d, J = 8.2 Hz, 1H), 6.79 (d, J = 8.1 Hz, 1H), 6.71 (dd, J = 8.1, 2.0 Hz, 1H), 6.66 (d, J = 2.0 Hz, 1H), 6.59 (dd, J = 8.1, 2.0 Hz, 1H), 6.51 (d, J = 2.0 Hz, 1H), 4.61 (d, J = 4.7 Hz, 2H), 4.14 (dd, J = 9.1, 7.4 Hz, 1H), 3.92-3.88 (m, 1H), 3.87 (s, 3H), 3.85 (s, 3H), 3.83 (s, 3H), 2.91 (t, J = 6.1 Hz, 2H), 2.67 (dd, J = 13.7, 6.4 Hz, 1H), 2.61-2.53 (m, 2H), 2.52-2.44 (m, 1H). |

TABLE 2-continued

| Compounds and characterization data | | | |
|---|---|---|---|
| Compound | Structure | $[M + H]^+$ | $^1H$ NMR |
| B9-1o | 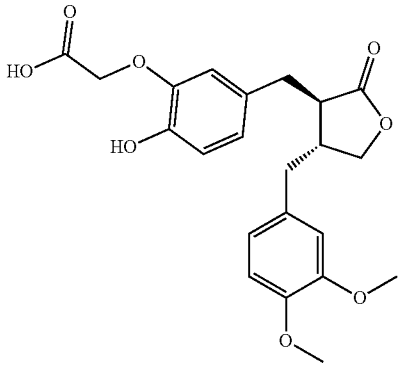 [SMILES: COc1ccc(C[C@H]2COC(=O)[C@@H]2Cc2ccc(O)c(OCC(=O)O)c2)cc1OC] | 417.1 | $^1H$ NMR (500 MHz, Chloroform-d) δ 6.87 (d, J = 8.1 Hz, 1H), 6.78 (d, J = 8.1 Hz, 1H), 6.67 (d, J = 8.1 Hz, 1H), 6.59 (dd, J = 8.4, 1.9 Hz, 2H), 6.50 (d, J = 2.0 Hz, 1H), 4.59 (s, 2H), 4.17 (dd, J = 9.2, 7.4 Hz, 1H), 3.94-3.89 (m, 1H), 3.86 (s, 3H), 3.83 (s, 3H), 2.90-2.87 (m, 2H), 2.68-2.55 (m, 3H), 2.48 (h, J = 7.5 Hz, 1H). |
| B9-1p | 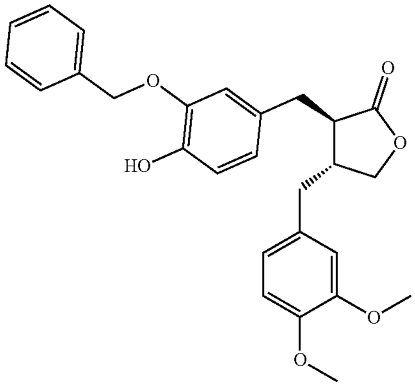 [SMILES: COc1ccc(C[C@H]2COC(=O)[C@@H]2Cc2ccc(O)c(OCc3ccccc3)c2)cc1OC] | 449.2 | $^1H$ NMR (500 MHz, Chloroform-d) δ 7.45-7.35 (m, 5H), 6.84 (d, J = 8.0 Hz, 1H), 6.76-6.72 (m, 2H), 6.62 (dd, J = 8.1, 2.0 Hz, 1H), 6.54 (dd, J = 8.1, 2.0 Hz, 1H), 6.46 (d, J = 2.0 Hz, 1H), 5.03 (s, 2H), 4.16-4.07 (m, 2H), 3.83 (s, 3H), 3.81 (s, 3H), 2.96-2.88 (m, 2H), 2.65-2.41 (m, 4H). |
| B9-1q | 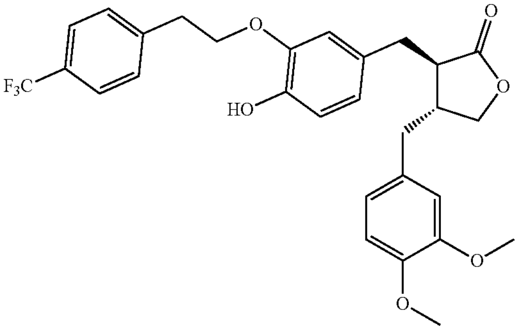 [SMILES: COc1ccc(C[C@H]2COC(=O)[C@@H]2Cc2ccc(O)c(OCCc3ccc(C(F)(F)F)cc3)c2)cc1OC] | 531.2 | $^1H$ NMR (500 MHz, Chloroform-d) δ 7.59 (d, J = 8.0 Hz, 2H), 7.38 (d, J = 8.0 Hz, 2H), 6.81 (d, J = 8.0 Hz, 1H), 6.74 (d, J = 8.1 Hz, 1H), 6.67 (d, J = 2.0 Hz, 1H), 6.60 (dd, J = 8.1, 2.0 Hz, 1H), 6.56 (dd, J = 8.1, 2.0 Hz, 1H), 6.48 (d, J = 2.0 Hz, 1H), 4.21 (t, J = 6.7 Hz, 2H), 4.14-4.08 (m, 1H), 3.89-3.85 (m, 1H), 3.84 (s, 3H), 3.81 (s, 3H), 3.15 (t, J = 6.7 Hz, 2H), 2.98-2.82 (m, 2H), 2.66 (dd, J = 13.7, 6.3 Hz, 1H), 2.60-2.51 (m, 2H), 2.51-2.43 (m, 1H). |
| B9-1r | 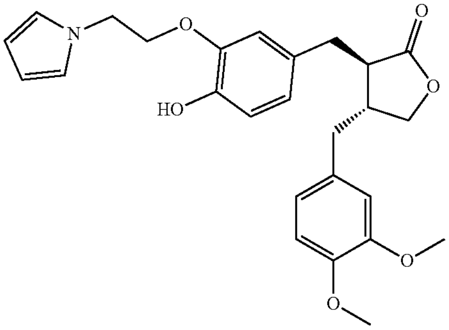 [SMILES: COc1ccc(C[C@H]2COC(=O)[C@@H]2Cc2ccc(O)c(OCCn3cccc3)c2)cc1OC] | 452.2 | $^1H$ NMR (500 MHz, Chloroform-d) δ 6.84-6.81 (m, 1H), 6.78 (d, J = 8.2 Hz, 1H), 6.76 (t, J = 2.1 Hz, 2H), 6.62 (m, 2H), 6.59 (dd, J = 8.1, 2.0 Hz, 1H), 6.51 (d, J = 2.0 Hz, 1H), 6.22 (t, J = 2.1 Hz, 2H), 4.29 (m, 2H), 4.21 (m, 2H), 4.17-4.11 (m, 2H), 3.92-3.89 (m, 1H), 3.88 (s, 3H), 3.84 (s, 3H), 2.91 (qd, J = 14.2, 5.8 Hz, 2H), 2.68 (dd, J = 13.8, 6.4 Hz, 1H), 2.61-2.53 (m, 2H), 2.48 (qd, J = 7.9, 6.4 Hz, 1H). |

TABLE 2-continued

| Compound | Structure | [M + H]+ | 1H NMR |
|---|---|---|---|
| Compounds and characterization data | | | |
| B9-1s | 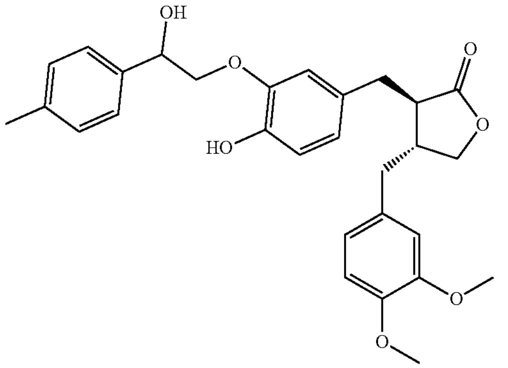 | 493.2 | $^1$H NMR (500 MHz, Chloroform-d) δ 7.33-7.28 (m, 2H), 7.19 (dd, J = 8.1, 3.5 Hz, 2H), 6.84 (d, J = 8.0 Hz, 1H), 6.70 (d, J = 8.2 Hz, 1H), 6.63 (dt, J = 8.1, 1.9 Hz, 1H), 6.57 (dd, J = 20.5, 2.0 Hz, 1H), 6.51 (dd, J = 8.1, 2.0 Hz, 1H), 6.42 (dd, J = 4.2, 2.0 Hz, 1H), 5.06 (dt, J = 8.6, 3.5 Hz, 1H), 4.15 (ddd, J = 9.0, 7.0, 1.9 Hz, 1H), 4.05 (ddd, J = 10.1, 5.7, 3.1 Hz, 1H), 4.00-3.86 (m, 2H), 3.80 (s, 3H), 3.77 (s, 3H), 2.91 (ddd, J = 14.1, 7.6, 4.9 Hz, 1H), 2.80 (dd, J = 14.1, 7.2 Hz, 1H), 2.52 (m, 4H), 2.35 (s, 3H). |
| B9-1t | 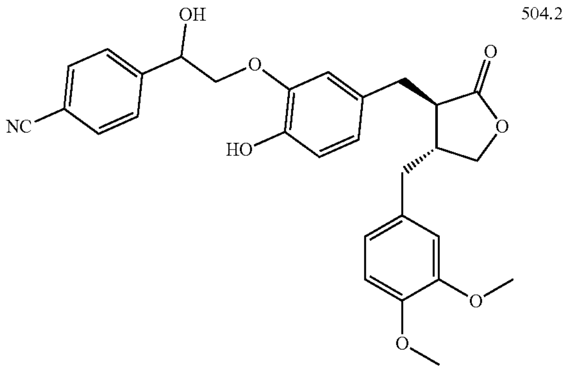 | 504.2 | $^1$H NMR (500 MHz, Chloroform-d) δ 7.73-7.66 (m, 2H), 7.62-7.55 (m, 2H), 6.84 (dd, J = 8.0, 2.7 Hz, 1H), 6.73 (d, J = 8.2 Hz, 1H), 6.63 (dt, J = 8.1, 1.4 Hz, 1H), 6.60-6.50 (m, 2H), 6.44 (t, J = 2.2 Hz, 1H), 5.14 (td, J = 8.2, 3.3 Hz, 1H), 4.21-4.04 (m, 2H), 4.02-3.87 (m, 2H), 3.83 (s, 3H), 3.78 (s, 3H), 2.89-2.81 (m, 2H), 2.67-2.59 (m, 2H), 2.57-2.43 (m, 2H) |
| B9-1u | 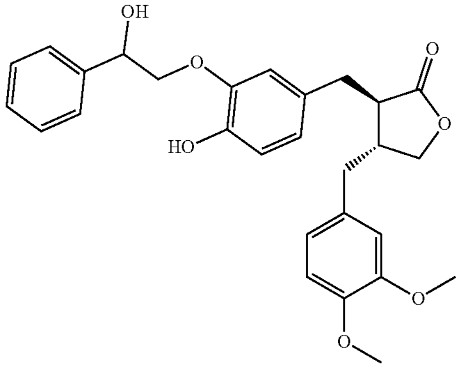 [SMILES: COc1ccc(C[C@H]2COC(=O)[C@@H]2Cc2ccc(O)c(OCC(O)c3ccccc3)c2)cc1OC] | 479.2 | $^1$H NMR (500 MHz, Chloroform-d) δ 7.45-7.30 (m, 5H), 6.84 (dd, J = 8.0, 2.1 Hz, 1H), 6.70 (d, J = 8.2 Hz, 1H), 6.63 (ddd, J = 8.0, 1.9, 1.1 Hz, 1H), 6.60-6.49 (m, 2H), 6.41 (dd, J = 4.7, 2.0 Hz, 1H), 5.10 (ddd, J = 8.7, 5.9, 3.0 Hz, 1H), 4.15 (ddd, J = 8.9, 7.1, 1.8 Hz, 1H), 4.07 (ddd, J = 10.4, 7.4, 3.1 Hz, 1H), 4.02-3.90 (m, 1H), 3.88 (m, 1H), 3.79 (s, 3H), 3.76 (s, 3H), 2.90 (ddd, J = 14.2, 7.0, 5.0 Hz, 1H), 2.80 (dd, J = 14.1, 7.2 Hz, 1H), 2.62-2.41 (m, 4H). |
| B9-1v | 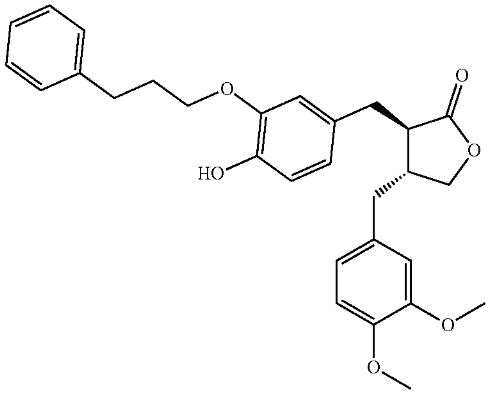 [SMILES: COc1ccc(C[C@H]2COC(=O)[C@@H]2Cc2ccc(O)c(OCCCc3ccccc3)c2)cc1OC] | 477.2 | 1H NMR (500 MHz, Chloroform-d) δ 7.33 (t, J = 7.5 Hz, 2H), 7.24 (dt, J = 7.1, 3.0 Hz, 3H), 6.85 (d, J = 7.8 Hz, 1H), 6.77 (d, J = 8.1 Hz, 1H), 6.66-6.61 (m, 2H), 6.57 (dd, J = 8.1, 2.0 Hz, 1H), 6.49 (d, J = 2.0 Hz, 1H), 4.14 (dd, J = 9.1, 7.0 Hz, 1H), 4.02 (t, J = 6.3 Hz, 2H), 3.92-3.89 (m, 1H), 3.87 (s, 3H), 3.84 (s, 3H), 2.93 (t, J = 6.2 Hz, 2H), 2.83 (t, J = 7.5 Hz, 2H), 2.65 (dt, J = 12.4, 6.4 Hz, 1H), 2.60-2.47 (m, 3H), 2.20-2.12 (m, 2H). |

TABLE 2-continued

| Compounds and characterization data | | | |
|---|---|---|---|
| Compound | Structure | $[M+H]^+$ | $^1H$ NMR |
| B9-1w | 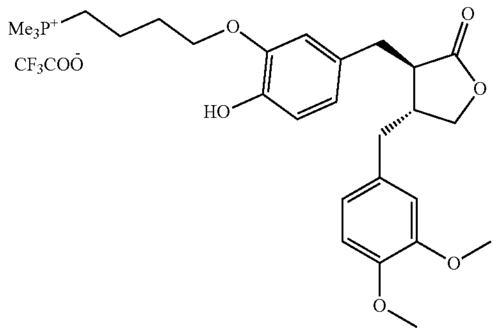 | 603.2 | 1H NMR (500 MHz, Chloroform-d) δ 6.83 (d, J = 8.0 Hz, 1H), 6.75 (d, J = 8.2 Hz, 1H), 6.63 (d, J = 2.0 Hz, 1H), 6.55 (td, J = 7.9, 1.9 Hz, 2H), 6.50 (d, J = 1.9 Hz, 1H), 4.06 (dd, J = 9.0, 6.9 Hz, 1H), 3.94 (t, J = 5.4 Hz, 2H), 3.82 (s, 4H), 3.80 (s, 4H), 2.83 (qd, J = 14.2, 5.7 Hz, 2H), 2.71-2.55 (m, 2H), 2.55-2.43 (m, 2H), 2.39-2.20 (m, 2H), 1.82 (s, 9H). |
| B9-1x | 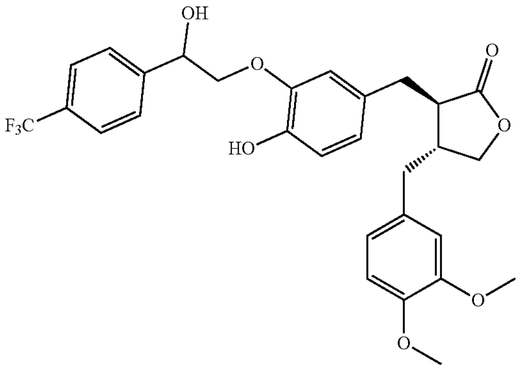 | 547.1 | 1H NMR (500 MHz, Chloroform-d) δ 7.63 (t, J = 8.2 Hz, 2H), 7.55 (t, J = 7.7 Hz, 2H), 6.83 (dd, J = 8.1, 4.8 Hz, 1H), 6.73-6.68 (m, 1H), 6.61 (dt, J = 8.0, 1.5 Hz, 1H), 6.57-6.50 (m, 2H), 6.41 (dd, J = 5.0, 2.0 Hz, 1H), 5.29 (s, 1H), 5.15 (td, J = 8.2, 3.0 Hz, 1H), 4.16 (dd, J = 9.2, 7.2 Hz, 1H), 4.06 (ddd, J = 13.3, 10.1, 3.1 Hz, 1H), 3.96 (dd, J = 10.2, 8.3 Hz, 1H), 3.92-3.84 (m, 1H), 3.79 (s, 3H), 3.76 (d, J = 5.6 Hz, 3H), 2.97-2.75 (m, 2H), 2.66-2.37 (m, 4H). |

Example 3: (3R,4R)-4-(3,4-dimethoxybenzyl)-3-(4-hydroxy-3-phenylethoxybenzyl)-3-methyldihydrofuran-2 (3H)-one (B11-1a)

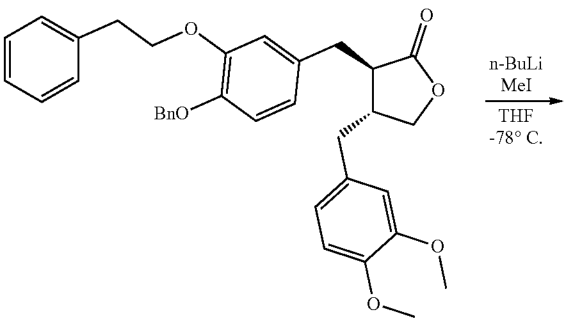

B8-1a

-continued

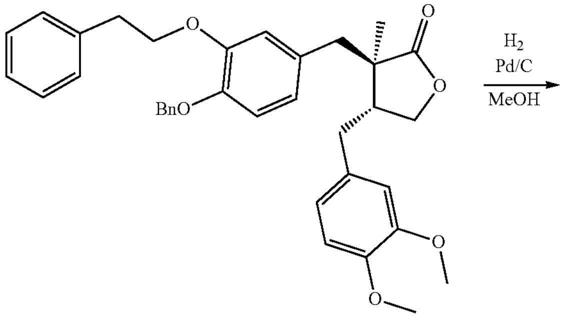

B10-1a

-continued

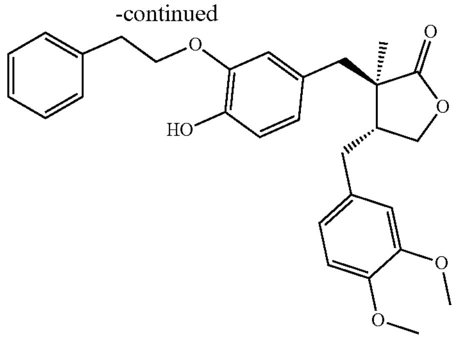

B11-1a

Synthesis of (3R,4R)-3-(4-(benzyloxy)-3-phenylethoxybenzyl)-4-(3,4-dimethoxybenzyl)-3-methyldihydrofuran-2 (3H)-one (B10-1a)

It was synthesized from Compound B8-1a with reference to the synthesis of Compound A3-1. ESI-MS m/z: 567.3 $[M+H]^+$.

Synthesis of (3R,4R)-4-(3,4-dimethoxybenzyl)-3-(4-hydroxy-3-phenylethoxybenzyl)-3-methyldihydrofuran-2 (3H)-one (B11-1a)

It was synthesized from Compound A3-1 with reference to the synthesis of Compound A4-1a. 1H NMR (500 MHZ, Chloroform-d) δ 7.34-7.29 (m, 2H), 7.29-7.26 (m, 3H), 6.82 (d, J=8.1 Hz, 1H), 6.76 (d, J=1.9 Hz, 1H), 6.74-6.71 (m, 1H), 6.66-6.62 (m, 1H), 6.59 (dd, J=8.1, 2.0 Hz, 1H), 6.51 (d, J=2.0 Hz, 1H), 4.25 (dd, J=9.0, 7.7 Hz, 1H), 4.21 (td, J=6.8, 1.5 Hz, 2H), 3.94 (dd, J=9.0, 7.7 Hz, 1H), 3.83 (s, 3H), 3.82 (s, 3H), 3.17 (d, J=14.0 Hz, 1H), 3.09 (t, J=6.8 Hz, 2H), 2.72 (dd, J=13.5, 4.1 Hz, 1H), 2.60 (d, J=14.0 Hz, 1H), 2.48-2.54 (m, 1H), 2.40-2.31 (m, 1H), 1.27 (s, 3H). ESI-MS m/z: 477.2 $[M+H]^+$.

The compounds shown in Table 3 were prepared by using a synthesis method similar to that of Example 3 of the present invention and using appropriate optional starting materials.

TABLE 3

Compounds and characterization data

| Compound | Structure | $[M + H]^+$ | $^1$H NMR |
|---|---|---|---|
| B11-1b | 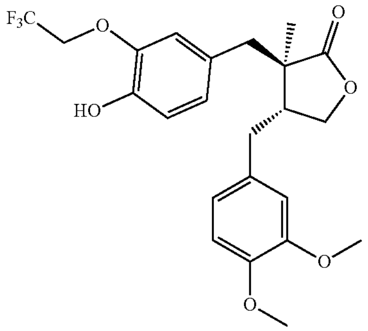 [SMILES: COc1ccc(C[C@H]2COC(=O)[C@]2(C)Cc2ccc(O)c(OCC(F)(F)F)c2)cc1OC] | 455.2 | $^1$H NMR (500 MHz, Chloroform-d) δ 6.89 (d, J = 8.0 Hz, 1H), 6.78 (d, J = 8.1 Hz, 1H), 6.74-6.71 (m, 2H), 6.62 (dd, J = 8.1, 2.0 Hz, 1H), 6.54 (d, J = 2.0 Hz, 1H), 4.36 (pd, J = 8.1, 7.6, 4.1 Hz, 2H), 3.97 (dd, J = 9.1, 7.7 Hz, 1H), 3.88 (m, 1H), 3.85 (s, 3H), 3.84 (s, 3H), 3.18 (d, J = 14.1 Hz, 1H), 2.75 (dd, J = 13.4, 3.9 Hz, 1H), 2.59 (d, J = 14.1 Hz, 1H), 2.50 (m, 1H), 2.42 (d, J = 13.4 Hz, 1H), 1.29 (s, 3H). |
| B11-1c | 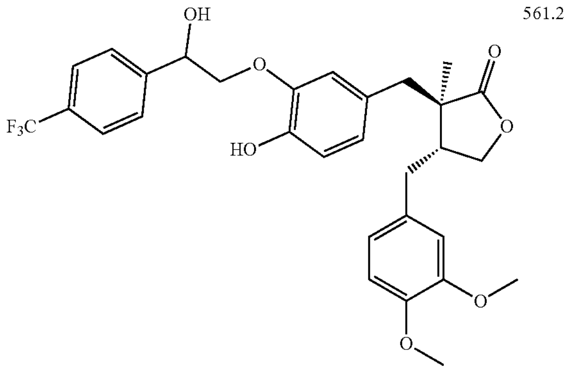 | 561.2 | $^1$H NMR (500 MHz, Chloroform-d) δ 7.60 (dt, J = 8.4, 2.8 Hz, 3H), 7.52 (dd, J = 12.3, 8.1 Hz, 2H), 6.85 (dd, J = 8.0, 2.3 Hz, 1H), 6.73 (dd, J = 8.2, 1.6 Hz, 1H), 6.71 (d, J = 1.8 Hz, 1H), 6.66 (dt, J = 8.1, 2.4 Hz, 1H), 6.61-6.56 (m, 1H), 6.52 (t, J = 2.5 Hz, 1H), 5.16-5.09 (m, 1H), 4.12 (ddd, J = 10.0, 5.1, 3.0 Hz, 1H), 4.02-3.95 (m, 1H), 3.95-3.88 (m, 1H), 3.82 (s, 3H), 3.81 (s, 3H), 3.11 (dd, J = 14.1, 5.9 Hz, 1H), 2.71 (ddd, J = 13.6, 6.9, 4.2 Hz, 1H), 2.57 (dd, J = 14.1, 3.4 Hz, 1H), 2.51 (d, J = 7.7 Hz, OH), 2.36 (s, 0H), 1.25 (s, 3H) |

TABLE 3-continued

Compounds and characterization data

| Compound | Structure | $[M + H]^+$ | $^1H$ NMR |
|---|---|---|---|
| B11-1d | 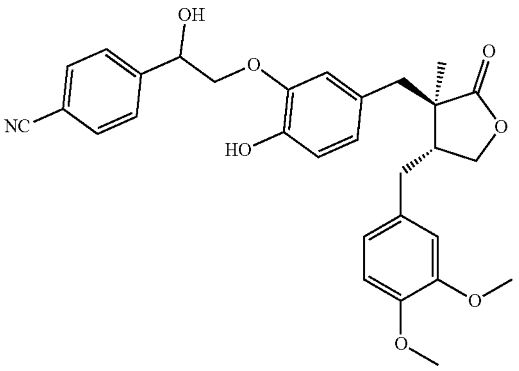 [SMILES: COc1ccc(C[C@H]2COC(=O)[C@]2(C)Cc2ccc(O)c(OCC(O)c3ccc(C#N)cc3)c2)cc1OC] | 518.2 | $^1H$ NMR (500 MHz, Chloroform-d) δ 7.68 (dq, J = 8.2, 1.7 Hz, 2H), 7.61-7.54 (m, 2H), 6.86 (dd, J = 8.1, 2.6 Hz, 1H), 6.76 (d, J = 7.9 Hz, 2H), 6.68 (dt, J = 8.1, 1.7 Hz, 1H), 6.63-6.58 (m, 1H), 6.53 (dd, J = 5.4, 2.1 Hz, 1H), 5.15 (ddd, J = 11.8, 8.1, 3.4 Hz, 1H), 4.13 (dd, J = 7.0, 3.5 Hz, 1H), 4.03 (ddd, J = 10.7, 8.1, 1.7 Hz, 1H), 3.96-3.93 (m, 1H), 3.84 (s, 6H), 3.83-3.79 (m, 1H), 3.16 (dd, J = 14.0, 5.0 Hz, 1H), 2.75 (ddd, J = 13.2, 8.7, 4.3 Hz, 1H), 2.58 (dd, J = 14.1, 3.0 Hz, 1H), 2.54-2.45 (m, OH), 2.39 (ddd, J = 14.7, 10.7, 4.2 Hz, 1H), 1.28 (d, J = 4.3 Hz, 3H). |
| B11-1e (Control) | 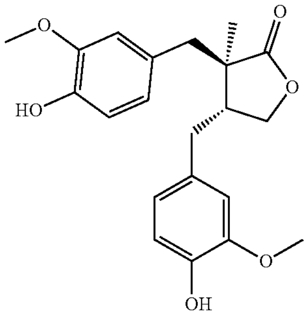 | 373.2 | $^1H$ NMR (500 MHz, Chloroform-d) δ 6.84 (d, J = 8.0 Hz, 1H), 6.80 (d, J = 8.0 Hz, 1H), 6.74 (d, J = 2.0 Hz, 1H), 6.64 (dd, J = 8.1, 2.0 Hz, 1H), 6.55 (dd, J = 8.0, 2.0 Hz, 1H), 6.49 (d, J = 2.0 Hz, 1H), 3.95 (dd, J = 9.0, 7.7 Hz, 1H), 3.84 (s, 3H), 3.84 (s, 3H), 3.82 (dd, J = 10.6, 9.2 Hz, 2H), 3.20 (d, J = 14.1 Hz, 1H), 2.71 (dd, J = 13.5, 4.1 Hz, 1H), 2.61 (d, J = 14.0 Hz, 1H), 2.54-2.44 (m, 1H), 2.35 (dd, J = 13.6, 11.0 Hz, 1H), 1.28 (s, 3H). |
| B11-1f | 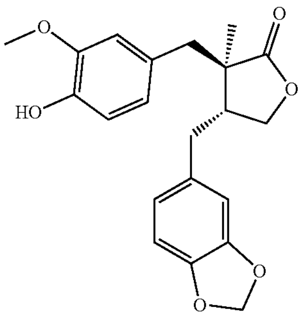 [SMILES: COc1cc(C[C@@]2(C)C(=O)OC[C@@H]2Cc2ccc3c(c2)OCO3)ccc1O] | 371.1 | $^1H$ NMR (500 MHz, Chloroform-d) δ 6.86 (d, J = 8.0 Hz, 1H), 6.74 (d, J = 2.0 Hz, 1H), 6.70 (d, J = 7.8 Hz, 1H), 6.65 (dd, J = 8.1, 2.0 Hz, 1H), 6.52 (d, J = 1.7 Hz, 1H), 6.50 (dd, J = 7.8, 1.8 Hz, 1H), 5.94-5.90 (m, 2H), 3.94 (dd, J = 9.0, 7.8 Hz, 1H), 3.85 (s, 3H), 3.80 (s, OH), 3.15 (d, J = 14.0 Hz, 1H), 2.66-2.70 (m, 1H), 2.62 (d, J = 14.0 Hz, 1H), 2.51 (dddd, J = 11.7, 10.3, 7.7, 4.0 Hz, 1H), 2.34 (dd, J = 13.6, 11.2 Hz, 1H), 1.26 (s, 3H). |
| B11-1g | 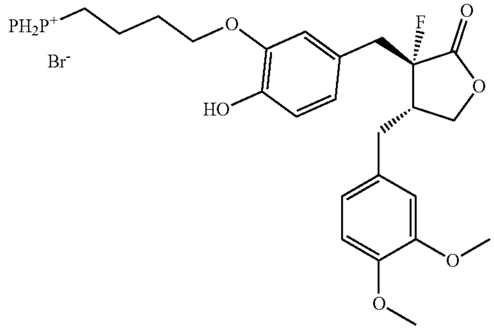 | 773.1 | $^1H$ NMR (500 MHz, Chloroform-d) δ 7.80-7.66 (m, 15H), 6.94 (d, J = 8.0 Hz, 1H), 6.80 (d, J = 8.2 Hz, 1H), 6.65 (dd, J = 8.1, 2.0 Hz, 1H), 6.61-6.54 (m, 3H), 3.96 (dd, J = 7.5, 3.4 Hz, 2H), 3.84 (d, J = 0.9 Hz, 6H), 3.63-3, 61 (m, 2H), 3.24 (t, J = 13.6 Hz, 1H), 3.00 (t, J = 13.4 Hz, 1H), 2.92-2.82 (m, 1H), 2.62-2.49 (m, 1H), 2.04-2.00(m, 5H), 1.96 (s, 2H). |

TABLE 3-continued
| Compounds and characterization data | | | |
|---|---|---|---|
| Compound | Structure | [M + H]+ | 1H NMR |
| B11-1h (Control) | 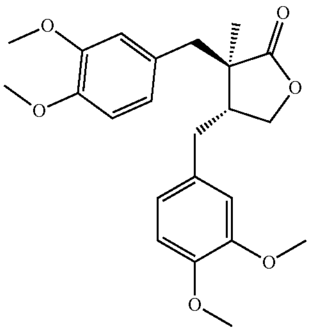 | 401.1 | 1H NMR (500 MHz, Chloroform-d) δ 6.81-6.74 (m, 3H), 6.70 (d, J = 7.9 Hz, 1H), 6.61 (d, J = 7.9 Hz, 1H), 6.52 (s, 1H), 3.95 (t, J = 8.4 Hz, 1H), 3.86 (s, 4H), 3.85 (s, 3H), 3.84 (s, 3H), 3.84 (s, 3H), 3.81 (d, J = 9.6 Hz, 1H), 3.21 (d, J = 14.0 Hz, 1H), 2.73 (dd, J = 13.6, 4.1 Hz, 1H), 2.64 (d, J = 13.9 Hz, 1H), 2.43-2.33 (m, 1H), 2.22 (t, J = 7.6 Hz, 2H), 1.29 (s, 3H). |
Example 4: (3R,4R)-4-(3,4-dimethoxybenzyl)-3-(4-hydroxy-3-(methylamino)benzyl)dihydrofuran-2(3H)-one (B9-3)
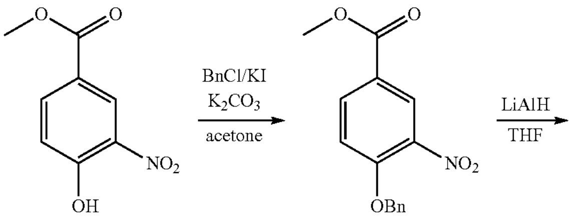
B5-3a B5-3b
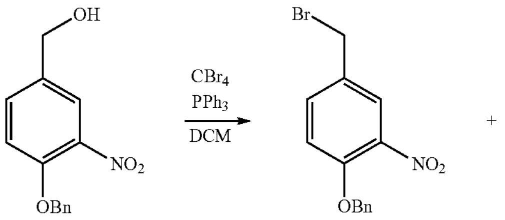
B5-3c B5-3e
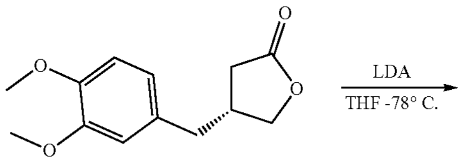
B5-1
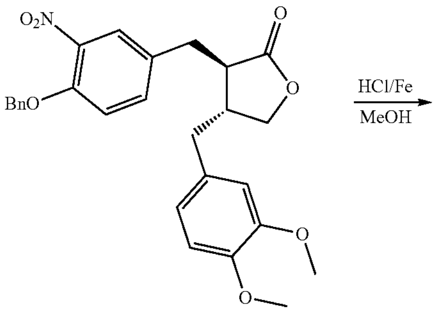
B6-3
-continued
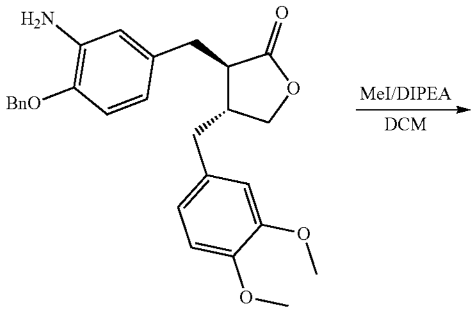
B7-3
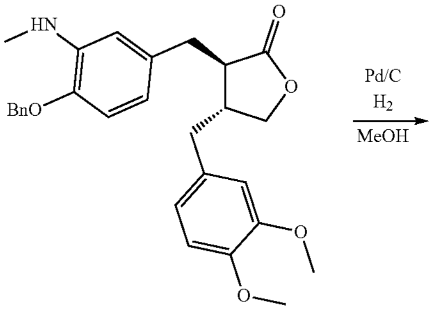
B8-3
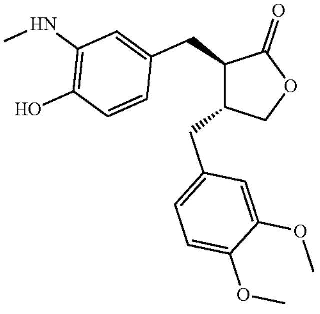
B9-3

Synthesis of methyl 4-(benzyloxy)-3-nitrobenzoate (B5-3b)

Commercially available raw materials B5-3a (1 g, 5 mmol), benzyl chloride (687 μl, 6 mmol), potassium carbonate (1.38 g, 10 mmol), and potassium iodide (83 mg, 0.5 mmol) were added to 30 ml acetone, heated and stirred at 60° C. for 5 hours. After the reaction was completed, potassium carbonate was removed by suction filtration, and the filtrate was distilled under reduced pressure and subjected to silica gel column chromatography (V (petroleum ether):V (ethyl acetate)=3:1) to 1.32 g of light yellow solid B5-3b, with a yield of 91.9%. 1H NMR (500 MHZ, Chloroform-d) δ 8.52 (d, J=2.1 Hz, 1H), 8.17 (dd, J=8.8, 2.2 Hz, 1H), 7.49-7.32 (m, 5H), 7.16 (d, J=8.8 Hz, 1H), 5.31 (s, 2H), 3.93 (s, 3H). ESI-MS m/z: 288.1 $[M+H]^+$.

Synthesis of (4-(benzyloxy)-3-nitrophenyl) methanol (B5-3c)

The product B5-3b (1.04 g, 4 mmol) of the previous step was dissolved in 20 ml of anhydrous THF, and lithium aluminum tetrahydride solution (2.5M/L in THF) (2.5 ml, 10 mmol) was added dropwise in an ice bath, and stirred in an ice bath for 30 minutes. Then the mixture was slowly warmed to room temperature for 2 hours. After the reaction was completed, lithium aluminum tetrahydride was quenched with ice water, the mixture was extracted with ethyl acetate three times, the organic layer was washed with saturated sodium chloride solution three times, dried with anhydrous sodium sulfate, filtered with suction, and the filtrate was concentrated under reduced pressure and subjected to silica gel column chromatography (V (petroleum ether):V (ethyl acetate)=2:1) to obtain 864 mg of yellow oil B5-3c with a yield of 83.1%. 1H NMR (500 MHZ, Chloroform-d) δ 7.89 (d, J=2.2 Hz, 1H), 7.52 (dd, J=8.6, 2.3 Hz, 1H), 7.50-7.46 (m, 2H), 7.45-7.40 (m, 2H), 7.38-7.33 (m, 1H), 7.13 (d, J=8.6 Hz, 1H), 5.27 (s, 2H), 4.71 (s, 2H). ESI-MS m/z: 260.1 $[M+H]^+$.

1-(benzyloxy)-4-(bromomethyl)-2-nitrobenzene (B5-3e)

B5-3e as yellow oil was synthesized with a yield of 86% by using B5-3c as raw materials and referring to the operation of B5-2e. ESI-MS m/z: 322.0 $[M+H]^+$.

Synthesis of (3R,4R)-3-(4-(benzyloxy)-3-nitrobenzyl)-4-(3,4-dimethoxybenzyl)dihydrofuran-2 (3H)-one (B6-3)

A light yellow oil was synthesized with a yield of 78% by using B5-3e and B5-1 as raw materials and referring to the operation of B6-1. ESI-MS m/z: 478.2 $[M+H]^+$.

Synthesis of (3R,4R)-3-(3-amino-4-(benzyloxy) benzyl)-4-(3,4-dimethoxybenzyl)dihydrofuran-2 (3H)-one (B7-3)

The product B6-3 of the previous step (477 mg, 1 mmol) and iron powder (280 mg, 5 mmol) were dissolved in 10 ml of methanol, catalyzed by adding 1 ml of dilute hydrochloric acid (2M/L), stirred at room temperature, and reacted overnight. After the reaction was completed, the iron powder was removed by filtration. The filtrate was concentrated under reduced pressure and subjected to silica gel column chromatography (V (petroleum ether):V (ethyl acetate)=1:1) to obtain 421 g of light yellow oil B7-3, with a yield of 94.2%. ESI-MS m/z: 448.2 $[M+H]^+$.

Synthesis of (3R,4R)-3-(4-(benzyloxy)-3-(methylamino)benzyl)-4-(3,4-dimethoxybenzyl)dihydrofuran-2 (3H)-one (B8-3)

The product B7-3 from the previous step (223 mg, 0.5 mmol), N,N-diisopropylethylamine (350 μl, 2 mmol), and methyl iodide (40 μl, 0.6 mmol) were added to 5 ml of methylene chloride, and stirred at room temperature for 5 h. After the reaction was completed, the mixture was separated by silica gel column chromatography (V (petroleum ether):V (ethyl acetate)=1:1) to obtain 167 mg of light yellow oil B8-3, with a yield of 72.6%. ESI-MS m/z: 462.2 $[M+H]^+$.

Synthesis of (3R,4R)-4-(3,4-dimethoxybenzyl)-3-(4-hydroxy-3-(methylamino)benzyl)dihydrofuran-2 (3H)-one (B9-3)

B9-3 was obtained in 78.2% yield by using B8-3 as raw material and referring to the procedure for synthesizing A4-1a as well as the feed ratio. 1H NMR (500 MHZ, Chloroform-d) δ 7.10 (d, J=8.1 Hz, 1H), 6.79 (d, J=8.1 Hz, 1H), 6.59 (dd, J=8.1, 2.0 Hz, 1H), 6.50 (ddd, J=12.0, 8.0, 2.1 Hz, 3H), 4.18 (dd, J=9.2, 7.5 Hz, 1H), 3.92-3.87 (m, 1H), 3.87 (s, 4H), 3.83 (s, 3H), 3.17 (s, 3H), 2.88 (dd, J=6.0, 3.7 Hz, 2H), 2.66 (dd, J=13.8, 6.7 Hz, 1H), 2.62-2.55 (m, 2H), 2.51-2.43 (m, 1H). ESI-MS m/z: 372.2 $[M+H]^+$.

The compounds shown in Table 4 were prepared by using a synthesis method similar to that of Example 4 of the present invention and using appropriate optional starting materials.

TABLE 4

| Compounds and characterization data | | | |
|---|---|---|---|
| Example | structure | [M + H]$^+$ | $^1$H NMR |
| B9-4 | 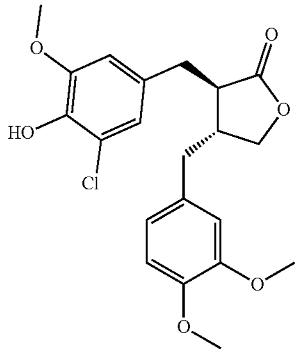 [SMILES: COc1ccc(C[C@H]2COC(=O)[C@@H]2Cc2cc(Cl)c(O)c(OC)c2)cc1OC] | 407.1 | $^1$H NMR (500 MHz, Chloroform-d) δ 6.77 (d, J = 8.1 Hz, 1H), 6.64 (d, J = 1.8 Hz, 1H), 6.57 (dd, J = 6.9, 1.9 Hz, 2H), 6.50 (d, J = 2.0 Hz, 1H), 4.19 (dd, J = 9.1, 7.5 Hz, 1H), 3.90 (dd, J = 9.2, 7.9 Hz, 1H), 3.86 (s, 3H), 3.84 (s, 3H), 3.82 (s, 3H), 2.87 (t, J = 6.4 Hz, 2H), 2.65 (dd, J = 13.7, 7.0 Hz, 1H), 2.60 (d, J = 7.8 Hz, 1H), 2.59-2.53 (m, 1H), 2.47 (p, J = 7.8 Hz, 1H). |
| B9-7 | 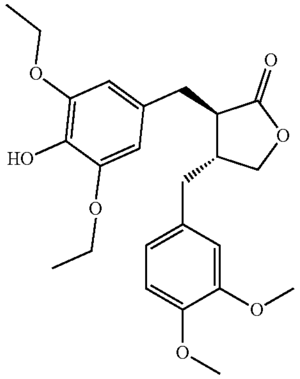 [SMILES: CCOc1cc(C[C@H]2C(=O)OC[C@@H]2Cc2ccc(OC)c(OC)c2)cc(OCC)c1O] | 431.2 | $^1$H NMR (500 MHz, Chloroform-d) δ 6.75 (d, J = 8.1 Hz, 1H), 6.55 (dd, J = 8.2, 2.0 Hz, 1H), 6.48 (d, J = 2.0 Hz, 1H), 6.34 (s, 2H), 4.16-4.10 (m, 1H), 4.05 (q, J = 7.0 Hz, 4H), 3.90-3.86 (m, 1H), 3.86 (s, 1H), 3.82 (s, 3H), 2.90 (d, J = 5.8 Hz, 2H), 2.65 (dd, J = 13.3, 5.9 Hz, 1H), 2.60-2.44 (m, 3H), 1.43 (t, J = 7.0 Hz, 6H). |
| B9-8 | 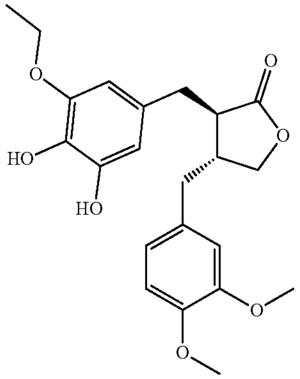 [SMILES: CCOc1cc(C[C@H]2C(=O)OC[C@@H]2Cc2ccc(OC)c(OC)c2)cc(O)c1O] | 402.2 | $^1$H NMR (500 MHz, Chloroform-d) δ 6.75 (d, J = 8.1 Hz, 1H), 6.56 (dd, J = 8.1, 2.1 Hz, 1H), 6.50 (d, J = 2.0 Hz, 1H), 6.37 (d, J = 1.8 Hz, 1H), 6.27 (d, J = 1.8 Hz, 1H), 4.15-4.10 (m, 1H), 4.02 (qd, J = 7.0, 1.6 Hz, 2H), 3.90-3.86 (m, 1H), 3.85 (s, 3H), 3.83 (s, 3H), 2.91 (dd, J = 14.0, 5.0 Hz, 1H), 2.84 (dd, J = 14.0, 6.6 Hz, 1H), 2.63 (qd, J = 8.4, 7.4, 4.7 Hz, 1H), 2.57-2.46 (m, 3H), 1.41 (t, J = 7.0 Hz, 3H). |
| B9-9 | 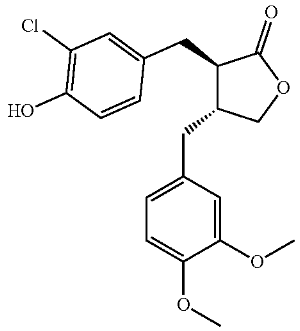 [SMILES: COc1ccc(C[C@H]2COC(=O)[C@@H]2Cc2ccc(O)c(Cl)c2)cc1OC] | 377.1 | $^1$H NMR (500 MHz, Chloroform-d) δ 7.03 (d, J = 1.9 Hz, 1H), 6.96-6.89 (m, 2H), 6.78 (d, J = 8.1 Hz, 1H), 6.58 (dd, J = 8.1, 2.1 Hz, 1H), 6.49 (d, J = 2.0 Hz, 1H), 4.18 (dd, J = 9.2, 7.5 Hz, 1H), 3.89 (dd, J = 9.2, 8.0 Hz, 1H), 3.87 (s, 3H), 3.84 (s, 3H), 2.89 (t, J = 5.6 Hz, 2H), 2.63 (dd, J = 13.8, 6.8 Hz, 1H), 2.60-2.53 (m, 2H), 2.51-2.41 (m, 1H). |

TABLE 4-continued

| Compounds and characterization data | | | |
|---|---|---|---|
| Example | structure | [M + H]+ | 1H NMR |
| B9-10 | 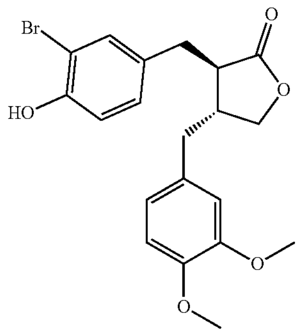 [SMILES: COc1ccc(C[C@H]2COC(=O)[C@@H]2Cc2ccc(O)c(Br)c2)cc1OC] | 421.1 | 1H NMR (500 MHz, Chloroform-d) δ 7.20 (d, J = 2.1 Hz, 1H), 7.01 (dd, J = 8.3, 2.1 Hz, 1H), 6.94 (d, J = 8.3 Hz, 1H), 6.81 (d, J = 8.1 Hz, 1H), 6.61 (dd, J = 8.1, 2.1 Hz, 1H), 6.52 (d, J = 2.1 Hz, 1H), 4.21 (dd, J = 9.1, 7.5 Hz, 1H), 3.95-3.90 (m, 1H), 3.90 (s, 3H), 3.87 (s, 3H), 2.92 (dd, J = 6.1, 4.0 Hz, 2H), 2.66 (dd, J = 13.8, 6.8 Hz, 1H), 2.59 (tt, J = 7.9, 5.4 Hz, 2H), 2.54-2.44 (m, 1H). |
| B9-12 | 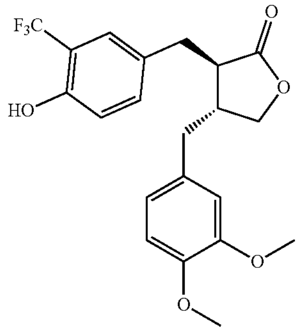 [SMILES: COc1ccc(C[C@H]2COC(=O)[C@@H]2Cc2ccc(O)c(C(F)(F)F)c2)cc1OC] | 411.4 | 1H NMR (500 MHz, Chloroform-d) δ 7.24 (d, J = 2.1 Hz, 1H), 7.15 (dd, J = 8.4, 2.2 Hz, 1H), 6.85 (d, J = 8.4 Hz, 1H), 6.80 (d, J = 8.2 Hz, 1H), 6.60 (dd, J = 8.1, 2.0 Hz, 1H), 6.49 (d, J = 2.0 Hz, 1H), 4.23 (dd, J = 9.2, 7.5 Hz, 1H), 3.94 (dd, J = 9.2, 7.7 Hz, 1H), 3.89 (s, 3H), 3.83 (s, 3H), 3.01-2.89 (m, 2H), 2.70-2.55 (m, 3H), 2.47 (p, J = 7.7 Hz, 1H). |
| B9-13 | 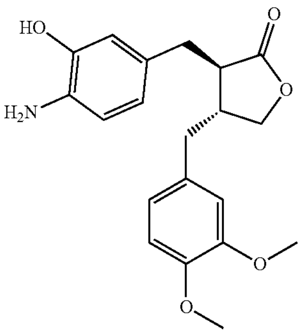 [SMILES: COc1ccc(C[C@H]2COC(=O)[C@@H]2Cc2ccc(N)c(O)c2)cc1OC] | 358.1 | 1H NMR (500 MHz, Chloroform-d) δ 6.77 (d, J = 8.1 Hz, 1H), 6.68-6.63 (m, 1H), 6.57 (dd, J = 8.1, 2.0 Hz, 1H), 6.53-6.45 (m, 3H), 4.10 (dd, J = 9.0, 7.0 Hz, 1H), 3.86 (s, 4H), 3.83 (s, 3H), 2.83 (dd, J = 8.0, 5.7 Hz, 2H), 2.67-2.61 (m, 1H), 2.57-2.44 (m, 3H). |
| B9-14 | 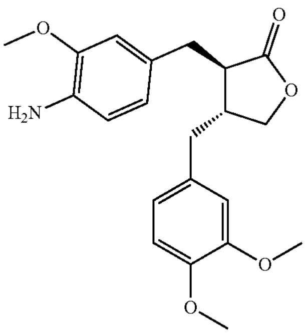 | 372.2 | 1H NMR (500 MHz, Chloroform-d) δ 6.75 (d, J = 8.1 Hz, 1H), 6.62 (d, J = 7.8 Hz, 1H), 6.59 (d, J = 1.8 Hz, 1H), 6.55 (dt, J = 7.6, 1.6 Hz, 2H), 6.48 (d, J = 2.1 Hz, 1H), 4.11 (ddd, J = 9.1, 7.0, 2.7 Hz, 1H), 3.89-3.87 (m, 1H), 3.85 (s, 3H), 3.82 (s, 3H), 3.80 (s, 3H), 2.95 (dd, J = 14.1, 5.1 Hz, 1H), 2.88 (dd, J = 14.0, 6.7 Hz, 1H), 2.64 (q, J = 9.6 Hz, 1H), 2.59-2.47 (m, 3H). |

Example 5: (3R,4R)-4-(3,4-dimethoxybenzyl)-3-(4-hydroxy-3-methoxybenzyl)-5-methyldihydrofuran-2 (3H)-one (C9-1a)

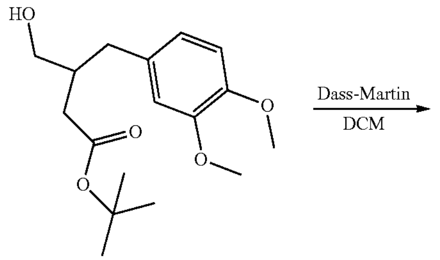

B4-1

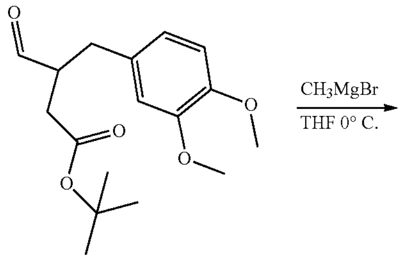

C5-1

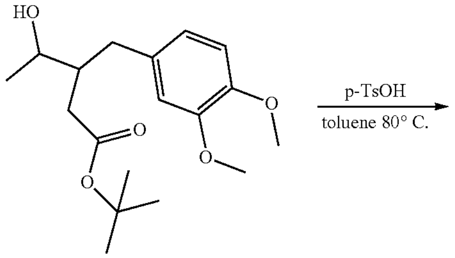

C6-1a

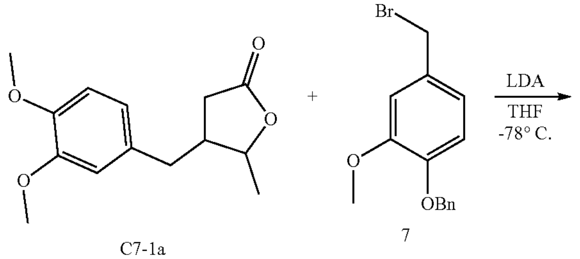

C7-1a 7

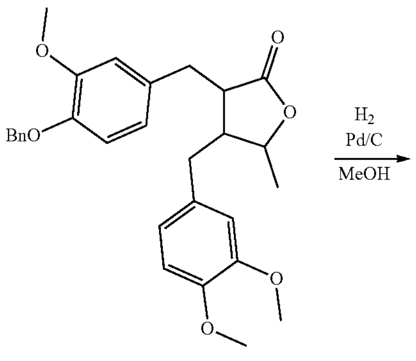

C8-1

-continued

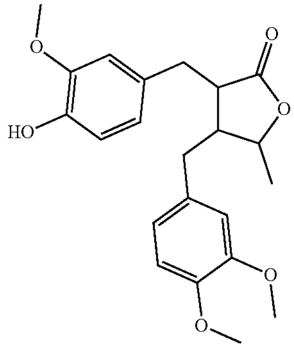

C9-1a

Synthesis of tert-butyl 3-(3,4-dimethoxybenzyl)-4-oxobutyrate (C5-1)

Intermediate B4-1 (620 mg, 2 mmol) was dissolves in 10 mL of dichloromethane, and Desmartin's reagent (932 mg, 2.2 mmol) was added and stirred at room temperature for 1 hour. After the reaction was completed, the reaction was quenched with aqueous sodium thiosulfate solution. The mixture was extracted with dichloromethane three times, the organic layer was washed with water three times, the organic layer was dried with anhydrous sodium sulfate, and filtered with suction. The filtrate was concentrated under reduced pressure, and subjected to silica gel column chromatography (V (petroleum ether):V (ethyl acetate)=4:1) to obtain 587 mg of white oil C5-1 with a yield of 96.5%. ESI-MS m/z: 309.2 $[M+H]^+$.

Synthesis of tert-butyl 3-(3,4-dimethoxybenzyl)-4-hydroxypentanoate (C6-1a)

Intermediate C5-1 (587 mg, 1.9 mmol) was dissolved in ultra-dry tetrahydrofuran, methylmagnesium bromide solution (1M/L in THF) (2 mL, 2 mmol) was added dropwise in an ice bath, and stirred in an ice bath for 30 minutes and the mixture was slowly warmed to room temperature and reacted for 2 hours. After the reaction was completed, the methyl magnesium bromide solution was quenched with ice water, and the mixture was extracted with ethyl acetate three times, the organic layer was washed three times with saturated sodium chloride solution and dried with anhydrous sodium sulfate, filtered with suction, and the filtrate was concentrated under reduced pressure and subjected to silica gel column chromatography (V (petroleum ether):V (ethyl acetate)=4:1) to obtain 592 mg of transparent oil C6-1 with a yield of 91.1%. ESI-MS m/z: 325.2 $[M+H]^+$.

Synthesis of 4-(3,4-dimethoxybenzyl)-5-methyldihydrofuran-2 (3H)-one (C7-1a)

C7-1a was obtained with a yield of 82.2% by using C6-1a as raw material and referring to the operating steps for synthesizing B5-1 and feeding ratio. ESI-MS m/z: 251.1 $[M+H]^+$.

3-(4-(benzyloxy)-3-methoxybenzyl)-4-(3,4-dimethoxybenzyl)-5-methyldihydrofuran-2 (3H)-one (C8-1)

C8-1 was obtained with a yield of 56.3% by using C7-1a and 7 as raw materials and referring to the operating steps for synthesizing B6-1 and feeding ratio. ESI-MS m/z: 477.2 $[M+H]^+$.

4-(3,4-dimethoxybenzyl)-3-(4-hydroxy-3-methoxybenzyl)-5-methyldihydrofuran-2 (3H)-one (C9-1a)

C9-1a was obtained with a yield of 87.4% by using C8-1 as raw material and referring to the operating steps for synthesizing A4-1a and feeding ratio. 1H NMR (400 MHZ, Chloroform-d) δ 6.77 (d, J=8.0 Hz, 1H), 6.71 (d, J=8.1 Hz, 1H), 6.57 (d, J=1.9 Hz, OH), 6.51 (dt, J=7.9, 1.8 Hz, 1H), 6.48 (d, J=1.9 Hz, 1H), 6.41 (d, J=2.0 Hz, 1H), 3.86 (d, J=3.4 Hz, 3H), 3.83 (d, J=4.1 Hz, 2H), 3.78-3.69 (m, 5H), 2.96 (dd, J=14.2, 5.9 Hz, OH), 2.90-2.82 (m, 1H), 2.70-2.59 (m, 2H), 2.61-2.46 (m, 1H), 1.33 (d, J=6.6 Hz, 2H), 1.07 (d, J=6.2 Hz, 1H). ESI-MS m/z: 387.2 $[M+H]^+$.

The compounds shown in Table 5 were prepared by using a synthesis method similar to that of Example 5 of the present invention and using appropriate optional starting materials.

TABLE 5

| Compounds and characterization data | | | |
|---|---|---|---|
| Compound | Structure | $[M + H]^+$ | $^1H$ NMR |
| C9-1b | 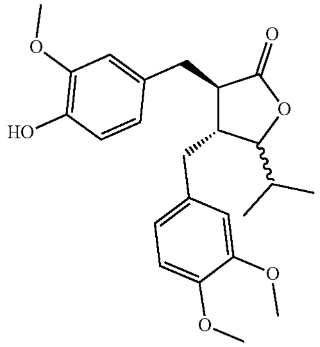 [SMILES: COc1cc(C[C@H]2C(=O)OC(C(C)C)[C@@H]2Cc2ccc(OC)c(OC)c2)ccc1O] | 415.2 | $^1H$ NMR (400 MHz, Chloroform-d) δ 6.74 (d, J = 7.9 Hz, 1H), 6.61 (d, J = 8.1 Hz, 1H), 6.42 (dd, J = 7.9, 2.0 Hz, 1H), 6.34 (dd, J = 8.2, 2.0 Hz, 1H), 6.21 (dd, J = 10.2, 2.0 Hz, 2H), 4.11 (dd, J = 9.9, 5.2 Hz, 1H), 3.85 (s, 3H), 3.70 (s, 3H), 3.63 (s, 3H), 2.94-2.83 (m, 2H), 2.61-2.57 (m, 2H), 2.36 (dt, J = 12.5, 4.7 Hz, 1H), 2.01 (dq, J = 9.7, 6.5 Hz, 1H), 1.14 (d, J = 6.4 Hz, 3H), 0.99 (d, J = 6.6 Hz, 3H). |

Example 6: 4-(((3R,4R)-4-(3,4-dimethoxybenzyl)-3-methyl-2-oxotetrahydrofuran-3-yl)methyl)-2-methoxyphenyl dihydrogen phosphate (A5)

A5

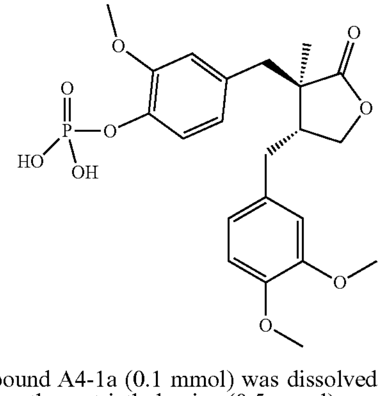

Compound A4-1a (0.1 mmol) was dissolved in ultra-dry dichloromethane, triethylamine (0.5 mmol) was added in an ice bath, stirred evenly, and then phosphorus oxychloride (0.2 mmol) was added and reacted in an ice bath for 30 minutes. The reaction was quenched with ice water, the reaction solution was extracted with dichloromethane, dried over anhydrous magnesium sulfate, filtered, distilled under reduced pressure, and purified by semi-preparative liquid chromatogram to obtain compound A5. $^1H$ NMR (500 MHZ, DMSO-d6) δ 7.21 (d, J=8.2 Hz, 1H), 6.92 (d, J=2.0 Hz, 1H), 6.86 (d, J=8.2 Hz, 1H), 6.75 (dd, J=8.3, 2.0 Hz, 1H), 6.71 (d, J=2.0 Hz, 1H), 6.67 (dd, J=8.0, 2.1 Hz, 1H), 4.02 (t, J=9.4 Hz, 1H), 3.94 (t, J=8.1 Hz, 1H), 3.74 (s, 3H), 3.72 (s, 3H), 3.71 (s, 3H), 2.99 (d, J=13.6 Hz, 1H), 2.75 (d, J=13.6 Hz, 1H), 2.69-2.62 (m, 1H), 2.48-2.37 (m, 1H), 2.00 (dt, J=15.9, 6.9 Hz, 2H), 1.22 (s, 3H). MS (ESI, m/z): 465.2 $[M-1]^-$.

The compounds shown in Table 6 were prepared by using a synthesis method similar to that of Example 6 of the present invention and using appropriate optional starting materials

| Compound | Structure | [M − H]⁻ | $^1$H NMR |
| --- | --- | --- | --- |
| A6 | 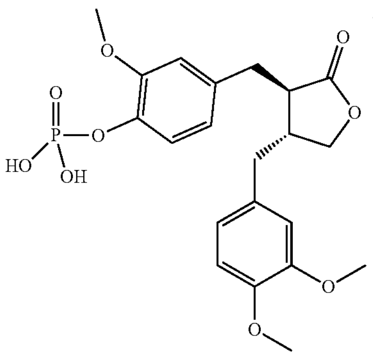 [SMILES: COc1ccc(C[C@H]2COC(=O)[C@@H]2Cc2ccc(OP(=O)(O)O)c(OC)c2)cc1OC] | 451.1 | $^1$H NMR (500 MHz, Chloroform-d) δ 7.13 (d, J = 8.2 Hz, 1H), 6.74 (d, J = 8.1 Hz, 1H), 6.61 (s, 1H), 6.54 (d, J = 8.1 Hz, 2H), 6.44 (d, J = 1.8 Hz, 1H), 4.20 (t, J = 8.3 Hz, 1H), 3.92-3.86 (m, 1H), 3.81 (s, 3H), 3.76 (s, 3H), 3.71 (s, 3H), 2.84 (t, J = 6.0 Hz, 2H), 2.57 (dd, J = 17.1, 7.3 Hz, 3H), 2.45 (q, J = 7.5 Hz, 1H). |

Example 7 Pharmacological Activity and Efficacy Evaluation

1. Evaluation of the Inhibitory Activity of Compounds on Mitochondrial Respiratory Complex I (Complex I)

1.1 Evaluation Method

Mitochondria were extracted from mouse heart tissue. 200-250 mL of solution A (0.22M mannitol, 0.07M sucrose, 0.02M HEPES, 2 mM Tris-HCl, 1 mM EDTA, pH 7.2, 0.4% BSA) was added to the heart tissue. The tissue was cut up and then washed three times with solution A to remove blood and connective tissue, then homogenized using a glass homogenizer about 30 times. The suspension was centrifuged at 3000 g for 1.5 min, and the supernatant was retained. The precipitate was resuspended in solution A with protease inhibitor and re-centrifuged to collect the supernatant. The supernatants from two collections were mixed for the next step. The supernatant was centrifuged at 17500 g for 2.5 min and the supernatant was discarded. The precipitate was resuspended in solution A with protease inhibitor, centrifuged at 17500 g for 4.5 min, resuspended in solution B (2.5 mM potassium phosphate, 5 mM $MgCl_2$ pH 7.2) and repeatedly frozen and thawed to obtain a solution of the mitochondrial complex for subsequent assay.

To measure the NADH activity of Complex I, 2.5 mL of reaction solution containing 50 mM HEPES, 5 mM $MgCl_2$ pH 7.5 and 30 μg of mitochondrial protein from the above process was prepared. The compound to be detected was added and equilibrated for 5 minutes, and then was dispensed into each well. Finally, NADH (50 μM) was quickly added, and data at 340 nM were read every 30 sec for a total of 15 minutes. Calculation: the NADH reaction rates for different compounds were calculated, then the inhibition rate (compound reaction rate/control reaction rate×100) was calculated, and the $IC_{50}$ value of the compound was finally calculated.

1.1 Evaluation Results

TABLE 6

Inhibitory activity of compounds against Complex I

| Compound | Complex I $IC_{50}$(nM) |
| --- | --- |
| A4-1a | 507 |
| A4-1b | 1271 |
| A4-1c | 185 |
| A4-1e | 473 |
| B9-1a | 54 |
| B9-1d | 696 |
| B9-1p | 465 |
| B9-1q | 64 |
| B9-1r | 316 |
| B9-1u | 564 |
| B9-1v | 34 |
| B9-1x | 650 |
| B11-1a | 646 |
| B11-1b | 668 |
| B11-1e | 1374 |
| B11-1f | 420 |
| B11-1h | 13220 |

It can be seen from the evaluation results that the compounds of the present invention have Complex I-inhibiting activity at micromolar to nanomolar levels, and can be used to prepare a medicament for treating diseases caused by abnormal function of the mitochondrial respiratory chain complex I.

2. Evaluation of the Effects of Compounds on the Viability of Human Acute Myeloid Leukemia Cells (OCI-AML3)

2.1 Experimental Methods

OCI-AML3 cells, suspension cells, were cultured in RPIM1640+10% FBS+1% PS culture medium at 37° C. and 5% $CO_2$. OCI-AML3 was seeded in a 96-well plate at 20,000 cells/well, and different concentrations of compounds were added (40 μM was the highest concentration, diluted according to ¼, a total of 7 concentrations). After incubation for 3 days, 10 μl CCK8 reagent was added to each well. After incubation for 2 hours, OD450 was detected by a microplate reader, then the effect of the compound on cell viability, $IC_{50}$ value was calculated.

2.2 Evaluation Results

TABLE 7

Inhibitory activity of representative compounds on OCI-AML3 cells

| Compound | OCI-AML3 $IC_{50}$(nM) |
|---|---|
| A4-1a | 81 |
| A4-1d | 169 |
| A4-1i | 91 |
| B9-1d | 602 |
| B9-1e | 274 |
| B11-1b | 47 |
| B11-1c | 289 |
| Arctigenin | 589 |

It can be seen from the evaluation results that the compounds of the present invention have a good effect of inhibiting the activity of OCI-AML3 cells and can be used to prepare a medicament for treating acute myeloid leukemia.

3. Evaluation of the Effects of Compounds on the Viability of Human Neuroblastoma Cells (NB-1)

3.1 Experimental Methods

NB-1 cells, suspension cells, were cultured in RPIM1640+10% FBS+1% PS culture medium at 37° C. and 5% $CO_2$. NB-1 was seeded in a 96-well plate at 20,000 cells/well, and different concentrations of compounds were added (40 μM was the highest concentration, diluted according to ¼, a total of 7 concentrations). After incubation for 3 days, 10 μL CCK8 reagent was added to each well. After incubation for 2 hours, OD450 was detected by a microplate reader, then the effect of the compound on cell viability, $IC_{50}$ value was calculated.

3.2 Evaluation Results

TABLE 8

Inhibitory activity of representative compounds on NB-1 cells

| Compound | NB-1 $IC_{50}$(nM) |
|---|---|
| A4-1a | 424 |
| A4-1i | 433 |
| B9-1e | 175 |
| Arctigenin | 2380 |
| A4-1d | 546 |
| B11-1b | 626 |
| B11-1c | 446 |

It can be seen from the evaluation results that the compounds of the present invention have a good effect of inhibiting the activity of NB-1 cells and can be used to prepare a medicament for treating neuroglioma.

4. Evaluation of the Effects of Compounds on the Vitality of Aging Human Fibroblasts (WI-38) and Mouse Osteoid Cells (MLO-Y4)

4.1 Experimental Methods 4.1.1 Selectivity Experiments of Compounds on WI-38 Normal Cells and Senescent Cells WI-38 cells were cultured in DMEM (high glucose, 4.5 g/L) culture medium (supplemented with 10% FBS, 1% PS).

The experimental testing steps for the effects of compounds on the viability of WI-38 senescent cells were as follows. WI-38 cells were seeded in a 96-well plate at 20,000 cells/well. After overnight, 200 nM doxorubicin was added to each well and incubated for 3 days. Then the medium was replaced with normal culture medium. After 1 day of incubation, the culture medium was replaced with 200 nM doxorubicin and incubated for 3 days to successfully induce senescence of WI-38 cells. Subsequently, different concentrations of compounds were added (40 μM was the highest concentration, and diluted according to ¼, a total of 7 concentrations), and after co-incubation for 3 days, 10 μl of MTT (5 mg/ml) was added to each well and incubated for 4 hours. DMSO (150 μl) was added to each well after aspirating the culture medium. After incubation for 15 minutes with shaking, the OD490 was detected by using a microplate reader, and the effect of the compounds on cell viability, $IC_{50}$ value was calculated.

4.1.2 Selectivity Experiments of Compounds on MLO-Y4 Normal Cells and Senescent Cells MOL-Y4 cells were cultured in MEM culture medium (supplemented with 10% FBS, 1% PS).

The experimental steps for testing the effects of compounds on the viability of MOL-Y4 senescent cells were as follows. MOL-Y4 cells were seeded in a 96-well plate at 20,000 cells/well. After overnight, 100 nM doxorubicin was added to each well and incubated for 3 days. Then the medium was replaced with normal culture medium. After 1 day of incubation, the culture medium was replaced with 100 nM doxorubicin and incubated for 3 days to successfully induce senescence of MOL-Y4 cells. Subsequently, different concentrations of compounds were added (40 μM was the highest concentration, and diluted according to ¼, a total of 7 concentrations), and after co-incubation for 3 days, 10 μl of MTT (5 mg/ml) was added to each well and incubated for 4 hours. DMSO (150 μl) was added to each well after aspirating the culture medium. After incubation for 15 minutes with shaking, the OD490 was detected by using a microplate reader, and the effect of the compounds on cell viability, $IC_{50}$ value was calculated.

4.2 Evaluation Results

TABLE 9

Inhibitory effects of representative compounds on senescent cell viability

| Compound | WI-38 $IC_{50}$(nM) | MOL-Y4 $IC_{50}$(nM) |
|---|---|---|
| A4-1a | 38 | 40 |
| A4-1e | 1000 | 150 |
| ABT263 | 5600 | 235 |

Note: BCL-2 inhibitor ABT263 is a positive control.

It can be seen from the evaluation results that the compounds of the present invention can effectively inhibit the vitality of senescent cells. Since senescent cells do not have the ability to replicate, the reduction in cell viability means drug-induced apoptosis, that is, elimination. The compound of the present invention is better than the existing senescent cell scavenger ABT263 in eliminating senescent cells, and can be used to prepare a medicament for treating aging-related disease.

5. Evaluation of the Efficacy of Compounds on Osteoarthritis Model Mice 5.1 Experimental Principles and Methods Principle Resection of the medial meniscal ligament in mouse knees leads to knee meniscal destabilization, thereby inducing osteoarthritis in mice. An important clinical feature of osteoarthritis is joint pain, joint swelling, and limited mobility, so increasing pain sensitivity in osteoarthritis mouse is considered to have a therapeutic effect on osteoarthritis. Therefore, in this experiment, medial meniscus ligament resection was performed on $C_{57}$ mice to induce osteoarthritis in mice, and then drugs were injected subcutaneously into the knee joint on the operated side for eight weeks, and then pain sensitivity in osteoarthritic mice was detected by the hot plate test. The mouse knee joints were subjected to safranin O-fast green staining test to evaluate the therapeutic effect of the compound on osteoarthritis.

Method

1) Osteoarthritis model mice with destabilization of the medical meniscus (DMM) caused by medial meniscus ligament resection were used.

A. After anesthetizing 8-week-old C57 male mice, 75% ethanol was used to disinfect the mouse's right hind limb knee joint, and then the skin at the right knee joint was cut a 2 cm incision. Then, the muscles and synovial tissue on the medial side of the right knee joint were bluntly separated, and then the patella was displaced laterally using a blunt instrument to expose the joint cavity. The fat pad in the joint cavity was bluntly separated under an operating microscope to expose the medial meniscus ligament of the knee joint. The medial meniscus ligament was then cut off with a surgical blade, and it could be visibly felt that the medial meniscus was free (it could slide). The patella was then repositioned and the muscles and skin were sutured in sequence. Penicillin (100 mg/kg/day) was given intraperitoneally for 3 days after surgery to prevent bacterial infection.

B. On the day after surgery, the mice in the administration group were given compound A4-1a (2 mM, 50 μL/mouse) after they woke up, and the other groups were given solvent (physiological saline). Thereafter, the drug was administered every other day for 8 weeks.

2) After the last injection, a hot plate experiment was performed the next day to detect the pain sensitivity of the mice. The experimental method was as follows. The mice were adapted to the experimental environment for 30 minutes. The mice were placed on a hot plate at 52° C. The time when the mice first appeared behaviors such as licking the soles of their feet and jumping was recorded. Each mouse was tested three times. Then the statistical analysis was performed.

3) After the hot plate experiment, the mouse was suffocated to death with carbon dioxide, and then the right hind limb knee joint of the mouse (the joint where the surgery was performed) was fixed in paraformaldehyde, followed by decalcification, paraffin sectioning, and the knee joint tissue of the mouse was stained with safranin O-fast green or subjected to p16 immunostaining, and the morphology of the knee joint cartilage tissue was observed under a microscope. The osteoarthritis score (OA Score) and p16 positive area were measured, and the statistical analysis was performed.

5.2 Evaluation Results

Figure 2:
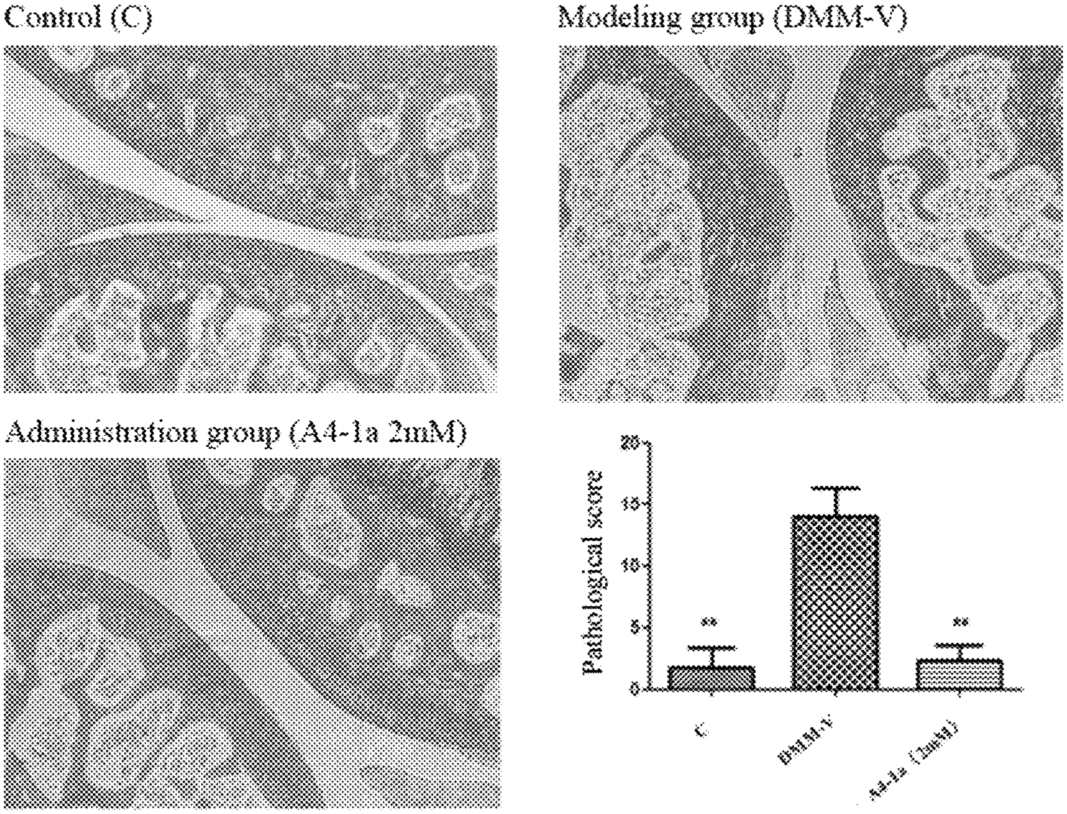
FIG. 2 shows pictures of mouse joint pathological morphology and OA scores.
Figure 3:
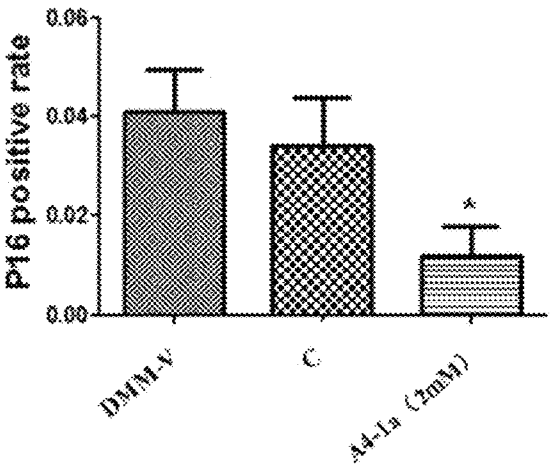
FIG. 3 shows the p16 positive rate of articular cartilage immunohistochemistry.

FIG. 1 shows the reaction time of mouse in the hot plate experiment. FIG. 2 shows the pathological morphological pictures and OA scores of mouse joints. FIG. 3 shows the p16 positive rate of articular cartilage immunohistochemistry.

It can be seen from the evaluation results that the compound A4-1a of the present invention can significantly reduce the reaction time of osteoarthritis mice in the hot plate test, indicating that it is helpful for the recovery of the mice's exercise ability. In pathological evaluation, A4-1a can restore the smoothness and integrity of the damaged articular cartilage surface, reduce the pathological score of mouse joint tissue, and reduce the expression of the aging marker p16 in cartilage, indicating that compound A4-1a can effectively eliminate damage-induced senescent cells and improve the osteoarticular pathological morphology.

6. Evaluation of the Efficacy of Compounds in Mice with Bleomycin-Induced Idiopathic Pulmonary Fibrosis (IPF)

6.1 Experimental Methods

Experimental animals: male C57 mice, 24-28 g/mouse, 70 mice.

Bleomycin-induced pulmonary fibrosis model and administration: for 65 C57 mice, bleomycin was administered via oropharyngeal inhalation at 2 U/kg after anesthesia to create an IPF model. Before administration and on day 5 after the administration of the drug, the corresponding weight of each mouse was measured, and mice with significant weight loss were selected as the standard for successful modeling. 20 mice with successful modeling were selected and divided into 2 groups (solvent group-solvent for administration, A4-1a-30 group-30 mg/kg/day A4-1a for oral administration, A4-1a-10 group-10 mg/kg/day A4-1a for oral administration), and five C57 mice were selected as a normal mouse control. Administration was carried out on day 5 for a total of 14 days. The body weight and survival rate of mice were recorded daily.

Treatment of mouse organs: On the 15th day after administration, the mice were anesthetized and weighed. The mice were sacrificed, and the mouse lung tissue was removed and weighed. The mouse lung index was calculated by: mouse lung tissue weight/mouse body weight×1000. The middle ⅓ of the lung tissue was taken out and fixed in 4% paraformaldehyde for subsequent paraffin sectioning and Masson staining.

Masson staining of mouse lung tissue: the mouse lung tissue was paraffin-embedded according to conventional methods, and sections were subjected to Masson staining. The specific procedures were as follows. The sections were dewaxed and then stained with hematoxylin for 2 minutes, distilled water for 2-3 seconds, differentiation solution for 2-3 seconds, distilled water for 2-3 seconds, blue promoting solution for 2-3 seconds, distilled water for 2-4 minutes, magenta 6 minutes, distilled water 2-3 seconds, phosphomolybdic acid 2-3 seconds, aniline blue 2 minutes, 1% acetic acid 2-3 seconds, 100% ethanol 2 minutes, repeated 100% ethanol 2 minutes, xylene 2 minutes, repeated xylene for 2 minutes, and then sealed with neutral gum.

6.2 Evaluation Results

Figure 4:
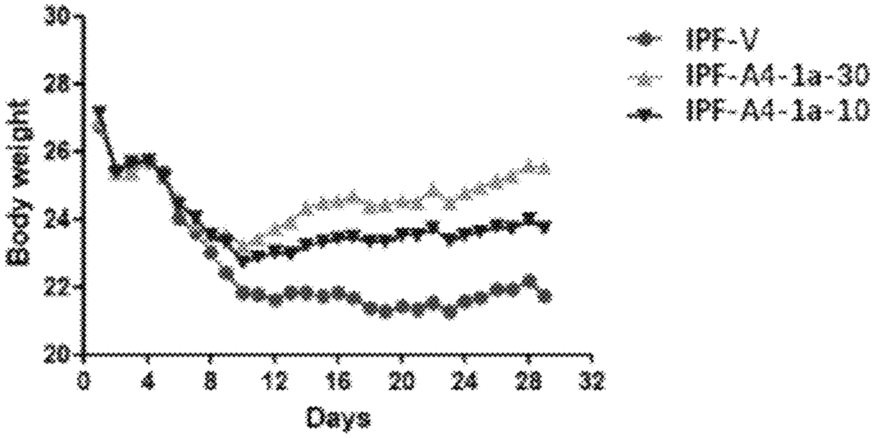
FIG. 4 shows the changes in body weight of IPF mouse after administration.
Figure 5:
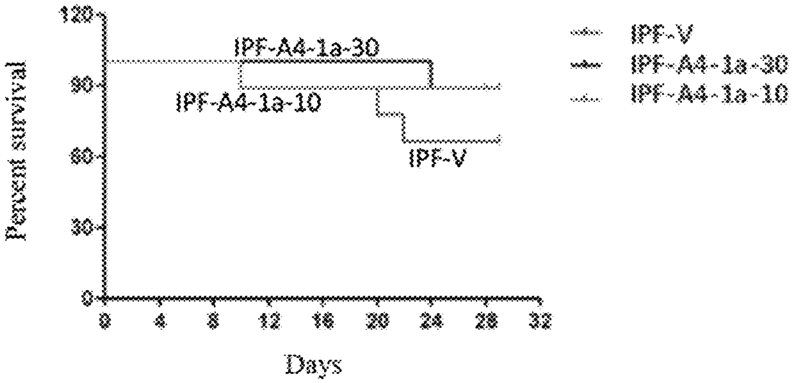
FIG. 5 shows the changes in survival rate of mouse after administration.
Figure 6:
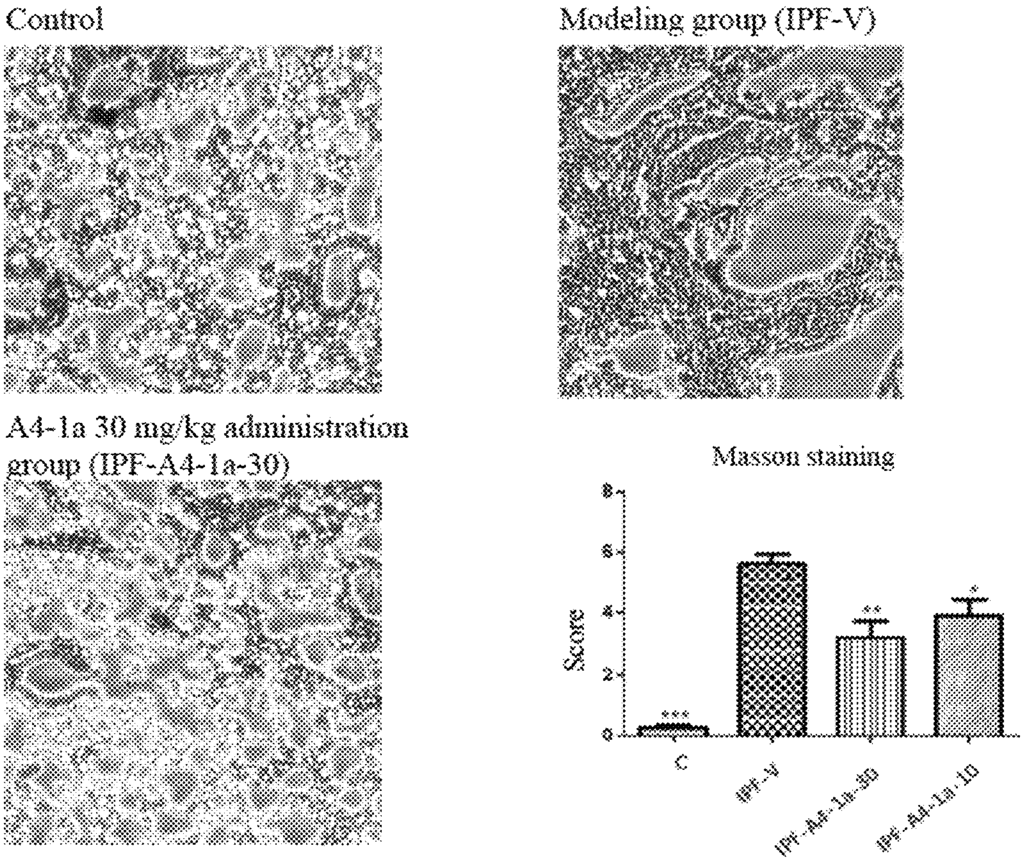
FIG. 6 shows Masson staining and pathological scoring of section of the mouse lung tissue.
Figure 7:
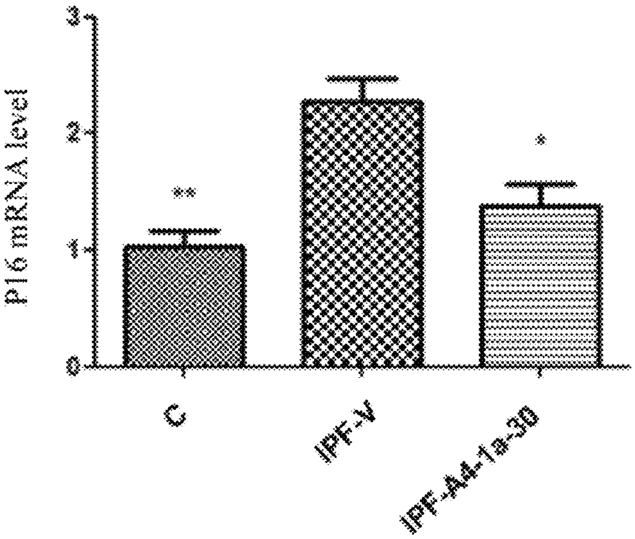
FIG. 7 shows the level of the aging marker p16 gene in mouse lung tissue.
Figure 8:
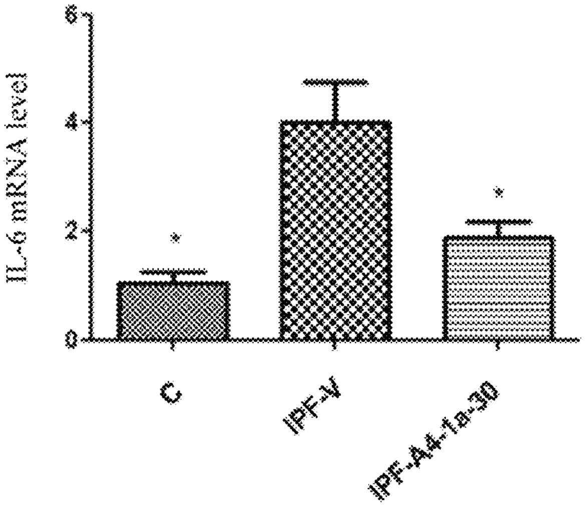
FIG. 8 shows IL-6 gene level in mouse lung tissue SASP.

FIG. 4 shows the changes in body weight of IPF mice after administration; FIG. 5 shows the changes in survival rate of mice after administration; FIG. 6 shows Masson staining and pathological scores of mouse lung tissue sections; FIG. 7 shows the changes in aging marker p16 gene levels of mouse lungs tissue; and FIG. 8 shows IL-6 gene levels in mouse lung tissue SASP.

It can be seen from the evaluation results that compound A4-1a of the present invention can significantly slow down the weight loss of IPF mice, improve the survival rate of mice, reduce the degree of fibrosis in lung tissue sections (Masson staining score), and reduce the level of aging marker p16 and the aging-related secretory phenotype IL-6, indicating that the compound has a very significant effect on improving or treating the aging-related disease IPF.

7. Evaluation of the Efficacy of Compound A4-1a on Mice with Alzheimer's Disease (AD)

7.1 Experimental Principles and Methods

In the present invention, APP/PS1 transgenic Alzheimer's disease (AD) model mice were used. This type of transgenic mice highly expresses chimeric mouse/human Swedish mutant APP (Mo/HuAPP695swe) and human-derived progerin 1 protein with deletion of exon 9 (presenilin, PS1- dE9). This type of transgenic mice will have significant AB deposition at 6 months of age and spatial memory impairment at 7 months of age. Therefore, six-month-old APP/PS1 transgenic AD mice were used in the present invention. Three months after oral administration (A4-1a, 30 mg/kg/day), the Morris water maze test was used to detect the effect of A4-1a on memory impairment in transgenic mice. The negative mice of this type of mice were used as the control group to evaluate the therapeutic effect of A4-1a on Alzheimer's disease.

1) Breeding of APP/PS1 double transgenic AD model mice. To identify the transgenic type of offspring mice, the mice were tail-docked and then PCR was used to identify the APP/PS1 gene sequence of the mice. Non-transgenic mice were used as negative control mice in the experiment. Mice were raised under standard conditions (12/12 h light/dark cycle, adequate water and food, constant temperature of 22° C., and 60% humidity).

2) Administration for AD model mice: When the mice were 6 months old, 20 transgenic mice were randomly divided into 2 groups (transgenic solvent group, transgenic A4-1a-30 mg/kg/day dose group), and 10 non-transgenic mice were served as negative control. A4-1a was dissolved in 2% Tween 80 and administered intragastrically for 90 days, and then behavioral testing (Morris water maze test) was carried out.

3) The mice were trained three times a day for 8 days. After training the mouse to face the pool wall and placing it in the water, it had 60 seconds to find the platform location. The mouse stayed on the platform for 15 seconds to help it remember the platform location. During this period, the time it took for the mouse to find the platform is recorded, which was the latency period. On the 9th day, after three trainings, the mice were subjected a platform-finding experiment. The platform submerged under the water was removed. The mice were then allowed to search for the platform in the pool for 90 seconds. The number of times the mice traversed the platform was recorded as an evaluation index of their memory. The higher number of times indicated that their memory was better. All animal experiments were conducted in strict compliance with the Regulations for the Administration of Laboratory Animals.

7.2 Evaluation Results

Figure 9:
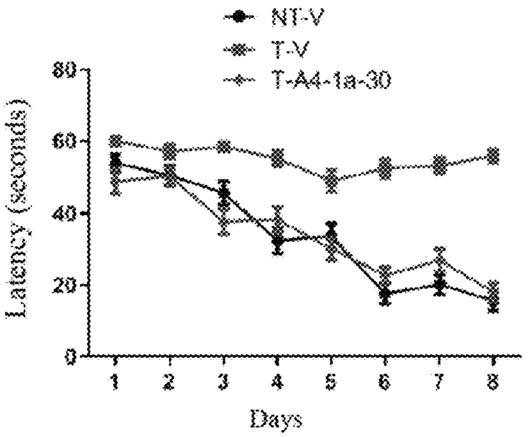
FIG. 9 shows the effect of compound A4-1a on the latency of transgenic AD mouse in the water maze test.
Figure 10:
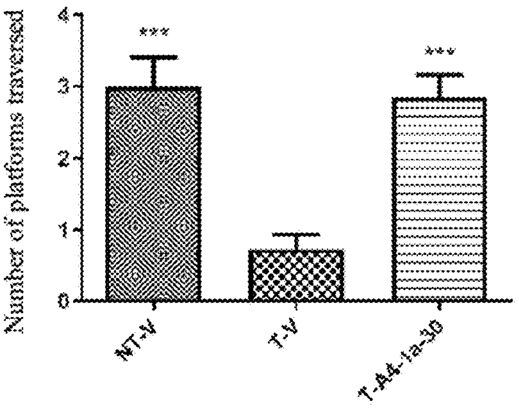
FIG. 10 shows the effect of compound A4-1a on the number of platform crossed by transgenic AD mice.

As shown in FIGS. 9 and 10, the latency period of transgenic mice (T-V) is significantly longer than that of non-transgenic mice (NT-V), and the number of platform crossings is significantly less than that of non-transgenic mice, indicating that the memory of transgenic mice is significantly impaired, indicating that its AD model is correct. The latency period of transgenic mice (T-A4-1a-30) orally administered 30 mg/kg/day A4-1a was significantly shorter than that of solvent-treated transgenic mice, and the number of platform crossings was significantly more than that of solvent-treated transgenic mice, indicating that A4-1a can reverse the memory impairment in transgenic mice. These results indicate that A4-1a is highly effective in treating Alzheimer's disease.

8. Evaluation of the Efficacy of Compound A5 on Mice with Liver Fibrosis Induced by Carbon Tetrachloride 8.1 Experimental Methods Experimental animals: 40 male C57 mice, 8 weeks old.

Modeling and administration: 400 μL of carbon tetrachloride ($CCl_4$) was added to 3.6 mL of olive oil, mixed well, and then injected intraperitoneally at 0.1 mL/20 g, twice a week for six weeks. Six weeks later, 30 mice were divided into 3 groups, with 10 mice in each group. They were given physiological saline by gavage, 1 mg/kg A5 and 3 mg/kg A5. In addition, 10 mice that were not induced were given physiological saline as a control group. After 3 weeks of continuous administration, the mice were sacrificed, and the livers were removed, weighed, fixed and embedded, and the remaining liver tissue was cryopreserved for detection of hydroxyproline content.

Masson staining of mouse liver tissue: The mouse liver tissue was paraffin-embedded according to conventional methods, and sections were subjected to Masson staining. The specific procedures were as follows. The sections were dewaxed and then stained with hematoxylin for 2 minutes, distilled water for 2-3 seconds, differentiation solution for 2-3 seconds, distilled water for 2-3 seconds, blue promoting solution for 2-3 seconds, distilled water for 2-4 minutes, magenta 6 minutes, distilled water 2-3 seconds, phosphomolybdic acid 2-3 seconds, aniline blue 2 minutes, 1% acetic acid 2-3 seconds, 100% ethanol 2 minutes, repeated 100% ethanol 2 minutes, xylene 2 minutes, repeated xylene for 2 minutes, and then sealed with neutral gum.

Detection of hydroxyproline content in mouse liver tissue: A hydroxyproline detection kit (Nanjing Jiancheng Bioengineering Institute) was used. A brief introduction was as follows. Weigh 40 mg of liver tissue, add 0.5 mL of alkali lysis solution, and hydrolyze at 95° C. for 20 minutes, then add 5 μL of pH indicator, mix well, then add 0.5 ml of pH-adjusting solution A, and mix to turn red. Slowly add pH-adjusting solution B until the red color disappears and turns into yellow-green. Then add 5 mL of deionized water and mix well, then add 20 mg of activated carbon and mix well, centrifuge at 3500 rpm for 10 minutes, and take the supernatant for hydroxyproline determination. According to the instructions of the kit, add reaction reagent I and react for 10 minutes, then add reaction reagent II and react for 5 minutes. Finally, add reaction reagent III and react at 60° C. for 15 minutes. Then centrifuge at 3500 rpm for 15 minutes. Absorbance values of the supernatant at a wavelength of 550 nm were determined using a microplate reader. The hydroxyproline content per 100 mg of liver tissue was then calculated.

8.2 Evaluation Results

Figure 11:
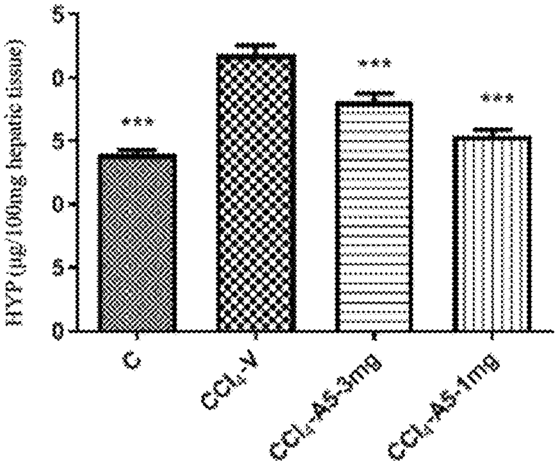
FIG. 11 shows the effect of compound A5 on the hydroxyproline content in the liver tissue of mouse with carbon tetrachloride-induced liver fibrosis.

As shown in FIG. 11, the hydroxyproline (HYP) content in the livers of mice induced by $CCl_4$ and given solvent is higher than that of mice in the normal control group, which is statistically significant. Compound A5 administered intragastrically at 1 mg/kg/day and 3 mg/kg/day can significantly reduce the increase in hydroxyproline content induced by $CCl_4$, which is statistically significant.

Figure 12:
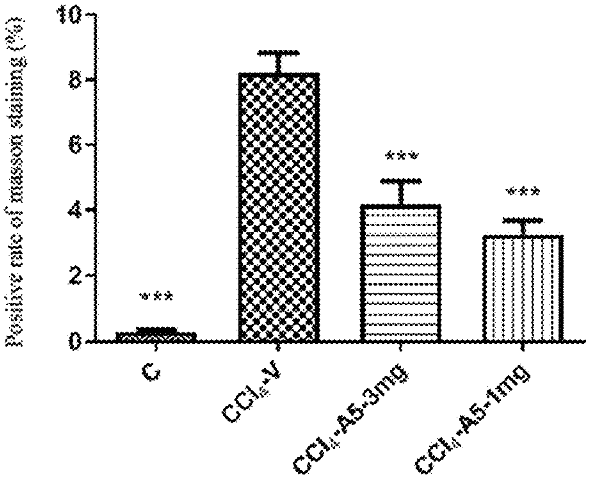
FIG. 12 shows the effect of compound A5 on the positive rate of Masson staining in the liver of mouse with liver fibrosis.

As shown in FIG. 12, the positive rate of Masson staining in liver tissue of mice induced by $CCl_4$, that is, the area of liver fibrosis is significantly increased compared with the mice in the normal group, which is statistically significant. Compound A5 administered intragastrically at 1 mg/kg/day and 3 mg/kg/day can significantly reduce the degree of liver fibrosis in mice, which is statistically significant.

The above results show that compound A5 has a good effect on improving or treating liver fibrosis.

9. Evaluation of the Efficacy of Compound A5 on Mice with Oxazolone-Induced Inflammatory Bowel Disease 9.1 Experimental Methods Experimental animals: 30 male C57 mice, 8 weeks old.

Modeling and administration: 3% Oxazolone was dissolved in the solvent (acetone:olive oil, 1:4). After the mouse was anesthetized, the hair on the shoulder of the mouse was removed, and then 150 μL of Oxazolone with a mass fraction of 3% was added dropwise. On the 8th day after treatment, 1% Oxazolone was dissolved in a solvent (ethanol:sterilized water, 1:1). After the mice were anesthetized, 150 μL of 1% Oxazolone was administered rectally to create a model. The modeling mice were divided into two groups, with 10 mice in each group. One group was given compound A5 by gavage at 1 mg/kg/day, one group was given physiological saline, and the other group of 10 mice without modeling was used as a control group. Starting from the day of modeling, the weight of the mice was recorded every day. The feces of the mice were collected on the third day after rectal administration to observe the softness of the feces and whether there was bleeding. The mice were then sacrificed, and the mouse colon about 3 cm from the distal end was taken for fixation.

Mouse enteritis disease activity index score: Mice were scored based on the degree of weight loss of the mouse (0: normal; 1:1-5%; 2:6-10%; 3:11-18%; 4: >18%), the degree of the softness of the feces (0: normal; 2: soft; 4: diarrhea), and the degree of feces bleeding (0: normal; 2: occult blood; 4: bloody stool), then each score was added and divide by three.

Eosin-hematoxylin staining of mouse colon tissue: The mouse colon tissue was fixed, embedded in paraffin, sectioned, and stained with eosin-hematoxylin. Calculation method of mouse colon inflammation index is based on the integrity of mouse colon mucosa (0: normal; 1: mucosal damage; 2: submucosal damage; 3: muscle damage), the degree of inflammatory cell infiltration (0: normal; 1: massive infiltration of inflammatory cells in the mucosal layer; 2: infiltration of inflammatory cells into the submucosa; 3: infiltration of inflammatory cells into the muscular layer), and the degree of edema in the colon (0: normal; 1: mild edema; 2: moderate edema; 3: severe edema).

9.2 Evaluation Results

Figure 13:
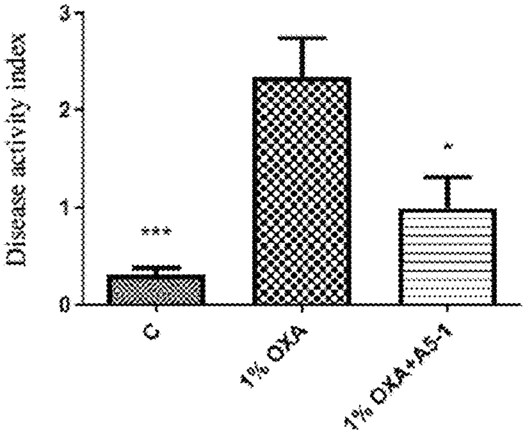
FIG. 13 shows the effect of compound A5 on disease activity index in mouse with oxazolone-induced enteritis.

As shown in FIG. 13, the disease activity index of Oxazolone-induced enteritis model mice is significantly higher than that of the normal group, and intragastric administration of Compound A5 (1 mg/kg/day) can significantly reduce the disease activity index of enteritis.

Figure 14:
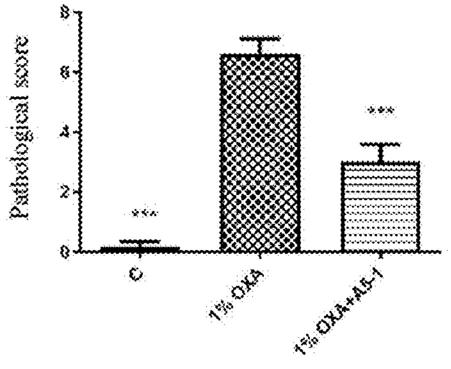
FIG. 14 shows the effect of compound A5 on colon pathology in mouse with oxazolone-induced enteritis.

As shown in FIG. 14, the colon pathology score of the Oxazolone-induced enteritis model mice is significantly higher than that of mouse in the normal control, and intragastric administration of A5 (1 mg/kg/day) can significantly reduce the colon pathology score.

The above results indicate that compound A5 has a significant effect on treating or alleviating inflammatory bowel disease.

Example 8 Pharmacokinetic Evaluation

1. Oral Pharmacokinetic Evaluation of Compound A4-1a and Arctigenin 1.1 Experimental Method Arctigenin and Compound A4-1a were administered orally at 30 mg/kg to overnight-fasted ICR mice (male, n=3/time point), respectively. The mice were fed 2 hours after administration. Samples were collected before administration and 1 h, 2 h, 4 h, and 8 h after administration. Blood was collected in centrifuge tubes pretreated with heparin sodium and bis(4-nitrophenyl)phosphate (BNPP). After centrifugation at 11,000 rpm for 5 min at 4° C., plasma was obtained and stored at −80° C. Next, 100 mL of methanol/acetonitrile (1:1, v/v) was added to 10 mL of plasma sample, precipitated, vortexed for 1 min, and centrifuged (11,000 rpm) for 5 min. A mixture of 20 mL of supernatant and 20 mL of methanol/acetonitrile (1:1, v/v) was taken to analyze the concentration of the compound by LC-MS/MS. Liver tissue was stored at −80° C. until analysis. After removal of contents, the colon was quickly washed with cold saline containing BNPP and stored at −80° C. until analysis. Analysis method: After 10 times the weight of MeOH/ACN (1:1, v/v) was added to the tissue samples, the homogenate was obtained by homogenizing for 120 s with a homogenizer at 50 Hz and then centrifuged (11000 rpm) for 5 min, and the supernatant was collected. 20 μL of the supernatant was redissolved in 20 μL of ACN/$H_2O$ (1:1, v/v), and the compound concentration was analyzed in LC-MS/MS.

1.2 Evaluation Results

Figure 15:
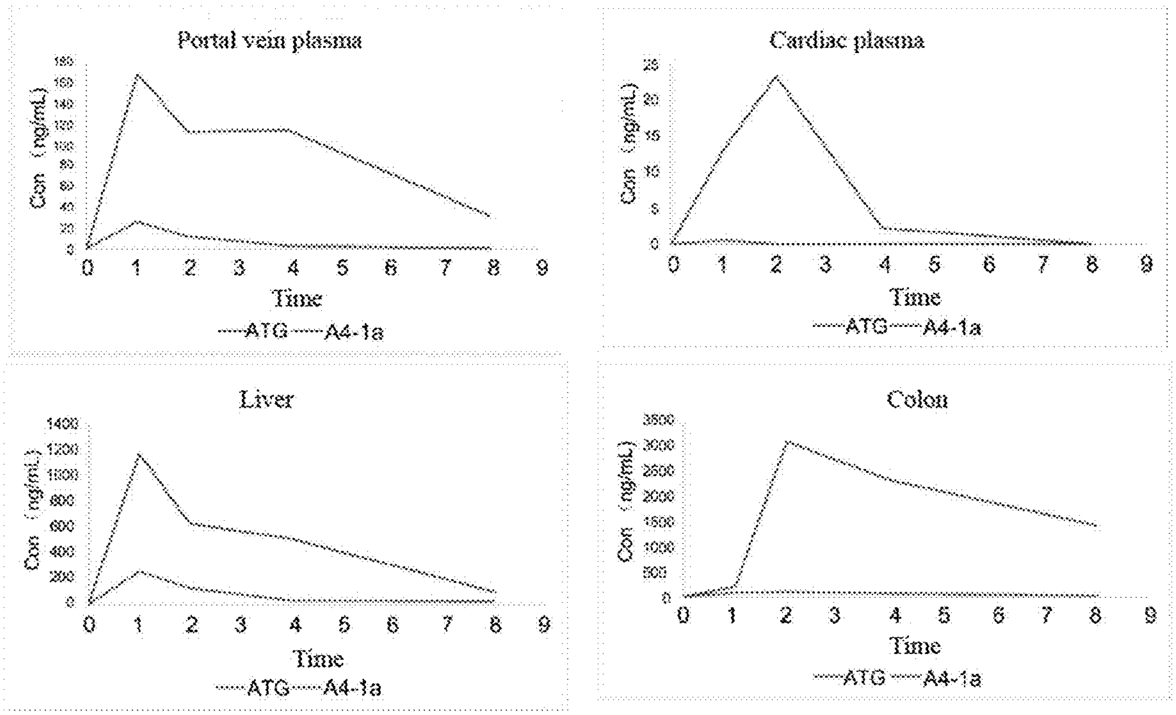
FIG. 15 shows the drug concentration/time change curves in plasma, liver, and colon tissue of mouse after oral administration of 30 mg/kg of Compound A4-1a and Arctigenin at 30 mg/kg.

FIG. 15 shows the change of drug concentration in plasma, liver, and colon tissue of the mouse over time after oral administration of Compound A4-1a and Arctigenin at 30 mg/kg.

It can be seen from the evaluation results that compared with Arctigenin, the compound A4-1a resulting from the structural modification shows significantly higher drug concentrations in plasma and tissues after oral administration of the same dose, indicating an unexpected improvement in the oral pharmacokinetic properties.

2. Evaluation of Oral Pharmacokinetics of Phosphate Prodrug A5 of Compound A4-1a 2.1 Experimental Methods Compound A5 (30 mg/kg) was administered orally to overnight fasted ICR mice (male, n=3/time point). The mice were fed 2 hours after administration. Samples were collected before administration and 1 h, 2 h, 4 h, and 8 h after administration. Blood was collected in centrifuge tubes pretreated with heparin sodium and bis(4-nitrophenyl)phosphate (BNPP). After centrifugation at 11,000 rpm for 5 min at 4° C., plasma was obtained and stored at −80° C. Next, 100 mL of methanol/acetonitrile (1:1, v/v) was added to 10 mL of plasma sample, precipitated, vortexed for 1 min, and centrifuged (11,000 rpm) for 5 min. A mixture of 20 mL of supernatant and 20 mL of methanol/acetonitrile (1:1, v/v) was taken to analyze the concentrations of compound A5 and compound A4-1a by LC-MS/MS. Heart (blood emptying), liver, and lung tissues were stored at −80° C. until analysis. After removal of contents, the duodenum and colon were quickly washed with cold saline containing BNPP and stored at −80° C. until analysis. Analysis method: After 10 times the weight of MeOH/ACN (1:1, v/v) was added to the tissue samples, the homogenate was obtained by homogenizing for 120 s with a homogenizer at 50 Hz and then centrifuged (11000 rpm) for 5 min, and the supernatant was collected. 20 μL of the supernatant was redissolved in 20 μL of ACN/$H_2O$ (1:1, v/v), and the concentrations of compound A5 and compound A4-1a were analyzed by LC-MS/MS.

2.2 Evaluation Results

Figure 16:
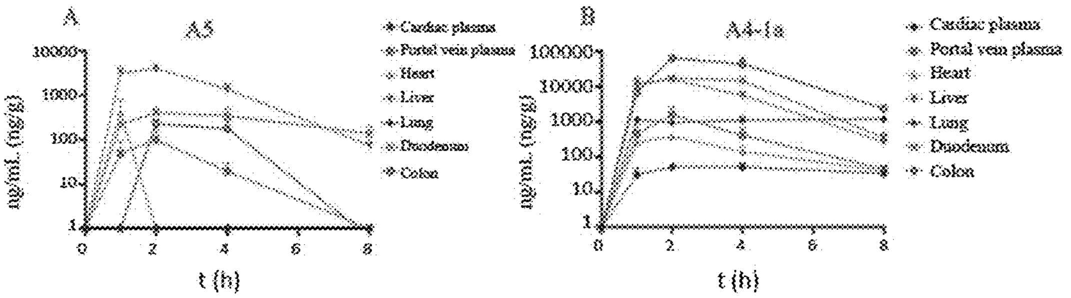
FIG. 16 shows the drug concentration/time change curve of prodrug A5 (A) and prototype A4-1a (B) in plasma and tissue of mouse after oral administration of 30 mg/kg of compound A5.

FIG. 16 shows the changes in drug concentration of prodrug A5 (A) and prototype A4-1a (B) in plasma and tissue of the mouse over time after oral administration of 30 mg/kg of compound A5.

It can be seen from the evaluation results that the phosphate prodrug A5 can efficiently be metabolized to the prototype compound A4-1a in the body after oral administration, and has a good drug concentration in plasma and various tissues. Therefore, it also has potential application value in the preparation of a medicament for preventing or treating the diseases described in the present invention.

In summary, the present invention is based on the structural modification of Arctigenin to obtain the compounds of formula I and produces unexpected effects. The Complex I activity is improved; or the tumor cell-inhibiting activity is improved; or the senescent cell clearance activity is improved; or the oral pharmacokinetic property is improved, or a very significant efficacy is demonstrated in animal models of disease. Thus the compounds of the present invention have good potential for application in the prevention and/or treatment of diseases associated with elevated mitochondrial respiratory chain complex I activity or expression, or enhanced mitochondrial oxidative phosphorylation.

The invention claimed is:

1. A compound represented by formula I, or an enantiomer, diastereomer, racemic mixture, deuterated compound or pharmaceutically acceptable salt thereof, (I)

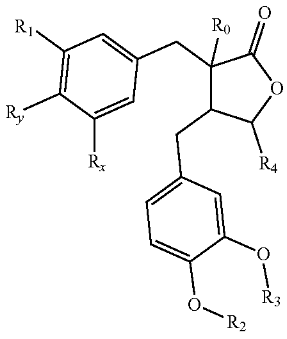

wherein, $R_x$ is hydrogen;

$R_0$ is halogen, $C_1$-$C_6$ alkyl, hydroxyl-substituted $C_1$-$C_6$ alkyl, or $C_1$-$C_6$ haloalkyl;

$R_1$ is $C_1$-$C_6$ alkoxy, or —O-L-G; wherein, L is a $C_{1-6}$ alkylene, a hydrogen atom of the alkylene is optionally substituted by hydroxyl in a manner and number allowed by the chemical bond; G is $C_1$-$C_6$ haloalkyl or $C_{6-10}$ aryl; the aryl is unsubstituted or substituted by 1 or 2 groups selected from the group consisting of halogen, $C_1$-$C_6$ alkyl, and $C_1$-$C_6$ haloalkyl;

$R_2$ and $R_3$ are each independently $C_1$-$C_6$ alkyl;

$R_4$ is hydrogen;

Ry is hydroxyl or

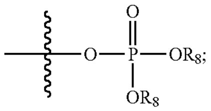

and $R_8$ is hydrogen.

2. The compound of claim 1, or an enantiomer, diastereomer, racemic mixture, deuterated compound or pharmaceutically acceptable salt thereof, wherein the compound has the following formula (IIa):

(IIa)

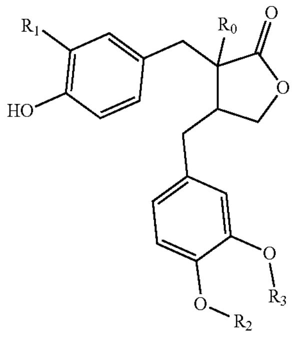

wherein each substituent is defined as in claim 1.

3. The compound of claim 1, or an enantiomer, diastereomer, racemic mixture, deuterated compound or pharmaceutically acceptable salt thereof, wherein the compound has the following formula (IIb):

(IIb)

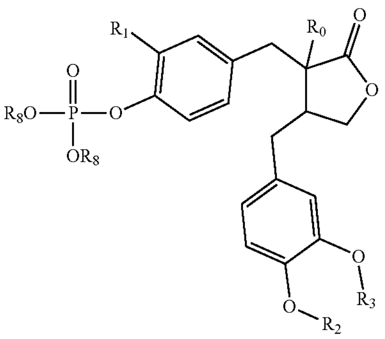

wherein each substituent is defined as in claim 1.

4. The compound of claim 1, or an enantiomer, diastereomer, racemic mixture, deuterated compound or pharmaceutically acceptable salt thereof, wherein $R_1$ is $C_1$-$C_4$ alkoxy or —O-L-G; wherein L is $C_{1-4}$ alkylene, and one hydrogen atom on the alkylene group is substituted by hydroxyl in a manner allowed by chemical bond; G is $C_1$-$C_4$ haloalkyl or phenyl; the phenyl is unsubstituted or substituted by one $C_1$-$C_6$ haloalkyl.

5. The compound of claim 1, or an enantiomer, diastereomer, racemic mixture, deuterated compound or pharmaceutically acceptable salt thereof, wherein $R_y$ is hydroxyl or —$OP(O)(OH)_2$;

$R_0$ is $C_1$-$C_6$ alkyl;

$R_2$ and $R_3$ are each independently $C_1$-$C_4$ alkyl;

$R_1$ is $C_1$-$C_4$ alkoxy or —O-L-G; wherein L is a $C_{1-4}$ alkylene; and G is a phenyl or $C_1$-$C_4$ haloalkyl.

6. A compound, or an enantiomer, diastereomer, racemic mixture, deuterated compound or pharmaceutically acceptable salt thereof, wherein the compound is selected from the group consisting of

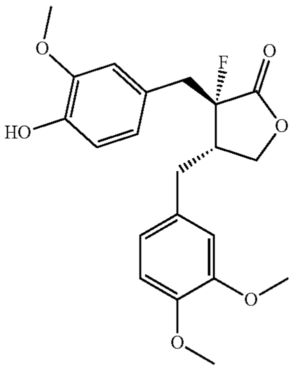
,
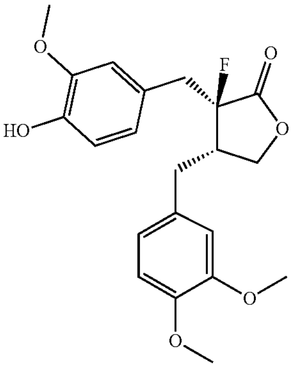
,
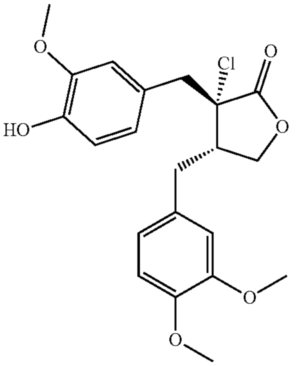
,
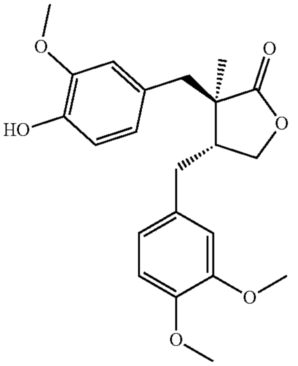
,
-continued
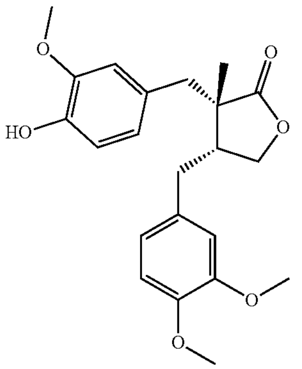
,
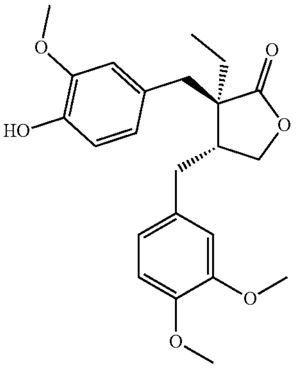
,
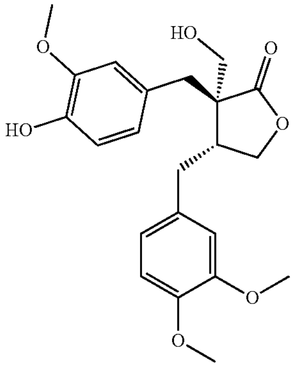
,
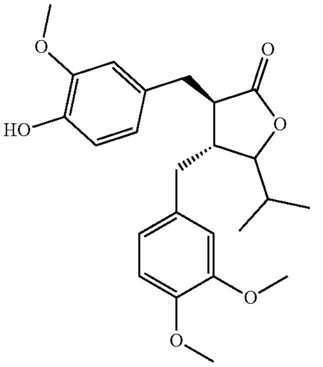
, -continued
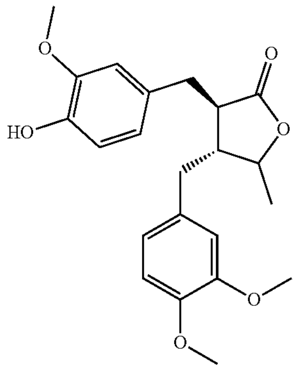
,
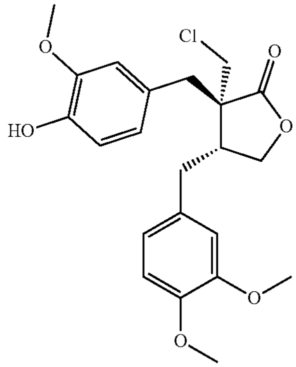
,
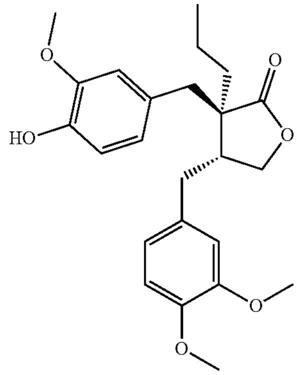
,
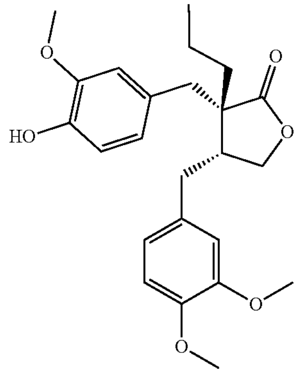
,
-continued
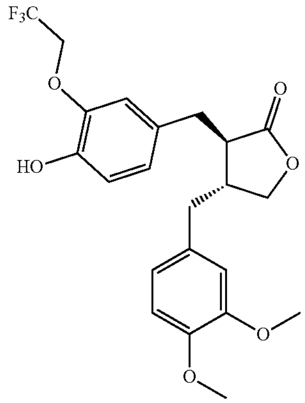
,
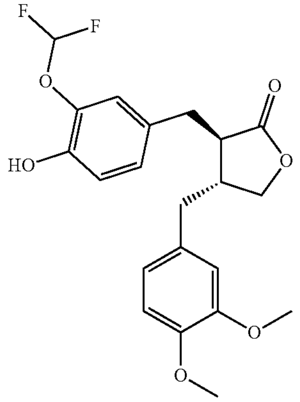
,
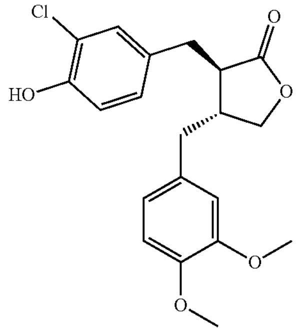
,
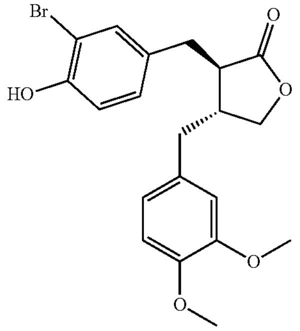
, -continued
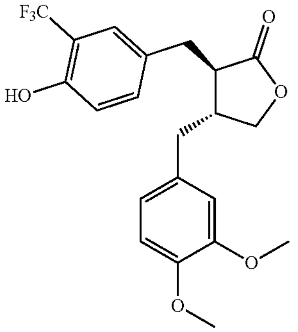
,
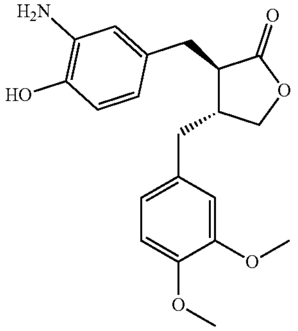
,
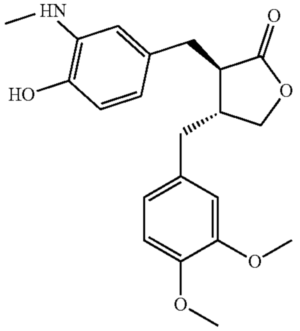
,
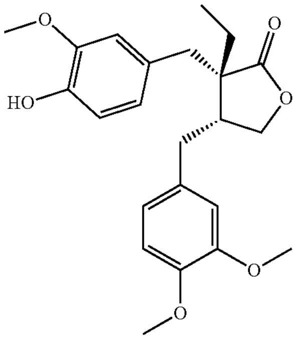
,
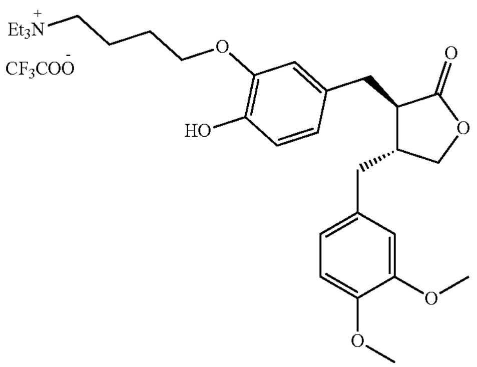
,
-continued
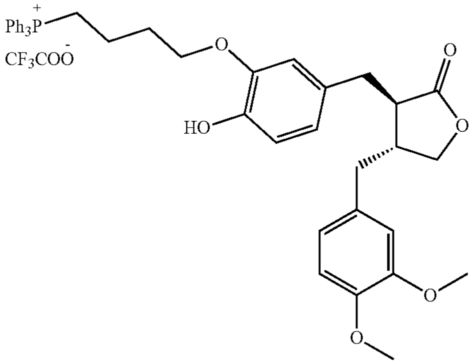
,
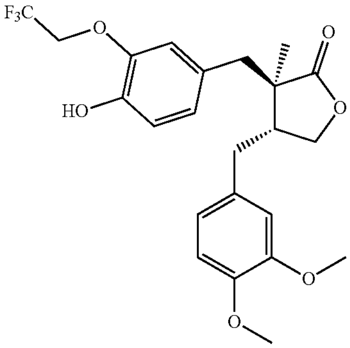
,
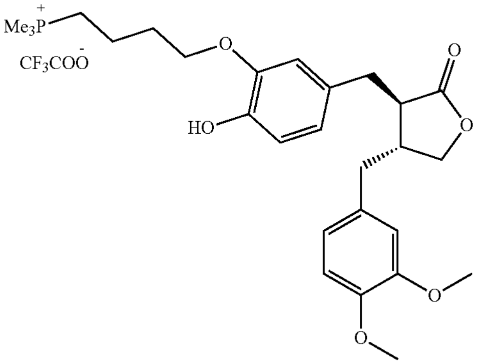
,
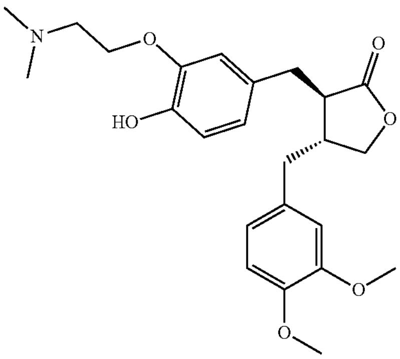
, -continued
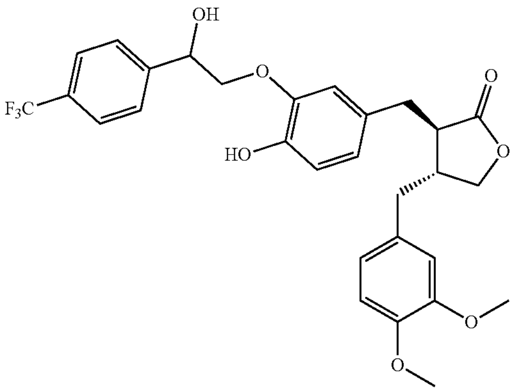
,
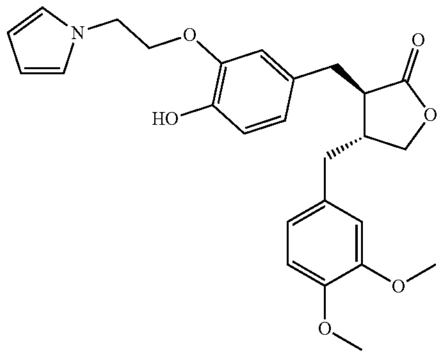
,
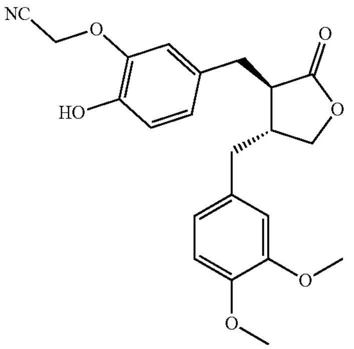
,
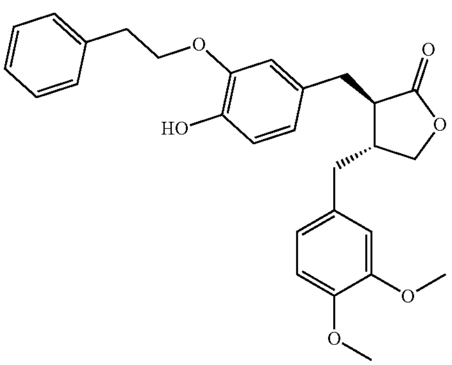
,
-continued
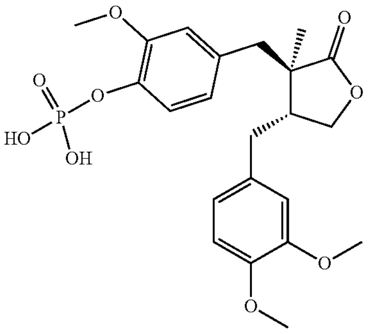
,
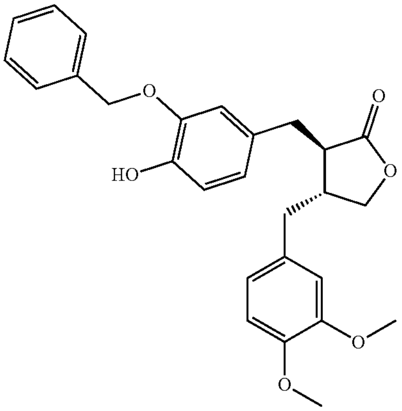
,
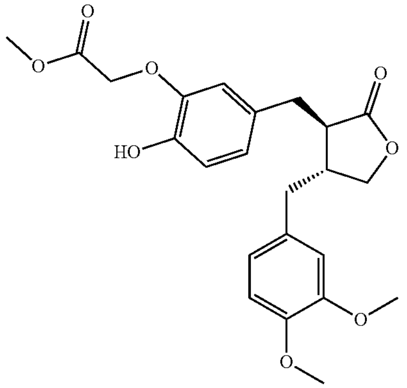
,
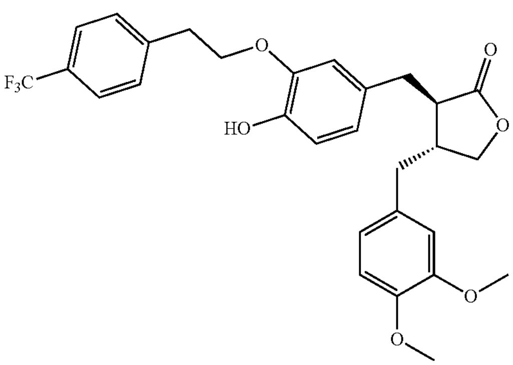
, -continued
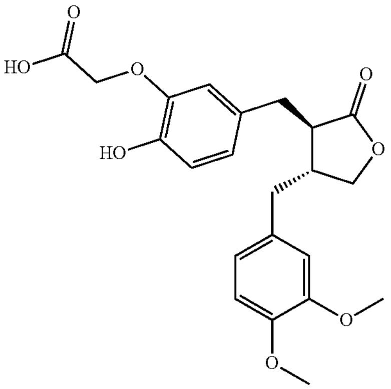
,
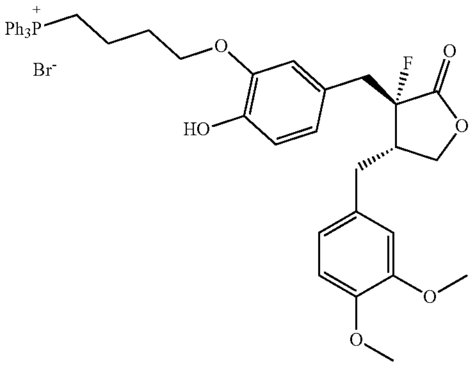
,
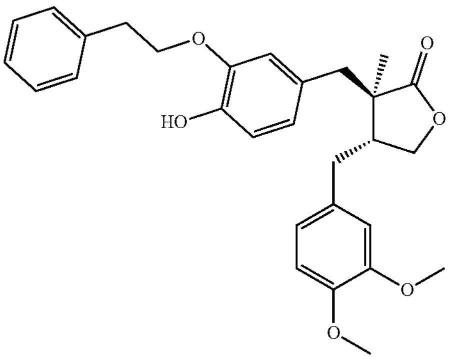
,
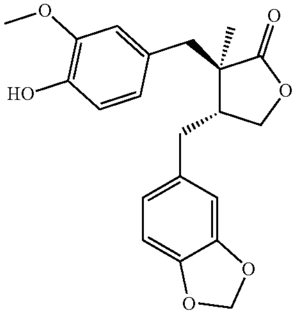
,
-continued
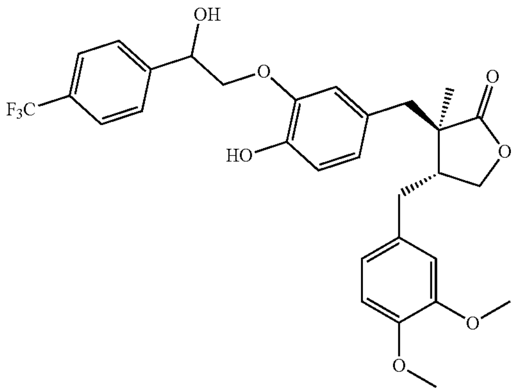
,
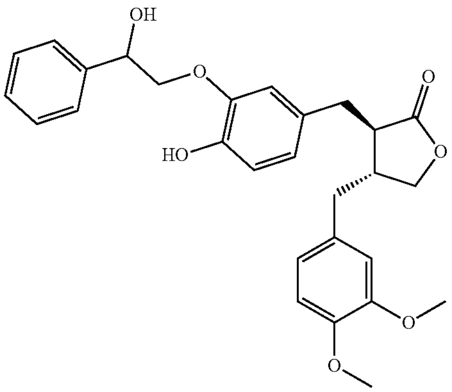
,
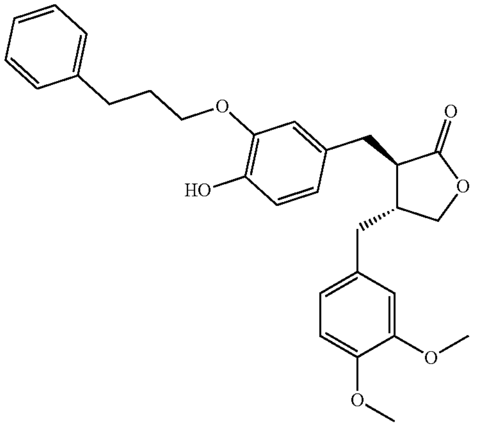
,
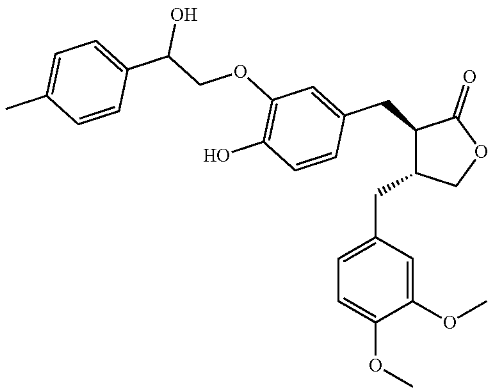
, -continued

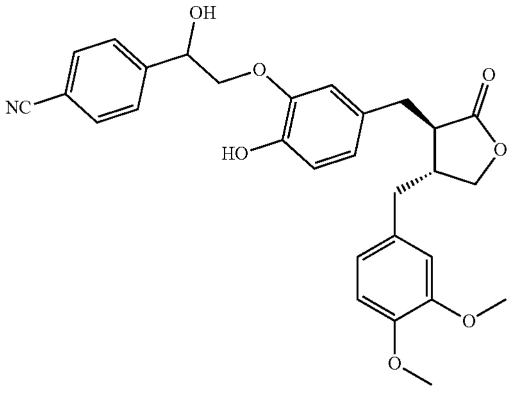

,

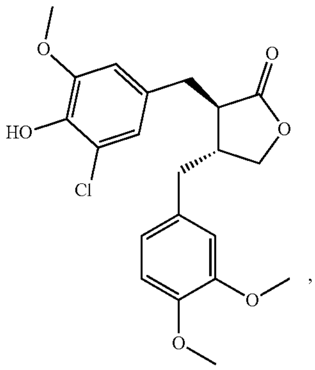

,

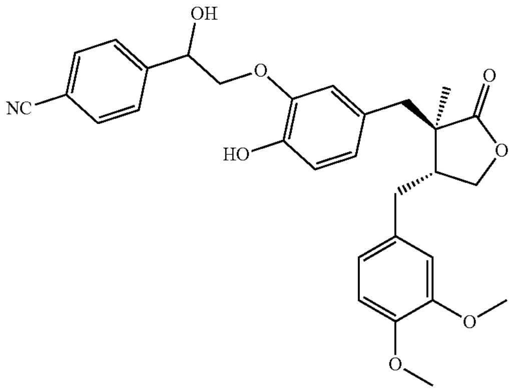

,

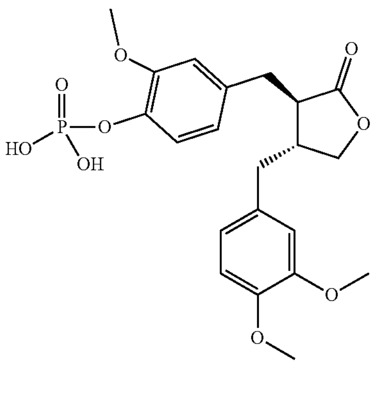

,

-continued

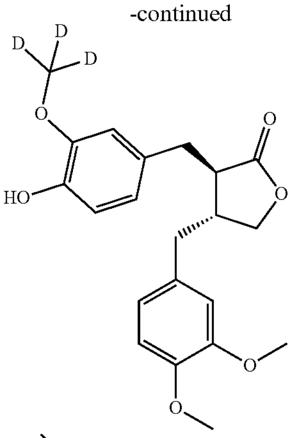

, and

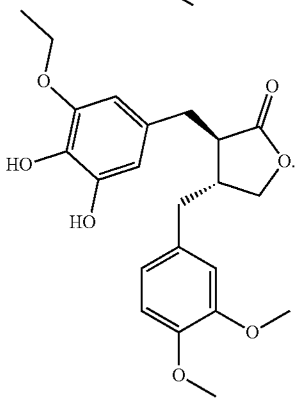

.

7. A pharmaceutical composition, comprising the compound of claim 1, or an enantiomer, diastereoisomer, racemic mixture, deuterated compound or pharmaceutically acceptable salt thereof; and a pharmaceutically acceptable carrier.

8. A method for treating a disease associated with increased activity or expression of mitochondrial respiratory chain complex I or a disease associated with enhanced mitochondrial oxidative phosphorylation comprising administering the compound of claim 1, or an enantiomer, diastereoisomer, racemic mixture, deuterated compound or pharmaceutically acceptable salt thereof to a subject in need thereof.

9. The method of claim 8, wherein the disease is a tumor selected from the group consisting of acute myeloid leukemia, neuroglioma, lymphoma, pancreatic cancer, uterine cancer, breast cancer, non-small cell lung cancer, and hepatocellular carcinoma.

10. The method of claim 8, wherein the disease is related to cell senescence and selected from the group consisting of organ fibrosis disease, chronic lung disease, chronic kidney disease, chronic liver disease, osteoarthritis, Alzheimer's disease, Parkinson's disease, Huntington's disease, amyotrophic lateral sclerosis, multiple sclerosis, inflammatory bowel disease, atherosclerosis, glaucoma, cataracts, macular degeneration, diabetes, diabetic retinopathy, pigmentation, and sarcopenia.

11. The method of claim 10, wherein the organ fibrosis disease is pulmonary fibrosis, liver fibrosis or renal fibrosis; the inflammatory bowel disease is ulcerative colitis or Crohn's disease.

12. The method of claim 11, wherein the pulmonary fibrosis is idiopathic pulmonary fibrosis.

13. A method for inhibiting mitochondrial respiratory chain complex I comprising administering the compound of claim 1, or an enantiomer, diastereoisomer, racemic mixture, deuterated compound or pharmaceutically acceptable salt thereof, to a subject in need thereof.

14. A pharmaceutical composition, comprising the compound of claim 6, or an enantiomer, diastereoisomer, racemic mixture, deuterated compound or pharmaceutically acceptable salt thereof; and a pharmaceutically acceptable carrier.

15. A method for treating a disease associated with increased activity or expression of mitochondrial respiratory chain complex I or a disease associated with enhanced mitochondrial oxidative phosphorylation comprising administering the compound of claim 6, or an enantiomer, diastereoisomer, racemic mixture, deuterated compound or pharmaceutically acceptable salt thereof, to a subject in need thereof.

16. The method of claim 15, wherein the disease is a tumor selected from the group consisting of acute myeloid leukemia, neuroglioma, lymphoma, pancreatic cancer, uterine cancer, breast cancer, non-small cell lung cancer, and hepatocellular carcinoma.

17. The method of claim 15, wherein the disease is related to cell senescence and selected from the group consisting of organ fibrosis disease, chronic lung disease, chronic kidney disease, chronic liver disease, osteoarthritis, neurodegenerative disease, inflammatory bowel disease, atherosclerosis, glaucoma, cataracts, macular degeneration, diabetes, diabetic retinopathy, pigmentation, and sarcopenia.

18. The method of claim 17, wherein the organ fibrosis disease is pulmonary fibrosis, liver fibrosis or renal fibrosis;

the neurodegenerative disease is Alzheimer's disease, Parkinson's disease, Huntington's disease, amyotrophic lateral sclerosis, or multiple sclerosis;

the inflammatory bowel disease is ulcerative colitis or Crohn's disease.

19. The method of claim 18, wherein the pulmonary fibrosis is idiopathic pulmonary fibrosis.

20. A method for inhibiting mitochondrial respiratory chain complex I comprising administering the compound of claim 6, or an enantiomer, diastereoisomer, racemic mixture, deuterated compound or pharmaceutically acceptable salt thereof, to a subject in need thereof.

* * * * *